(12) United States Patent
Hallahan et al.

(10) Patent No.: US 7,273,737 B2
(45) Date of Patent: Sep. 25, 2007

(54) *CIS*-PRENYLTRANSFERASES FROM PLANTS

(75) Inventors: David L. Hallahan, Wilmington, DE (US); Christopher Coldren, Cambridge, MA (US); Dennis Flint, Newark, DE (US); Hong Wang, Kennett Square, PA (US)

(73) Assignee: Pioneer Hi-Bred International, Inc., Johnston, IA (US)

( * ) Notice: Subject to any disclaimer, the term of this patent is extended or adjusted under 35 U.S.C. 154(b) by 370 days.

(21) Appl. No.: 10/700,171

(22) Filed: Nov. 3, 2003

(65) Prior Publication Data

US 2004/0152158 A1   Aug. 5, 2004

Related U.S. Application Data

(62) Division of application No. 09/655,908, filed on Sep. 6, 2000, now Pat. No. 6,645,747.

(60) Provisional application No. 60/155,046, filed on Sep. 21, 1999.

(51) Int. Cl.
*C07H 21/04* (2006.01)
*C12N 9/12* (2006.01)
*C12N 15/00* (2006.01)
*C12N 5/00* (2006.01)

(52) U.S. Cl. .............. 435/193; 435/483; 435/252.3; 435/320.1; 435/410; 435/325; 435/254.1; 435/254.2; 536/23.2; 536/23.4; 536/23.6

(58) Field of Classification Search ............ 435/193, 435/183, 252.3, 320.1, 410, 329, 254.1, 254.2; 536/23.1, 23.2, 23.4, 23.6
See application file for complete search history.

(56) References Cited

U.S. PATENT DOCUMENTS 6,316,695 B1   11/2001   Han et al.

OTHER PUBLICATIONS

Potrykus, Ingo, Biotechnology vol. 8 (6), pp. 535-542, Jun. 1990.*
EMBL Database, Heidelberg, FRG Empln accession No. AB023482 Mar. 15, 1999, Sasaki, T. et al., *Oryza sativa* genomic DNA, chromosome 6, clone P0680A03 XP002167058.

(Continued)

*Primary Examiner*—Richard Hutson

(57) ABSTRACT

This invention pertains to nucleic acid fragments encoding plant proteins that are homologs to the cis-prenyltransferases UPP synthase from the bacterium *Micrococcus luteus* or Dedol-PP synthase from yeast *Saccharomyces cerevisiae*. More specifically, this invention pertains to cis-prenyltransferase homologs from wheat, grape, soybean, rice, African daisy, rubber tree latex and pot marigold.

7 Claims, 24 Drawing Sheets

Polyprenol biosynthesis

OTHER PUBLICATIONS

EMBL Database, Heidelberg, FRG Empln accession No. AC007584 May 19, 1999, Lin, X. et al., *Arabidopsis thaliana* chromosomes II section 101 of 255 of the complete sequence. Sequence form clones MJB20, T19E12 XP002167059.

EMBL Database, Heidelberg, FRG Emest_Pln2 Accession No. AI965398 Aug. 24, 1999, Shoemaker, R. et al., sc71b10.y1 Gm-c1016 Glycine max cDNA clone Genome Systems Clone ID: Gm-c1016-1844 5' similar to SW: XP002167060.

EMBL Database, Heidelberg, FRG Emest_Pln4 accession No. AW038635 Sep. 17, 1999, D'Ascenzo, M. et al., "EST280318 tomato mixed elicitor, BTI *Lycopersicon esculentum* cDNA clone cLET719, mRNA sequence" XP002167061.

Kyung-Hwan Han et al., Genes expressed in the latex of *Hevea brasiliensis*, Tree Physiology 20, 503-510, 2000.

Tanaka, Y., In Rubber and Related Polyprenols., Methods in Plants Biochemistry; Dey, P. M. and Harborne, J. B., Eds., Academic Press: Sandiego, 1991, vol. 7, pp. 519-536. Charlwood et al., In Minor Classes of Terpenoids. Methods in Plants Biochemistry; Academic Press: San Diego, 1991; vol. 7, pp. 537-542.

McGarvey et al., Terpenoid Metabolism, Plant Cell 7: 1015-1026 (1995).

Chappell, J., Biochemistry and Molecular Biology of the Isoprenoid Biosynthetic Pathway in Plants, Annu. Rev. Plant Physiol. Plant Mol. Biol. 46: 521-547 (1995).

Asai et al., Biochem. Biophys. Res. Commun. 202:340-345 (1994).

Shimizu et al., Molecular Cloning, Expression, and Purification of Undecaprenyl Diphosphate Synthase, J. Biol. Chem. 273:19476-19481 (1998).

Apfel et al., Use of Genomics to Identify Bacterial Undecaprenyl Pyrophosphate Synthetase: Cloning, Expression, and Characterization of the Essential uppS Gene. J. Bacteriol. 181:483-492 (1999).

Sato et al., The Yeast RER2 Gene, Identified by Endoplasmic Reticulum Protein Localization Mutations, Encodes cis-Prenyltransferase, a Key Enzyme in Dolichol Synthesis, , Mol. Cell. Biol. 19:471-483 (1999).

GENBANK, ACC No. AB011483, *Arabidopsis thaliana*, Aug. 9, 2000.

GENBANK, ACC No. AB013498, *Saccharomyces cerevisiae*, Jan. 9, 1999.

GENBANK, ACC No. AB013497, *Saccharomyces cerevisiae*, Jan. 9, 1999.

Ngo et al., Computational Complexity; Protein Structure Prediction, and the Levinthal Paradox, in th Protein Folding Problem and Tertiary Structure Prediction, 1994, Merz et al., (ed).=, Birkhauser, Boston, MA pp. 433 and 492-495.

EMBL Database, Heidelberg, FRG, Nakamura, Y., *Arabidopsis thaliana* genomic DNA, chromosome 5, P1 clone: MZN1. Dec. 14, 1998, XP002160876.

EMBL Database, Heidelberg, Sasakii, T. et al., *Oryza sativa* genomic DNA, chromosome 6, clone P0680A03, Mar. 15, 1999, XP002167058.

EMBL Database, Heidelberg, FRG, Nakamura, Y., *Arabidopsis thaliana* genomic DNA, chromosome 5, P1 Clone: MUF9, Mar. 10, 1998, XP002160878.

Cornish, K. et al., Stabilisation of particle integrity and particle bound cis-prenyl transferase activity in stored, purified rubber particles, Phytochemical Analysis, 1997, vol. B, No. 3, Biosciences Information Service, Philadelphia, PA.

* cited by examiner

FIG. 2A

| | | 1 | | 50 |
|---|---|---|---|---|
| dms2c.pk005.c7 | (SEQ ID NO:1) | (1) | ---------------------------------------------- | |
| ecs1c.pk009.p19 | (SEQ ID NO:3) | (1) | ---------------------------------------------- | |
| ehb2c.pk001.i10 | (SEQ ID NO:5) | (1) | ---------------------------------------------- | |
| ehb2c.pk001.d17 | (SEQ ID NO:7) | (1) | ---------------------------------------------- | |
| ehb2c.pk001.o18 | (SEQ ID NO:9) | (1) | ---------------------------------------------- | |
| r10n.pk117.i23 | (SEQ ID NO:13) | (1) | ---------------------------------------------- | |
| rr1.pk005.h8 | (SEQ ID NO:15) | (1) | ---------------------------------------------- | |
| sll.pk0128.h7 | (SEQ ID NO:17) | (1) | ATGTTCTCGTTAAGACTCCCTATTCCTCTCGTTAAAACACCACTTCTCC | |
| vdb1c.pk001.k23 | (SEQ ID NO:11) | (1) | ---ATGCTCTCTTTTGATTTCCAATTTCAGCTGATAA | |
| wdk5c.pk005.f22 | (SEQ ID NO:19) | (1) | ---------------------------------------------- | |
| M.lutupps | (SEQ ID NO:23) | (1) | ---------------------------------------------- | |
| yeast rer2 | (SEQ ID NO:25) | (1) | ---------------------------------------------- | |
| yeast srt1 | (SEQ ID NO:27) | (1) | ---------------------------------------------- | |

| | | 51 | | 100 |
|---|---|---|---|---|
| dms2c.pk005.c7 | (SEQ ID NO:1) | (1) | ---------------------------------------------AT | |
| ecs1c.pk009.p19 | (SEQ ID NO:3) | (1) | ---------------------------------------------- | |
| ehb2c.pk001.i10 | (SEQ ID NO:5) | (1) | ---------------------------------------------- | |
| ehb2c.pk001.d17 | (SEQ ID NO:7) | (1) | ---------------------------------------------- | |
| ehb2c.pk001.o18 | (SEQ ID NO:9) | (1) | ---------------------------------------------- | |
| r10n.pk117.i23 | (SEQ ID NO:13) | (1) | ---------------------------------------------- | |
| rr1.pk005.h8 | (SEQ ID NO:15) | (1) | ---------------------------------------------- | |
| sll.pk0128.h7 | (SEQ ID NO:17) | (51) | CTCCTTGTTATTATTCTCACTATTATCACTATCGTTATCGTTATCGTTGTT | |
| vdb1c.pk001.k23 | (SEQ ID NO:11) | (36) | CGCTCGCCATACTTTCAAGTCCAAACACTCTTCTTGTACTTTTCGAAGTA | |
| wdk5c.pk005.f22 | (SEQ ID NO:19) | (1) | ---------------------------------------------- | |
| M.lutupps | (SEQ ID NO:23) | (1) | ---------------------------------------------- | |
| yeast rer2 | (SEQ ID NO:25) | (1) | ---------------------------------------------- | |
| yeast srt1 | (SEQ ID NO:27) | (1) | ------------ATGAAAATGCCCAGTATTATTCAGATTCAG | |

| | | 101 | | 150 |
|---|---|---|---|---|
| dms2c.pk005.c7 | (SEQ ID NO:1) | (3) | GCTTAAATCTTCCCCTCTACTTACCCAAATATCCTTGTTATTTCCCGGCCT | |

```
ecs1c.pk009.p19  (SEQ ID NO:3)    (1) ------------------------------------------------------
ehb2c.pk001.i10  (SEQ ID NO:5)    (1) ------------------------------------------------------
ehb2c.pk001.d17  (SEQ ID NO:7)    (1) ------------------------------------------------------
ehb2c.pk001.o18  (SEQ ID NO:9)    (1) ------------------------------------------------------
r10n.pk117.i23   (SEQ ID NO:13)   (1) ------------------------------------------------------
rr1.pk005.h8     (SEQ ID NO:15)   (1) --------------------------------ATGCTTGGCTCACTTATGTCT
sl1.pk0128.h7    (SEQ ID NO:17) (101) ATC--ATCCTTCCATCACCGTTCCCAAACACAGAGTCTTATCGTCTCGA
vdb1c.pk001.k23  (SEQ ID NO:11)  (86) ACAGAATCGATTCATTTTCTTTTCCTCCAATCTCAGTTCCAGATTTCAC
wdk5c.pk005.f22  (SEQ ID NO:19)   (1) ------------------------------------------------------
M.lutupps        (SEQ ID NO:23)   (1) ------------------------------------------------------
yeast rer2       (SEQ ID NO:25)   (1) ------------------------------------------------------
yeast srt1       (SEQ ID NO:27)  (31) TTTGTAGCCCTAAAAAGGCTTTTGTGTAGAAACCAAAGAACAGATGTGCTT 151                                                 200
dms2c.pk005.c7   (SEQ ID NO:1)   (53) CTCT---CTCCACCAACCACCACCGTGTCTTTATGTATTCAACCAATCA
ecs1c.pk009.p19  (SEQ ID NO:3)    (1) ------------------------------------------------------
ehb2c.pk001.i10  (SEQ ID NO:5)    (1) ----------------------ATGGAATTATACAACGGTGAGAGGC
ehb2c.pk001.d17  (SEQ ID NO:7)    (1) ----------------------ATGGAATTATACAACGGTGAGAGGC
ehb2c.pk001.o18  (SEQ ID NO:9)    (1) ----------------------ATGGAAATATATACGGGTCAGAGGC
r10n.pk117.i23   (SEQ ID NO:13)   (1) ------------------------------------------------------
rr1.pk005.h8     (SEQ ID NO:15)  (22) TACTTACCTTCAGTGGATTCAAAGACGGAGAACACTGATGAGTTAATTGC
sl1.pk0128.h7    (SEQ ID NO:17)(149) AGCGCGGTTCCGCCATTGCGAAGTGTCACGCTGATAGCGTGACACTTCGT
vdb1c.pk001.k23  (SEQ ID NO:11)(136) AAA----CTTCGC-ACAGCTAAAACTGATGTAG--------TTGGG
wdk5c.pk005.f22  (SEQ ID NO:19)   (1) --A----TGCCGC-TCTCC-AACTCT-ACGTCG-----------TCTGT
M.lutupps        (SEQ ID NO:23)   (1) ------------------------------------------------------
yeast rer2       (SEQ ID NO:25)   (1) -----------------------ATGGAAACGATAGTGGTAT
yeast srt1       (SEQ ID NO:27)  (81) CGCA---GTGAAAAGTATATTCAGAGAGTATTGCGTGGGTTATGTCAT 201                                                 250
dms2c.pk005.c7   (SEQ ID NO:1) (100) GACACCACTGGAGGTGAATTAATTCGCTGGAGGGAAGCGATACTCCGC
ecs1c.pk009.p19  (SEQ ID NO:3)    (1) ------------------------------------------------------
ehb2c.pk001.i10  (SEQ ID NO:5)   (26) CRAGTGTGTTCAGACT--TTAGGAGAGTATATGAGAACGCATTACTCCGC
ehb2c.pk001.d17  (SEQ ID NO:7)   (26) CAAGTGTGTTCAGACT--TTAGAGAGTATATGAGAAAGGGTTATATT
ehb2c.pk001.o18  (SEQ ID NO:9)   (26) CAAGTGTGTTAGAAT--TTTGGGAATACATGAGAATTTCATCCGCAATGT
r10n.pk117.i23   (SEQ ID NO:13)   (1) ------------------------------------------------------
rr1.pk005.h8     (SEQ ID NO:15)  (72) GACTGGGTGTTCTTGCTAGTCGCCAGAATTTCATCCGCAATGCATTGTAG
```

```
ecs1c.pk009.p19 (SEQ ID NO:3)    (684)  TTAA------------------------------------------------------
ehb2c.pk001.i10 (SEQ ID NO:5)    (842)  ACTTGGAGAAAC-ATAAGGAATATACTTAAAATAA------------------------
ehb2c.pk001.d17 (SEQ ID NO:7)    (842)  ACTTGGAGAAAC-ATAAGGAATATACTTAAAATAA------------------------
ehb2c.pk001.o18 (SEQ ID NO:9)    (860)  ATTTGGAGAANGC-ATAAGGAATATTTAAAATAA-------------------------
r10n.pk117.i23  (SEQ ID NO:13)   (719)  CTATTGAGCAA--AGCAGAAATCTGGCTAAGAAGCAGCTG-------------------
rr1.pk005.h8    (SEQ ID NO:15)   (860)  CTATTGAGCAA--AGCAGAAATCTGGCTAAGAAGCAGCTGTAA----------------
sl1.pk0128.h7   (SEQ ID NO:17)   (948)  CTATGGTTGTCG-ACATTCATAA------------------------------------
vdb1c.pk001.k23 (SEQ ID NO:11)   (912)  ATATGGTTGGGCG-AAACTGA--------------------------------------
wdk5c.pk005.f22 (SEQ ID NO:19)   (768)  CTTTGGAGAAG-AAAAACAATGCAGCGCTATAA--------------------------
M.lutupps       (SEQ ID NO:23)   (735)  TTTTGGTTGATT-ATAA------------------------------------------
yeast rer2      (SEQ ID NO:25)   (836)  ATTTGAAAGTAA-AAAAGTTGAATTAA--------------------------------
yeast srt1      (SEQ ID NO:27)   (951)  ATTTAAAAAAGAAAAGAAAACAGCTATGTCTTTGTACAACTTTCCAAACCCCC 1101                                                   1132
dms2c.pk005.c7  (SEQ ID NO:1)    (865)  ----------------------------------
ecs1c.pk009.p19 (SEQ ID NO:3)    (688)  ----------------------------------
ehb2c.pk001.i10 (SEQ ID NO:5)    (874)  ----------------------------------
ehb2c.pk001.d17 (SEQ ID NO:7)    (874)  ----------------------------------
ehb2c.pk001.o18 (SEQ ID NO:9)    (892)  ----------------------------------
r10n.pk117.i23  (SEQ ID NO:13)   (757)  ----------------------------------
rr1.pk005.h8    (SEQ ID NO:15)   (901)  ----------------------------------
sl1.pk0128.h7   (SEQ ID NO:17)   (970)  ----------------------------------
vdb1c.pk001.k23 (SEQ ID NO:11)   (931)  ----------------------------------
wdk5c.pk005.f22 (SEQ ID NO:19)   (802)  ----------------------------------
M.lutupps       (SEQ ID NO:23)   (751)  ----------------------------------
yeast rer2      (SEQ ID NO:25)   (862)  ----------------------------------
yeast srt1      (SEQ ID NO:27)  (1001)  CCATTTCAGTTTCGGTTACAGGAGATGAATAA
```

FIG. 2J

|     |     | 1 | 50 |
| --- | --- | --- | --- |
| dms2c.pk005.c7 | (SEQ ID NO:2) | (1) | ------------------------------------------------ |
| ecs1c.pk009.p19 | (SEQ ID NO:4) | (1) | --------------------------------CYFPASLSTNHHRGLYVF |
| ehb2c.pk001.i10 | (SEQ ID NO:6) | (1) | ---------------------------------------MELYNG |
| ehb2c.pk001.d17 | (SEQ ID NO:8) | (1) | ---------------------------------------MELYNG |
| ehb2c.pk001.o18 | (SEQ ID NO:10) | (1) | ---------------------------------------MEIYTG |
| vdb1c.pk001.k23 | (SEQ ID NO:12) | (1) | MLSFRFPISADNARHTFKSKHSSCTFRSNRIDSFSFPPISVPRFHKLRTA |
| r10n.pk117.i23 | (SEQ ID NO:14) | (1) | ------------------------------------------------ |
| rr1.pk0050.h8 | (SEQ ID NO:16) | (1) | -------------------------MLGSLMSYLPSVDSKTENTDEL |
| sl1.pk0128.h7 | (SEQ ID NO:18) | (1) | MFSLRLPIPLVKTPPSPSCYYSHYHYRYRCYHPFHHRSQTQSLIVSK |
| wdk5c.pk005.f22 | (SEQ ID NO:20) | (1) | ------------------------------------------MPLSN |

|     |     | 51 | 100 |
| --- | --- | --- | --- |
| dms2c.pk005.c7 | (SEQ ID NO:2) | (31) | NQSDTTGGGINSLEERIT------------PAGEKHELMPKHVAVIMDGN |
| ecs1c.pk009.p19 | (SEQ ID NO:4) | (1) | -----------------------------------MPKHVAFIMDGN |
| ehb2c.pk001.i10 | (SEQ ID NO:6) | (7) | ERPSMFRLLGKYMRKGLY------------SITTQGPIPTHIALLDGN |
| ehb2c.pk001.d17 | (SEQ ID NO:8) | (7) | ERPSMFRLLEKYMRKGLY------------SITTQGPIPTHIALLDGN |
| ehb2c.pk001.o18 | (SEQ ID NO:10) | (7) | QRPSMFRIFGKYMRKGLY------------SITTQGPIPTLAIMDGN |
| vdb1c.pk001.k23 | (SEQ ID NO:12) | (51) | KTDVMGEEEAREVNERAEEF----------PDGRRELMPEHVAVIMDGN |
| r10n.pk117.i23 | (SEQ ID NO:14) | (1) | -----------------------------------MPKHIAFLMDGN |
| rr1.pk0050.h8 | (SEQ ID NO:16) | (23) | IATGMLASLQNFIRKCIV------------AVISYGPMPKHVAVIMDGN |
| sl1.pk0128.h7 | (SEQ ID NO:18) | (51) | RGSAIAKCHADSVTLRDDGVSLAQESLEPLPAEEAAEMMPKHVAVIMDGN |
| wdk5c.pk005.f22 | (SEQ ID NO:20) | (6) | STSSMPAVTVPAAEELLS------------QGIRAESLPRMALVMDGN |

|     |     | 101 | 150 |
| --- | --- | --- | --- |
| dms2c.pk005.c7 | (SEQ ID NO:2) | (69) | RWARSRGMPDACYMEGARSLKVMVELGRKWGIQVLRVFAFSADNWLRP |
| ecs1c.pk009.p19 | (SEQ ID NO:4) | (13) | RWVEKGWSPMTEHSAMRKTQSLFRGSKFKIAVSIYAFSTENWTRP |
| ehb2c.pk001.i10 | (SEQ ID NO:6) | (44) | RFAKKHKIPEGGCHKAGFLAGLNVETGYELGVKYAIIVAFSIDNFREK |
| ehb2c.pk001.d17 | (SEQ ID NO:8) | (44) | RFAKKHKMKEAEGYKAGYLALLRTTNVGYELGVRYVIIYAFSIDNFREK |
| ehb2c.pk001.o18 | (SEQ ID NO:10) | (44) | RFAKKHKMKEAASCHOAGYRSLRELVELGCKWGIKVLSYFAFSYDNWSRS |
| vdb1c.pk001.k23 | (SEQ ID NO:12) | (91) | VSWMQKRGYBAASIQEGSCHRVGFSAEIASHLMCFMSVEHHAMVKHFKED |
| r10n.pk117.i23 | (SEQ ID NO:14) | (13) | RRYAKFESIQEGSCHRVGFSAEIASHLMGYEMGVKHIIVYAFSIDNFKED |
| rr1.pk0050.h8 | (SEQ ID NO:16) | (60) | RRYAKFESIQEGSCHRVGFSAEIASHLYGYEMGVKHIIVYAFSIDNFKED |

```
rr1.pk0050.h8    (SEQ ID NO:16)  (197)  ----R---DILQREDADSVANNGVWSDISVADDDRHMKSAGCPDPDIVIRT
sl1.pk0128.h7    (SEQ ID NO:18)  (244)  ---------------------INENIIEQELEINCTEFYPDERIRT
wdk5c.pk005.f22  (SEQ ID NO:20)  (186)  ---------------------IDESIFADEQH--SETSCPDEIRT 301                                              350
dms2c.pk005.c7   (SEQ ID NO:2)   (238)  SGELRVSNEFLMQLAYTELWESETLWPDEGEDELHALNTEQHRRRYGG
ecs1c.pk009.p19  (SEQ ID NO:4)   (182)  SGEIRLSNEMLMQMAYSELWETDKYFPDEGENDIEALLAQKVRKC---
ehb2c.pk001.i10  (SEQ ID NO:6)   (235)  SGETRESNYLMQLTNCILYSPYALWPEIGLRHVMSVINEQRHYSYLEK
ehb2c.pk001.d17  (SEQ ID NO:8)   (235)  SGETRESNYLMQLTNCILYSPYALWPEIGLRHVMSVINEQRHYSYLEK
ehb2c.pk001.o18  (SEQ ID NO:10)  (241)  SGLSRISNYLMQDSNCILYMSDFARWPEIGLRHEVATVMNEQRHHSYLEK
vdb1c.pk001.k23  (SEQ ID NO:12)  (258)  SGEIRVSNEMLMQIAYTELCEFSTLWQNEDPLWPEMSFKHLWAILSSEKRQRRYGG
r10n.pk117.i23   (SEQ ID NO:14)  (194)  SGETRLSNFLMQLTFSHLQNEDPLWPEMSFKHLWAILQYERVHPSIEQ
rr1.pk0050.h8    (SEQ ID NO:16)  (241)  SGETRLSNFLMQLTFSHLQNEDPLWPEMSFKHEVWAILQYERVHPSIEQ
sl1.pk0128.h7    (SEQ ID NO:18)  (270)  SGEIRLSNFLMQLAYTEFXENRELWPDEGKDEFVDALSSLQORRYGG
wdk5c.pk005.f22  (SEQ ID NO:20)  (210)  SGELRESNLVSNEFLMQSAYSELFFTDTLWPDEGEAQYLQAMMAEOSRDRRFGR 351
dms2c.pk005.c7   (SEQ ID NO:2)   (288)  --------------
ecs1c.pk009.p19  (SEQ ID NO:4)   (229)  --------------
ehb2c.pk001.i10  (SEQ ID NO:6)   (285)  HKEYLK--------
ehb2c.pk001.d17  (SEQ ID NO:8)   (285)  HKEYLK--------
ehb2c.pk001.o18  (SEQ ID NO:10)  (291)  HKEYLK--------
vdb1c.pk001.k23  (SEQ ID NO:12)  (308)  RN------------
r10n.pk117.i23   (SEQ ID NO:14)  (244)  SRNLAKKQL-----
rr1.pk0050.h8    (SEQ ID NO:16)  (291)  SRNLAKKQL-----
sl1.pk0128.h7    (SEQ ID NO:18)  (320)  RHS-----------
wdk5c.pk005.f22  (SEQ ID NO:20)  (260)  RKNNAAL-------
```

FIG 3C

```
                                                              1                                                        50
M.lutUPPS  (SEQ ID NO:24)   (1) --------------------------------------------------
Yeastsrt1  (SEQ ID NO:28)   (1) -------------------------MKMPSIIQIQFVALKRLLVETKEQMCF
Yeastrer2  (SEQ ID NO:26)   (1) --------------------------------------------METDSGIP
dms2c.pk005.c7 (SEQ ID NO:2)   (1) --------------------------------CYFPASLSTNHHRGLYVF
ecs1c.pk009.p19 (SEQ ID NO:4)  (1) --------------------------------------------MLNLPLYLPKYP-
ehb2c.pk001.i10 (SEQ ID NO:6)  (1) --------------------------------------------------MELYNG
ehb2c.pk001.d17 (SEQ ID NO:8)  (1) --------------------------------------------------MELYNG
ehb2c.pk001.o18 (SEQ ID NO:10) (1) --------------------------------------------------MEIYTG
vdb1c.pk001.k23 (SEQ ID NO:12) (1) MLSFRFPISADNARHTFKSKHSSCTFRSNRIDSFSFPPISVPRFHKLRTA
r10n.pk117.i23 (SEQ ID NO:14)  (1) --------------------------------------------------
rr1.pk0050.h8 (SEQ ID NO:16)   (1) -----------------------------MLGSLMSYLPSVDSKTENTDEL
s11.pk0128.h7 (SEQ ID NO:18)   (1) MFSLRLPIPLVKTPPSPSCYSHYHYRYRYRCYHPFHHRSQTQSLIVSK
wdk5c.pk005.f22 (SEQ ID NO:20) (1) --------------------------------------------MPLSN 51                                                       100
M.lutUPPS  (SEQ ID NO:24)  (1) ----MFPIKKRKAIKNNN---------------------------------INAAQIPKHIHIHMDGN
Yeastsrt1  (SEQ ID NO:28)  (28) AVKSIFQRVFAWVMSLSLFSWFYVNLQNILIKAIRVGPVPEHMSEMDGN
Yeastrer2  (SEQ ID NO:26)  (9) GHSEVLKWTKNIFSRTLR---------------------------ASNCVFRHVGIMDGN
dms2c.pk005.c7 (SEQ ID NO:2) (31) NQSDTTGGGINSLEERIT---------------------------PAGIKHELMPKHVAVIMDGN
ecs1c.pk009.p19 (SEQ ID NO:4) (1) --------------------------------------------MPKIFTIIATEMDGN
ehb2c.pk001.i10 (SEQ ID NO:6) (7) ERPSVFRLLGKYMRKGLY---------------------------SIITQGPIFTIIAPEMDGN
ehb2c.pk001.d17 (SEQ ID NO:8) (7) ERPSVFRLLEKYMRKGLY---------------------------SIITQGPIFTIIGSIMDGN
ehb2c.pk001.o18 (SEQ ID NO:10) (7) QRPSVFRIFGKYMRKGLY---------------------------SIITQGPIFTHLAETMDGN
vdb1c.pk001.k23 (SEQ ID NO:12) (51) KTDVIGEEEAREVNERAEEF-------------------------PDGIRRELMPEHVAVIMDGN
r10n.pk117.i23 (SEQ ID NO:14) (1) --------------------------------------------MPKIAIHMDGN
rr1.pk0050.h8 (SEQ ID NO:16) (23) IATGMLASLQNFIRKCIV---------------------------AVISYGPMEKHIPERVMDGN
s11.pk0128.h7 (SEQ ID NO:18) (51) RGSAIAKCHADSVTLRDDGVSLAQESLEPLPAEIAAEMMIKHVAVEMDGN
wdk5c.pk005.f22 (SEQ ID NO:20) (6) STSSVPAVTVPAAEELLS---------------------------QGIRAESLPRHVALVMDGN 101                                                       150
M.lutUPPS  (SEQ ID NO:24) (32) GRWAKQKKMERIKGHYEGMQTVKKITRYASDLGVKYLILVAFSTENWSRP
```

FIG. 4A

```
Yeaststr1  (SEQ ID NO:28)  (78)  RRYAKSRRLRVKKGHEAGGLTLTLYICKRLGVKCVSAYAFSLENFRP
Yeastrer2  (SEQ ID NO:26)  (43)  RRFARKKEMDVKEGHEAGFVSMSRILELGYEAGVDTAVFAESHENKRS
dms2c.pk005.c7 (SEQ ID NO:2) (69) RRWARSRGLMPDAGYMEGARSLKVMVELGRKWGIQVLTVFAESADNWLRP
ecs1c.pk009.p19 (SEQ ID NO:4) (13) RRWVEKGWSPMTCHSAMRKTLQSLEFRGSKFKIKAVSIYATIKAFSFENFRK
ehb2c.pk001.i10 (SEQ ID NO:6) (44) RRFAKKHHKLPEGGGHKGFLALLNVITYCYELGVKYATIKAFSENFRK
ehb2c.pk001.d17 (SEQ ID NO:8) (44) RRFAKKHHKLPEGGGHKGFLALLNVITYCYELGVKYATIKAFSENFRK
ehb2c.pk001.o18 (SEQ ID NO:10) (44) RRFAKKHHKMKEAEGYKAGYLALRTETYCYELGVRYVHLVSVFAFSYDNFRK
vdb1c.pk001.k23 (SEQ ID NO:12) (91) VPWAQKRGLRAASCHQAGVRSLRELVELCCKWGIKVLSVFAFSYDMWSRS
r10n.pk117.i23 (SEQ ID NO:14) (13) RRYAKFRSIQEGSGHRVGFSALIASLYQEMGVAYIHVKAFSIHNFKD
rr1.pk0050.h8 (SEQ ID NO:16) (60) RRYAKFRSIQEGSGHRVGFSALIASLYQEMGVAYIHVLVFAFSTDWVRP
sl1.pk0128.h7 (SEQ ID NO:18) (101) GRWAKVKGLDPSACHQAGVQSLRKMVRLGCSWGIEVLVFAESTDWVRP
wdk5c.pk005.f22 (SEQ ID NO:20) (43) SRWAARGLBPTDGHEHGMRALMRTVRLSRAWGIRVLIAFGESLEWNRP 151                                            200
M.lutUPPS  (SEQ ID NO:24)  (82)  KDEVNYLMKLPGDFLNTFLPELIEKN-----VKVETIGFIDDLPDHTKKA
Yeaststr1  (SEQ ID NO:28)  (128) KEEVDTLMNLFTVKLDEFAKRAKDYKDPLYGSKIRIVGDQSLLSPEMRKK
Yeastrer2  (SEQ ID NO:26)  (93)  SREVESELNTLARERLRQITERGELACK--YGVRIKIGDLSLLDKSLLED
dms2c.pk005.c7 (SEQ ID NO:2) (119) KVEVDFLNGLIESVLKDEVVHMIKE-----GIQLSVIGDTSKLPKSVKRI
ecs1c.pk009.p19 (SEQ ID NO:4) (63) KEEVDFLMEMYLDLMLEKLEGMIMEESIINA--YDICVRFVGNLKLLSEPVKTA
ehb2c.pk001.i10 (SEQ ID NO:6) (94) PHEVQYVMDLMLEKLEGMIMEESIINA--YDICVRFVGNLKLLSEPVKTA
ehb2c.pk001.d17 (SEQ ID NO:8) (94) PHEVQYVMDLMLEKLEGMIMEESIINA--YDICVRFVGNLKLLSEPVKTA
ehb2c.pk001.o18 (SEQ ID NO:10) (94) PREVQCVNLMMEKLEEIIVEESIMNA--YDVGVRIVGNLNLDEPIRIA
vdb1c.pk001.k23 (SEQ ID NO:12) (141) EGEVGFLMSLIERVVKAELPILG------GKAFECRDWGFVKASEQLQL
r10n.pk117.i23 (SEQ ID NO:14) (63) PTEVKSLELMEKLNELLENRNVINK--VNCKINFWGNLDMLSKSVRVA
rr1.pk0050.h8 (SEQ ID NO:16) (110) PTEVKSLELMBEKLNELLENRNVINK--VNCKINFWGNLDMLSKSVRVA
sl1.pk0128.h7 (SEQ ID NO:18) (151) KVEVDFLLRLFERTLNSEVQTFKRE-----GIRISVIGDSSRLPESLKRM
wdk5c.pk005.f22 (SEQ ID NO:20) (93) KAEVDFTLVALIERFINDNLAEFLRE-----GTRLRIIGDRSRDPISVQKT 201                                            250
M.lutUPPS  (SEQ ID NO:24)  (127) VLEAKEKTKHNTGLTLVFALNYGGRKELISAVQLIAERYKSGEISLDE--
Yeaststr1  (SEQ ID NO:28)  (178) IKKVEEIHQDGDDFTEFICFPYTSRNDMLHTIRDSVEDHLEN----KSP-
Yeastrer2  (SEQ ID NO:26)  (141) VRVAVETKNNKRATENICFPVTGREELLHMKETIVQHKKGAAIDES--
dms2c.pk005.c7 (SEQ ID NO:2) (164) ITYAENILKNNSQLNLVVALNVGKYDLVQACQSIALKVKDGVIQPEE--
ecs1c.pk009.p19 (SEQ ID NO:4) (108) CIEIEEKSRANSGTHVNYNLNVSGKYDLIEACKSVATKVKDGVIiPKQ--
ehb2c.pk001.i10 (SEQ ID NO:6) (142) ADKIMRALANNSKCVLIAVCLTSTDELVLHAVEESS--ELNSNEVCNN--
ehb2c.pk001.d17 (SEQ ID NO:8) (142) ADKIMRALANNSKCVLIAVCLTSTDELVLHAVEESS--ELNSNEVCNN--
ehb2c.pk001.o18 (SEQ ID NO:10) (142) AEKIMRALANNSGFVLLIAVASSTDELGHAVEESSKDKLNSNEVCNNGI
```

```
vdb1c.pk001.k23  (SEQ ID NO:12)  (184)  IIDVEETTKENSRLQFIVALSYSGQCDTLQACKNIGHKVKDGLIEPED--
r10n.pk117.i23   (SEQ ID NO:14)  (111)  AEKLMATTAENTGLVFSVCMPYNSTSEYVNAVNKVC-------AER---
rrl.pk0050.h8    (SEQ ID NO:16)  (158)  AEKLMATTAENTGLVFSVCMPYNSTSEYVNAVNKVC-------AER---
sll.pk0128.h7    (SEQ ID NO:18)  (196)  IASAEDIKQNSRFQHIVAVGISGKYDVYQACKSVAKKVKDGHIHLDD--
wdk5c.pk005.f22  (SEQ ID NO:20)  (138)  ARDAEHAIRNNSQLDHVLHISLSGRMDHVQHCRNLAQKVDAKLLRPED--

300
M.lutUPPS        (SEQ ID NO:24)  (175)  -----------------------------ISETHFNEYLFT--ANMEDELI
Yeastsrt1        (SEQ ID NO:28)  (223)  ------R--------------------INIRKFTNKMYMG-FHSNKCELI
Yeastrer2        (SEQ ID NO:26)  (189)  --------------------------TLESHLYTAGVHPLEDEI
dms2c.pk005.c7   (SEQ ID NO:2)   (212)  ---------------------INEFTIENLLGHNCIPFRHPDEVI
ecs1c.pk009.p19  (SEQ ID NO:4)   (156)  -------------------IDEKYFKQELGHKMIDFYPDEVI
ehb2c.pk001.i10  (SEQ ID NO:6)   (188)  ---QELEEANATGSSTVIQTENMESYSGIKLVDLEKNTYIN---PYPDVI
ehb2c.pk001.d17  (SEQ ID NO:8)   (188)  ---QELEEANATGSSTVIQTENMESYSGIKLVDLEKNTYIN---PYPDVI
ehb2c.pk001.o18  (SEQ ID NO:10)  (192)  EAEQEFKEANGTG-NSVIPVQKTESYSGINLADLEKNTYVN--IHRIVI
vdb1c.pk001.k23  (SEQ ID NO:12)  (232)  ----------------INKSLIEQELQINCTEFEPDEIVI
vdb1c.pk117.i23  (SEQ ID NO:14)  (150)  ------R----DILQREDADSVANNGVYSDISVADLDRHMYSAGCHDEIVI
rrl.pk0050.h8    (SEQ ID NO:16)  (197)  ------R----DILQREDADSVANNGVYSDISVADLDRHMYSAGCHDEIVI
sll.pk0128.h7    (SEQ ID NO:18)  (244)  ---------------INENIIEQLEHNCTEFYPDEI
wdk5c.pk005.f22  (SEQ ID NO:20)  (186)  ---------------IDESLFADELQL--SETSCPDEI 350
M.lutUPPS        (SEQ ID NO:24)  (197)  RTSGEERTSNEIIHCSYS--EFVHIDEFWPDINEESLAQCISIYONRHR
Yeastsrt1        (SEQ ID NO:28)  (247)  RTSGHRFISDYMIQVHEN-ATIEESBTLWPNESFFAMYLMILKWSFFST
Yeastrer2        (SEQ ID NO:26)  (207)  RTSGVSRISDEIIQASSKGVRIELLDCLWPEEGPIRMAWILLKESFHKS
dms2c.pk005.c7   (SEQ ID NO:2)   (236)  RTSGLRVSNEFIQLAYT--EIYHSETLWPDEGEDELLHALNTFQHRRR
ecs1c.pk009.p19  (SEQ ID NO:4)   (180)  RTSGHIRVSNEMWMQMAYS--EIYETDKYFDEGENDLIEALLAFQKVRK
ehb2c.pk001.i10  (SEQ ID NO:6)   (233)  RTSGETRISNYIMQTTNC--ILYSPYALWPEIGLRHVWSVINEQRHYS
ehb2c.pk001.d17  (SEQ ID NO:8)   (233)  RTSGETRISNYIMQTTNC--ILYSPYALWPEIGLRHVWSVINEQRHYS
ehb2c.pk001.o18  (SEQ ID NO:10)  (239)  RTSGLSRLVSNEMIQTSNC--IIYSPFALWPEIGLRHLWTVMNEQRHHS
vdb1c.pk001.k23  (SEQ ID NO:12)  (256)  RTSGELRVSNEMWIQIAYT--ELICEFSTIWPDGKDEFVEALSSEQKRQR
vdb1c.pk117.i23  (SEQ ID NO:14)  (192)  RTSGETRISNEWPEMQTTFS--HEQNPDPLWPEESFKHLVWAILQYQRVHP
rrl.pk0050.h8    (SEQ ID NO:16)  (239)  RTSGETRISNEWPEMQTTFS--HEQNPDPLWPEESFKHLVWAILQYQRVHP
sll.pk0128.h7    (SEQ ID NO:18)  (268)  RTSGELRVSNERELWDEGKDEFVDALSSEQRQR
wdk5c.pk005.f22  (SEQ ID NO:20)  (208)  RTSGELRESNEWPEMQSAVS--EIFSTDTIMDEGAQYLQAMMAEQSRDR
```

```
                                    351                                                  398
M.lutUPPS    (SEQ ID NO:24)   (245) RFGGL-------------------------------------------------
Yeastsrt1    (SEQ ID NO:28)   (296) IQKYNEKNHSLFEKIHESVPSIFKKKTAMSLYNFPNPPISVSVTGDE
Yeastrer2    (SEQ ID NO:26)   (257) FLNKEYRLEEGDYDEETNGDPIDLKEKKLN-------------------
dms2c.pk005.c7   (SEQ ID NO:2)  (284) RYGG----------------------------------------------
ecs1c.pk009.p19  (SEQ ID NO:4)  (228) C-------------------------------------------------
ehb2c.pk001.i10  (SEQ ID NO:6)  (281) YLEKHKEYLK----------------------------------------
ehb2c.pk001.d17  (SEQ ID NO:8)  (281) YLEKHKEYLK----------------------------------------
ehb2c.pk001.o18  (SEQ ID NO:10) (287) YLEKHKEYLK----------------------------------------
vdb1c.pk001.k23  (SEQ ID NO:12) (304) RYGGRN--------------------------------------------
r10n.pk117.i23   (SEQ ID NO:14) (240) SIEQSRNLAKKQL-------------------------------------
rr1.pk0050.h8    (SEQ ID NO:16) (287) SIEQSRNLAKKQL-------------------------------------
sl1.pk0128.h7    (SEQ ID NO:18) (316) RYGGRHS-------------------------------------------
wdk5c.pk005.f22  (SEQ ID NO:20) (256) RFGRRKNNAAL---------------------------------------
```

CIS-PRENYLTRANSFERASES FROM PLANTS

This Application claim the benefit of U.S. Provisional Application 60/155,046, filed Sep. 21, 1999.

FIELD OF THE INVENTION

This invention is in the field of plant molecular biology. This invention pertains to nucleic acid fragments from plants encoding proteins that are homologs of the undecaprenyl diphosphate and dehydrodolichyl diphosphate synthases (cis-prenyltransferases) previously identified only in microbes. More specifically, this invention pertains to homologs from wheat, grape, soybean, rice, African daisy, rubber tree and pot marigold.

BACKGROUND OF THE INVENTION

Plants synthesize a variety of hydrocarbons built up of isoprene units ($C_5H_8$), termed polyisoprenoids (Tanaka, Y. In *Rubber and Related Polyprenols. Methods in Plant Biochemistry*; Dey, P. M. and Harbome, J. B., Eds., Academic Press: San Diego, 1991; Vol. 7, pp 519-536). Those with from 45 to 115 carbon atoms, and varying numbers of cis-and trans- (Z- and E-) double bonds, are termed polyprenols, while those of longer chain length are termed rubbers (Tanaka, Y. In *Minor Classes of Terpenoids. Methods in Plant Biochemistry*; Dey, P. M. and Harbome, J. B., Eds., Academic Press: San Diego, 1991; Vol. 7, pp 537-542). The synthesis of these compounds is carried out by a family of enzymes termed prenyltransferases, which catalyze the sequential addition of $C_5$ units to an initiator molecule.

The initiator molecules themselves are derived from isoprene units through the action of distinct prenyltransferases, and are allylic terpenoid diphosphates such as dimethylallyldiphosphate (DMAPP), but more usually the $C_{10}$ compound geranyl diphosphate (GPP), the $C_{15}$ compound farnesyl diphosphate (FPP) or the $C_{20}$ compound geranylgeranyl diphosphate (GGPP). Genes encoding the enzymes which synthesize these allylic terpenoid diphosphates have been cloned from a number of organisms, including plants, and all of these genes encode polypeptides with conserved regions of homology (McGarvey et al., *Plant Cell* 7:1015-1026 (1995); Chappell, J., *Annu. Rev. Plant Physiol. Plant Mol. Biol.* 46:521-547 (1995)). All of these gene products condense isoprene units in the trans- configuration. Prenyltransferases which condense isoprene units in a cis-configuration have not been identified in higher animals or plants, nor have prenyltransferases catalyzing extension of the polyisoprenoid chain beyond the $C_{20}$ compound geranylgeranyl diphosphate.

A gene encoding octaprenyl diphosphate (OPP) synthase from the bacterium *E. coli* was identified (Asai et al., *Biochem. Biophys. Res. Commun.* 202:340-345 (1994)), and more recently, genes encoding bacterial undecaprenyl diphosphate (UPP) synthases (Shimizu et al., *J. Biol. Chem.* 273:19476-19481 (1998); Apfel et al., *J. Bacteriol.* 181:483-492 (1999)) and yeast dehydrodolichyl diphosphate (Dedol-PP) synthase (Sato et al., *Mol. Cell. Biol.* 19:471-483 (1999)) were identified. OPP synthase generates the all-trans polyisoprenoid side chain of biological quinones (ubiquinone-8, menaquinone-8 and dimethylmenaquinone-8), and its primary structure contains regions of similarity with GPP, FPP and GGPP synthases. UPP synthase and Dedol-PP synthase generate cis-polyisoprenoids, and their primary structures are related to each other but distinct from those of OPP, GPP, FPP and GGPP synthases.

There are several suggested functions for plant polyisoprenoids. Terpenoid quinones are most likely involved in photophosphorylation and respiratory chain phosphorylation. Rubbers have been implicated in plant defense against herbivory, possibly serving to repel and entrap insects and seal wounds in a manner analogous to plant resins. The specific roles of the $C_{45}$-$C_{115}$ polyprenols remain unidentified, although as with most secondary metabolites they too most likely function in plant defense. Short-chain polyprenols may also be involved in protein glycosylation in plants, by analogy with the role of dolichols in animal metabolism.

The problem to be solved is to identify new plant genes having utility in plant defense mechanisms. Applicants have solved the stated problem by the identification of plant genes encoding plant cis-prenyltransferases. The present invention presents genes with significant homology to the bacterial UPP synthase and yeast Dedol-PP synthase from plants. The present invention shows that such genes are present in a range of plant species, including economically important crop plants such as cereals and the rubber tree *Hevea brasiliensis*, and thus are likely to be ubiquitous in plants.

This invention pertains to the identification and characterization of EST sequences from wheat, grape, soybean, rice, African daisy, rubber tree and pot marigold encoding cis-prenyltransferase proteins from these species.

SUMMARY OF THE INVENTION

It is an object of the present invention to provide an isolated nucleic acid fragment encoding a plant cis-prenyltransferase protein selected from the group consisting of: (a) an isolated nucleic acid fragment encoding all or a substantial portion of the amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18 and SEQ ID NO:20; (b) an isolated nucleic acid fragment that is substantially similar to an isolated nucleic acid fragment encoding all or a substantial portion of the amino acid sequence selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18 and SEQ ID NO:20; (c) an isolated nucleic acid fragment encoding a polypeptide, the polypeptide having at least 41% identity with the amino acid sequence set forth in SEQ ID NO:24; (d) an isolated nucleic acid fragment encoding having at least 50% identity with nucleic acid sequence as set forth in SEQ ID NO:23; (e) an isolated nucleic acid molecule that hybridizes with a nucleic acid sequence of (a) (b), (c) or (d) under the following hybridization conditions: 0.1×SSC, 0.1% SDS, 65° C. and washed with 0.2×SSC, 0.5% SDS; (f) an isolated nucleic acid fragment that hybridizes with a nucleic acid sequence selected from the group consisting of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17 and SEQ ID NO:19 under the following hybridization conditions 0.1×SSC, 0.1% SDS, 65° C. and washed with 0.2×SSC, 0.5% SDS; and (g) an isolated nucleic acid fragment that is complementary to (a), (b), (c), (d), (e) or (f).

The invention further provides polypeptides encoded by the isolated nucleic acid fragments of the present invention, such as are presented in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18 and SEQ ID NO:20.

In another embodiment the invention provides a chimeric gene comprising the isolated nucleic acid fragment of the present invention operably linked to suitable regulatory sequences.

The invention additionally provides a method of altering the level of expression of a plant cis-prenyltransferase protein in a host cell comprising: (a) transforming a host cell with the chimeric gene of the present invention and; (b) growing the transformed host cell produced in step (a) under conditions that are suitable for expression of the chimeric gene resulting in production of altered levels of a plant cis-prenyltransferase protein in the transformed host cell relative to expression levels of an untransformed host cell. The invention further provides that where the cis-prenyltransferase protein is expressed in a transformed plant that the defense mechanism of the plant will be modulated.

The invention additionally provides transformed host cells comprising the chimeric genes of the present invention.

In an alternative embodiment the invention provides methods of obtaining a nucleic acid fragment encoding all or a substantial portion of the amino acid sequence encoding a plant cis-prenyltransferase protein using portions of the present nucleic acid sequences as hybridization probes or as primers.

BRIEF DESCRIPTION OF THE DRAWINGS AND SEQUENCE DESCRIPTIONS

FIG. 1 shows a scheme for synthesis of GPP, FPP and GGPP from IPP and the synthesis of polyprenols from GPP, FPP and GGPP.

Figure 2C:
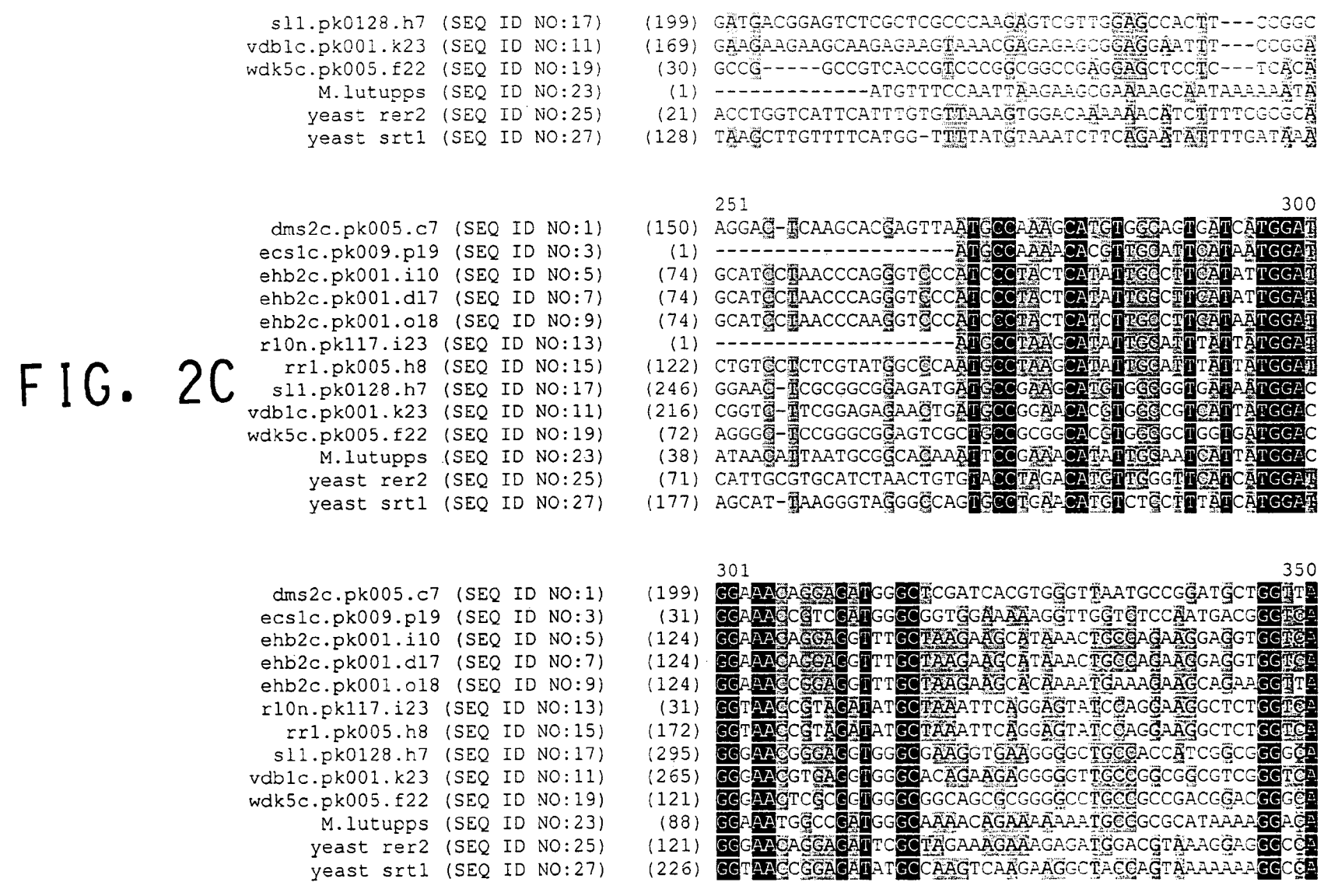
Figure 2D:
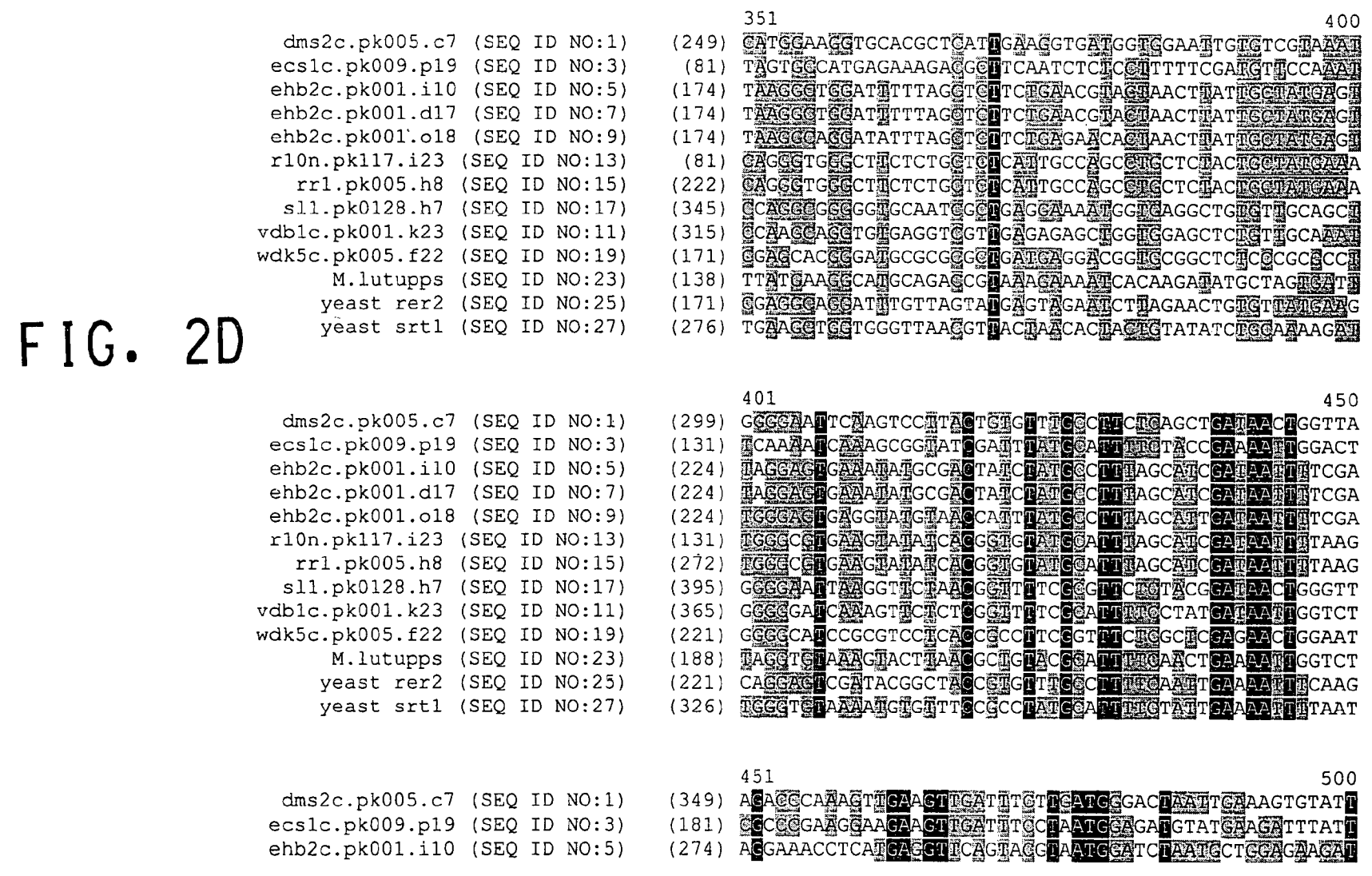
Figure 2E:
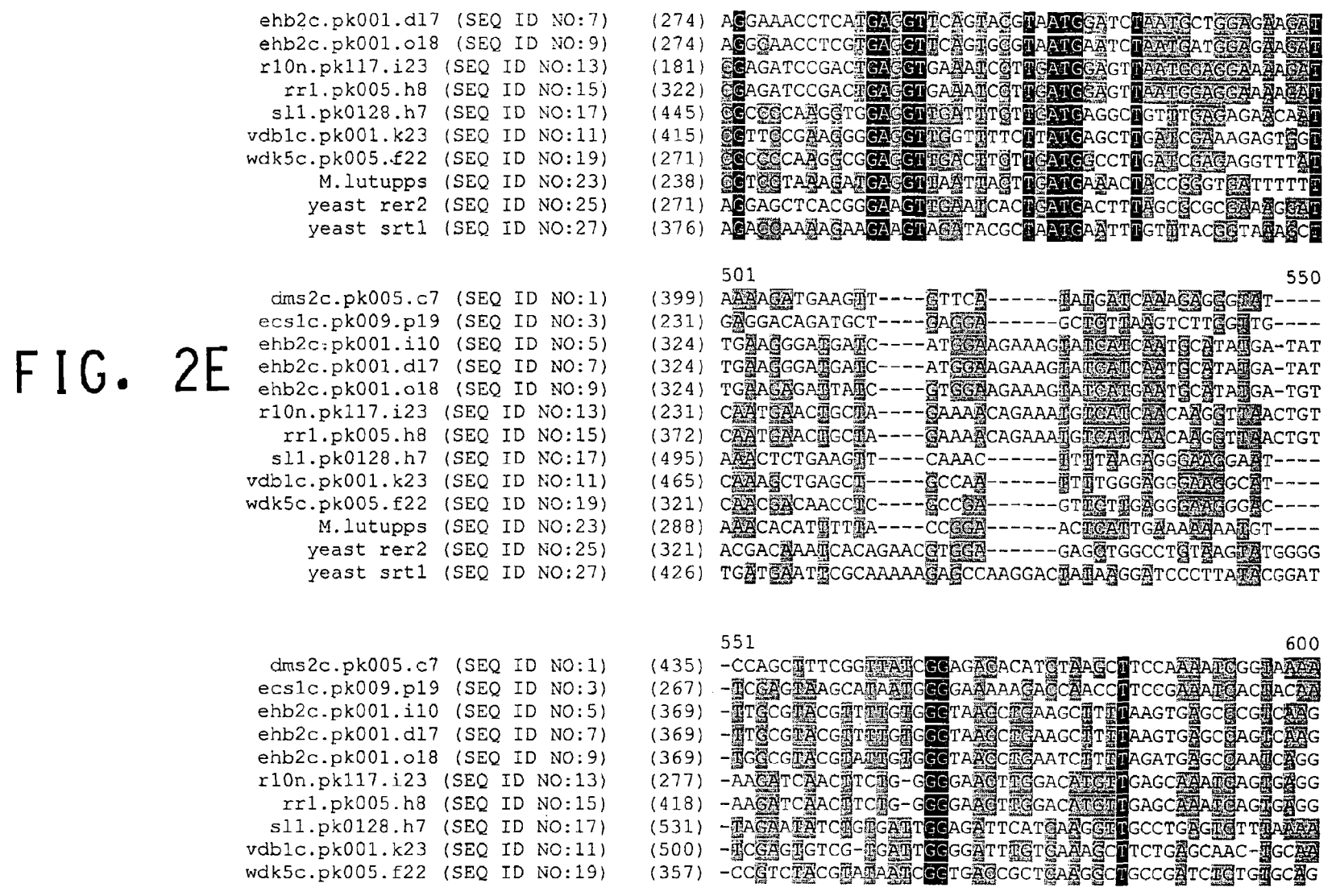
Figure 2F:
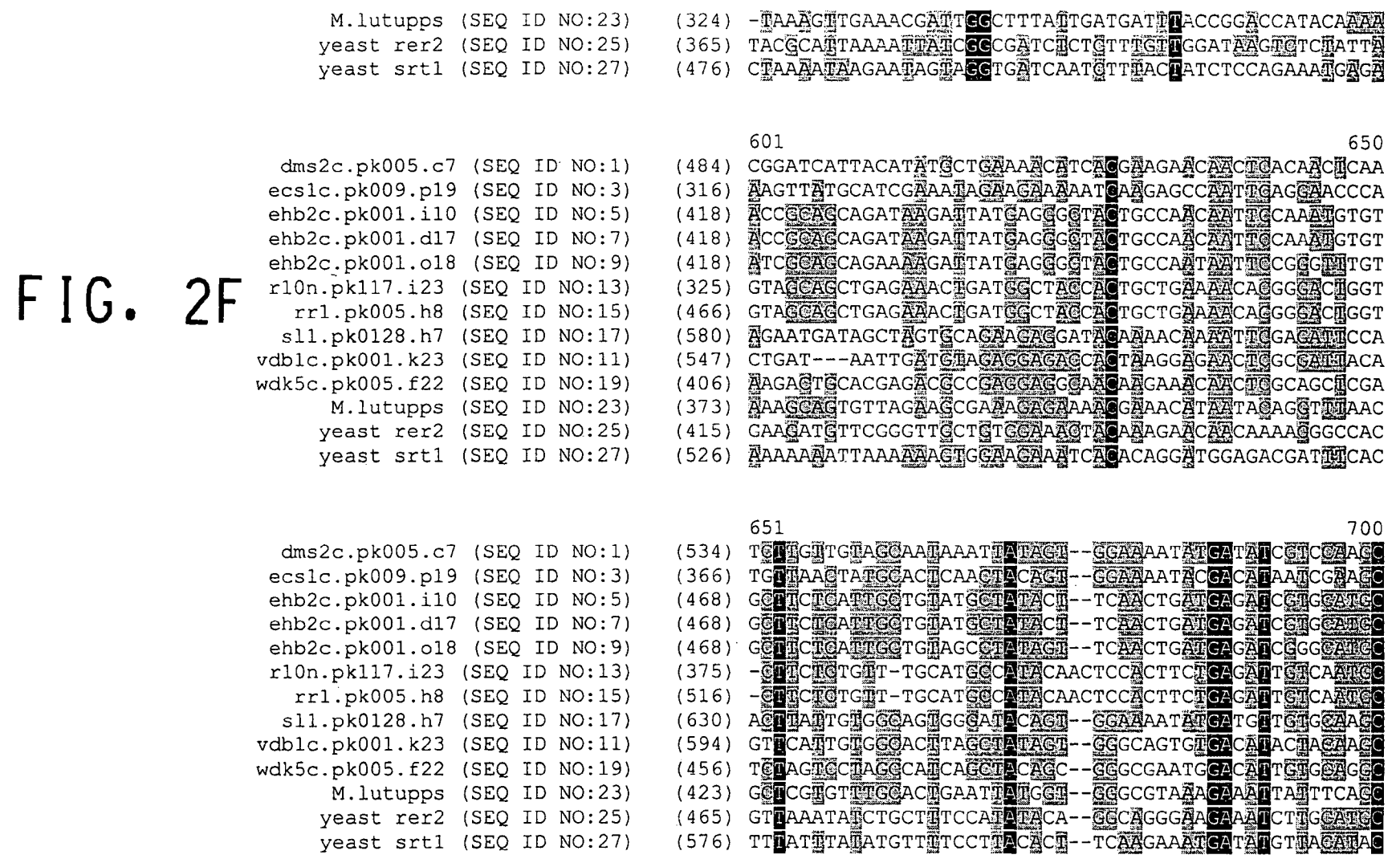
Figure 2G:
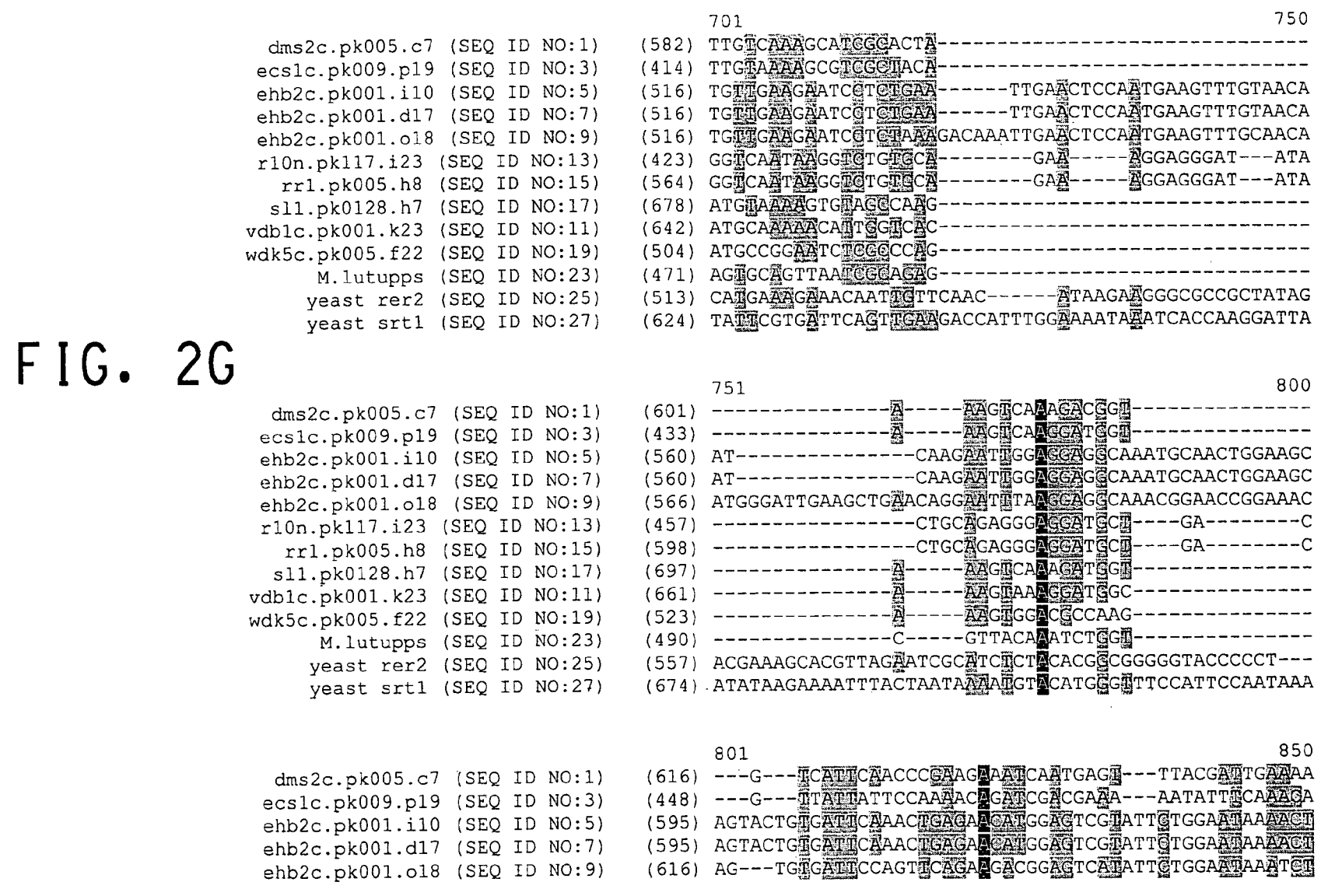
Figure 2H:
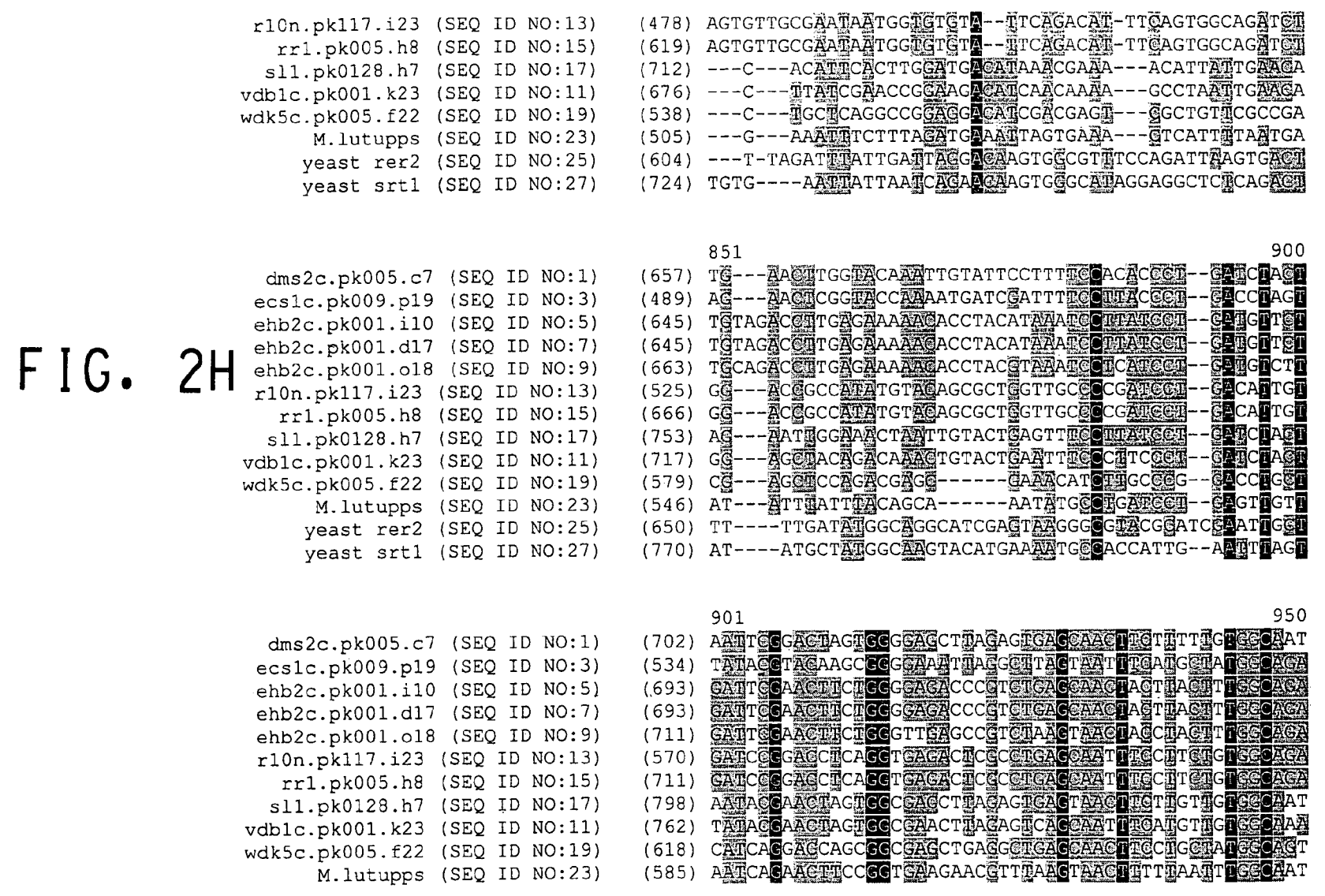

FIG. 2A thru 2J shows an alignment of coding regions of cDNAs encoding homologs of bacterial undecaprenyl phosphate synthases from different plant species with those of a bacterial (*Micrococcus luteus*) and two yeast (rer2, srt1) genes.

FIG. 3A thru 3C shows an alignment of the deduced amino acid sequences of plant cis-prenyltransferases.

FIG. 4A thru 4D shows an alignment of the proteins derived from the partial plant cDNAs shown in FIG. 2, with the deduced amino acid sequences of a bacterial (*Micrococcus luteus*) and two yeast (rer2, srt1) genes.

Figure 1:
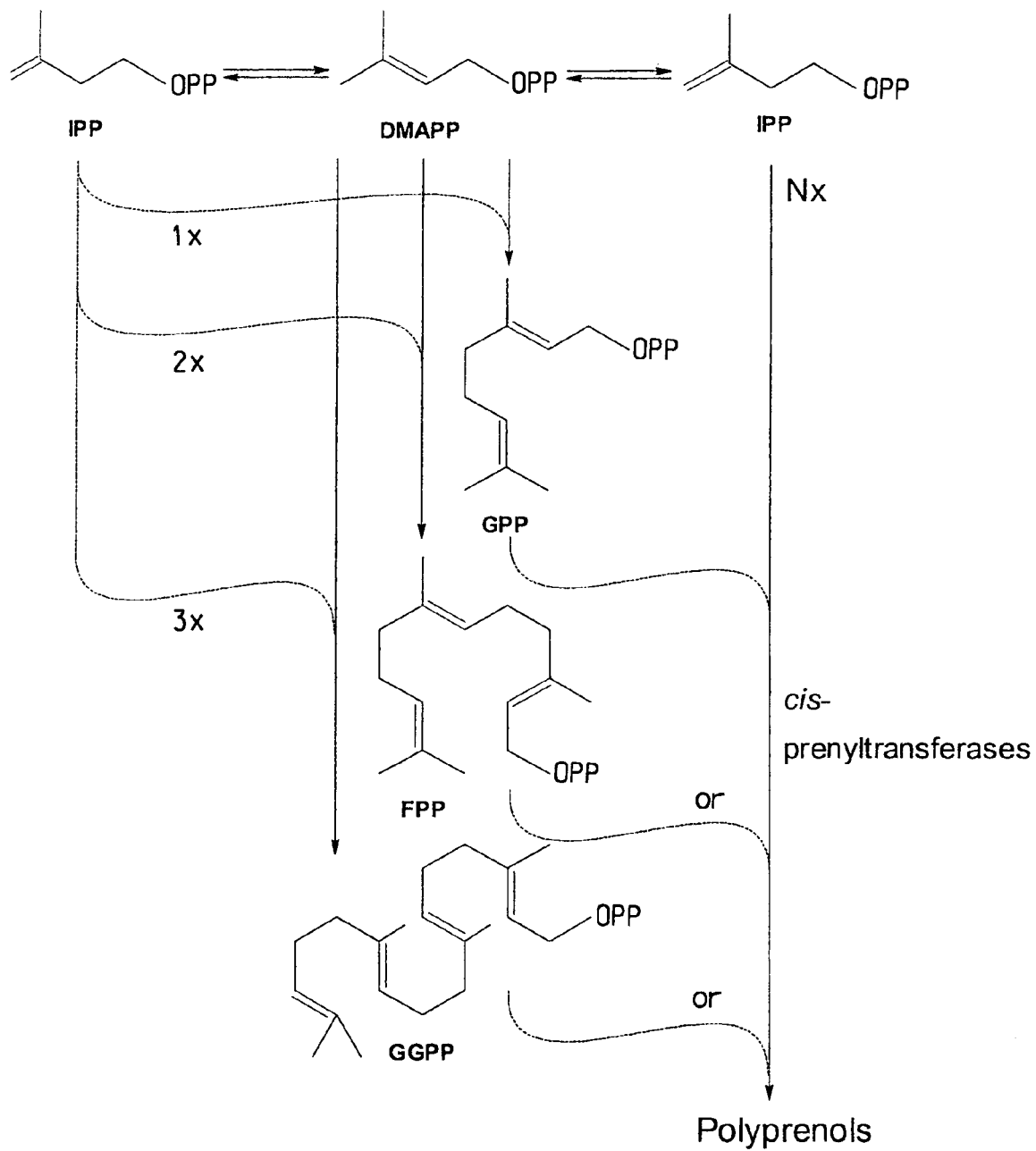

The invention can be more fully understood from the following detailed description and the accompanying sequence descriptions which form part of this application.

The following sequence descriptions and sequences listings attached hereto comply with the rules governing nucleotide and/or amino acid sequence disclosures in patent applications as set forth in 37 C.F.R. §1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administration Instructions). The Sequence Descriptions contain the one letter code for nucleotide sequence characters and the three letter codes for amino acids as defined in conformity with the IUPAC-IYUB standards described in *Nucleic Acids Res.* 13:3021-3030 (1985) and in the *Biochemical Journal* 219:345-373 (1984) which are herein incorporated by reference.

SEQ ID NO:1 is the nucleotide sequence for the African daisy clone dms2c.pk005.c7.

SEQ ID NO:2 is the deduced amino acid sequence for the African daisy dms2c.pk005.c7, encoded by SEQ ID NO: 1.

SEQ ID NO:3 is the nucleotide sequence for the Pot Marigold clone ecslc.pk009.p19.

SEQ ID NO:4 is the deduced amino acid sequence for the Pot Marigold clone ecslc.pk009.p19, encoded by SEQ ID NO:3.

SEQ ID NO:5 is the nucleotide sequence for the *Hevea* clone ehb2c.pk001.i10.

SEQ ID NO:6 is the deduced amino acid sequence for the *Hevea* clone ehb2c.pk001.i10, encoded by SEQ ID NO:5.

SEQ ID NO:7 is the nucleotide sequence for the *Hevea* clone ehb2c.pk001.d17.

SEQ ID NO:8 is the deduced amino acid sequence for the *Hevea* clone ehb2c.pk001.d17, encoded by SEQ ID NO:7.

SEQ ID NO:9 is the nucleotide sequence for the *Hevea* clone ehb2c.pk001.o18.

SEQ ID NO:10 is the deduced amino acid sequence for the *Hevea* clone ehb2c.pk001.o18, encoded by SEQ ID NO:9.

SEQ ID NO:11 is the nucleotide sequence for the grape clone vdblc.pk001.k23.

SEQ ID NO:12 is the deduced amino acid sequence for the grape clone vdb1c.pk001.k23, encoded by SEQ ID NO:11.

SEQ ID NO:13 is the nucleotide sequence for the rice clone r10n.pk117.i23.

SEQ ID NO:14 is the deduced amino acid sequence for the rice clone r10n.pk117.i23, encoded by SEQ ID NO:13.

SEQ ID NO:15: is the nucleotide sequence for clone the rice clone rr1.pk0050.h8.

SEQ ID NO:16 is the deduced amino acid sequence for rr1.pk0050.h8, encoded by SEQ ID NO:15.

SEQ ID NO:17 is the nucleotide sequence for the soybean clone sl1.pk0128.h7.

SEQ ID NO:18 is the deduced amino acid sequence for the soybean clone sl1.pk0128.h7, encoded by SEQ ID NO:17.

SEQ ID NO:19 is the nucleotide sequence for the wheat clone wdk5c.pk005.f22.

SEQ ID NO:20 is the deduced amino acid sequence for the wheat clone wdk5c.pk005.f22, encoded by SEQ ID NO:19.

SEQ ID NO:21 is the conserved Domain I.
SEQ ID NO:22 is the conserved Domain V.
SEQ ID NO:23 is the nucleotide sequence encoding a bacterial undecaprenyl phosphate synthase isolated from *Micrococcus luteus*.

SEQ ID NO:24 is the deduced amino acid sequence of a bacterial undecaprenyl phosphate synthase isolated from *Micrococcus luteus*.

SEQ ID NO:25 is the nucleotide sequence encoding a yeast undecaprenyl phosphate synthase isolated from the yeast strain rer2.

SEQ ID NO:26 is the deduced amino acid sequence of a yeast undecaprenyl phosphate synthase isolated from the yeast strain rer2.

SEQ ID NO:27 is the nucleotide sequence encoding a yeast undecaprenyl phosphate synthase isolated from the yeast strain srt1.

SEQ ID NO:28 is the deduced amino acid sequence of a yeast undecaprenyl phosphate synthase isolated from the yeast strain srt1.

SEQ ID NOs 29-36 are primers used for the transformation of arabidopsis with various cis-prenyltransferases genes.

SEQ ID NO:37 is the nucleotide sequence of the Apt5 arabidopsis cis-prenyl transferase homolog.

DETAILED DESCRIPTION OF THE INVENTION

The present invention reports the isolation and characterization of cDNAs corresponding to genes homologous with microbial cis-prenyltransferases as ESTs from wheat, grape, soybean, rice, African daisy, rubber and marigold. No such homologs have been described previously in these species. The level of expression of the genes described here can be altered in the plant by methods of cosuppression and overexpression. As they are previously undescribed genes involved in synthesizing a family of molecules with fundamental cellular roles as well as roles in plant defense, this can lead to novel phenotypes that are expected to be beneficial for crop protection, production or as industrial sources of polyisoprenoids. In addition, if the reduction in expression of one of the genes leads to a growth or developmental defect in the plant, this gene can be used as a novel herbicide target. All isolated proteins can be used as tools to study the elaboration of polymeric cis-isoprenoids by plants. This can lead to the identification of additional proteins that can be used as described above. Any related EST sequences can be directly used for the above described applications in crop plants.

The following definitions are provided for the full-understanding of terms and abbreviations used in this specification:

"Polymerase chain reaction" is abbreviated PCR
"Expressed sequence tag" is abbreviated EST
"Open reading frame" is abbreviated ORF
"SDS polyacrylamide gel electrophoresis" is abbreviated SDS-PAGE
"UPPS" is the abbreviation for the specific undecaprenyl diphosphate synthases isolated from bacteria.
"OPPS" is the abbreviation for the specific octaprenyl diphosphate synthases isolated from bacteria.
"Dedol-PP" is dehydrodolichol diphosphate
"DMAPP" is dimethyl allyl diphosphate
"IPP" is isopentenyl diphosphate
"GPP" is geranyl diphosphate
"FPP" is farnesyl diphosphate
"GGPP" is geranylgeranyl diphosphate.

The term "cis-prenyltransferase" refers generally to a class of enzymes capable of catalyzing the sequential addition of $C_5$ units to polyprenols and rubbers. Two examples of cis-prenyltransferases are the undecaprenyl diphosphate and dehydrodolichyl diphosphate synthases.

The terms "isolated nucleic acid fragment" or "isolated nucleic acid molecule" refer to a polymer of RNA or DNA that is single- or double-stranded, optionally containing synthetic, non-natural or altered nucleotide bases. An isolated nucleic acid fragment or an isolated nucleic acid molecule in the form of a polymer of DNA may be comprised of one or more segments of cDNA, genomic DNA, or synthetic DNA.

The terms "host cell" and "host organism" refer to a cell capable of receiving foreign or heterologous genes and expressing those genes to produce an active gene product. Suitable host cells include microorganisms such as bacteria and fungi, as well as plant cells.

The term "plant defense response" refers to the ability of a plant to deter tissue damage by insects, pathogens such as fungi, bacteria or viruses, as well as herbivores.

The term "fragment" refers to a DNA or amino acid sequence comprising a subsequence of the nucleic acid sequence or protein of the present invention. However, an active fragment of the present invention comprises a sufficient portion of the protein to maintain activity.

As used herein, "substantially similar" refers to nucleic acid fragments wherein changes in one or more nucleotide bases result in substitution of one or more amino acids, but do not affect the functional properties of the protein encoded by the DNA sequence. "Substantially similar" also refers to nucleic acid fragments wherein changes in one or more nucleotide bases do not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotide bases that do not substantially affect the functional properties of the resulting transcript vis-à-vis the ability to mediate alteration of gene expression by antisense or co-suppression technology or alteration of the functional properties of the resulting protein molecule. It is therefore understood that the invention encompasses more than the specific exemplary sequences.

For example, it is well known in the art that antisense suppression and co-suppression of gene expression may be accomplished using nucleic acid fragments representing less that the entire coding region of a gene, and by nucleic acid fragments that do not share 100% identity with the gene to be suppressed. Moreover, alterations in a gene which result in the production of a chemically equivalent amino acid at a given site, but do not effect the functional properties of the encoded protein, are well known in the art. Thus, a codon for the amino acid alanine, a hydrophobic amino acid, may be substituted by a codon encoding another less hydrophobic residue (such as glycine) or a more hydrophobic residue (such as valine, leucine, or isoleucine). Similarly, changes which result in substitution of one negatively charged residue for another (such as aspartic acid for glutamic acid) or one positively charged residue for another (such as lysine for arginine) can also be expected to produce a functionally equivalent product. Nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products. Moreover, the skilled artisan recognizes that substantially similar sequences encompassed by this invention are also defined by their ability to hybridize, under stringent conditions (0.1×SSC, 0.1% SDS, 65° C.), with the sequences exemplified herein. Preferred substantially similar nucleic acid fragments of the instant invention are those nucleic acid fragments whose DNA sequences are at least 80% identical to the DNA sequence of the nucleic acid fragments reported herein. More preferred nucleic acid fragments are at least 90% identical to the identical to the DNA sequence of the nucleic acid fragments reported herein. Most preferred are nucleic acid fragments that are at least 95% identical to the DNA sequence of the nucleic acid fragments reported herein.

A "substantial portion" of an amino acid or nucleotide sequence comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215:403-410; see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12-15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches partial or complete amino acid and nucleotide sequences encoding one or more particular fungal proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol.* 215:403-410 (1990), Vector NTI (InforMax Inc. 6110 Executive Boulevard, Suite 400, North Bethesda, Md.) and DNASTAR (DNASTAR Inc. 1228 S. Park Street, Madison, Wis.). Within the context of this application it will be understood that where sequence analysis software is used for analysis, that the results of the analysis will be based on the "default values" of the program referenced, unless otherwise specified. As used herein "default vales" will mean any set of values or parameters which originally load with the software when first initialized. The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, New York (1988); *Biocomputinp: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS.* 5:151-153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids. "Codon degeneracy" refers to divergence in the genetic code permitting variation of the nucleotide sequence without effecting the amino acid sequence of an encoded polypeptide. Accordingly, the present invention relates to any nucleic acid fragment that encodes all or a substantial portion of present proteins as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18 and SEQ ID NO:20. The skilled artisan is well aware of the "codon-bias" exhibited by a specific host cell to use nucleotide codons to specify a given amino acid. Therefore, when synthesizing a gene for improved expression in a host cell, it is desirable to design the gene such that its frequency of codon usage approaches the frequency of preferred codon usage of the host cell.

The term "complementary" is used to describe the relationship between nucleotide bases that are hybridizable to one another. Hence with respect to DNA, adenosine is complementary to thymine and cytosine is complementary to guanine.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). In one embodiment the length for a hybridizable nucleic acid is at least about 10 nucleotides. Preferable a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe. "Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determining preferred codons can be based on a survey of genes derived from the host cell where sequence information is available. "Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene, not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but which is introduced into the host organism by gene transfer. Foreign genes can comprise native genes inserted into a non-native organism, or chimeric genes. A "transgene" is a gene that has been introduced into the genome by a transformation procedure. "Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns and polyadenylation recognition sequences. "Promoter" refers to a DNA sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, (*Biochem. Plants* 15:1-82 (1989)). It is further recognized that since in most cases the exact boundaries of regulatory sequences have not been completely defined, DNA fragments of different lengths may have identical promoter activity.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner et al., *Mol. Biotech.* 3:225 (1995)).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (*Plant Cell* 1:671-680 (1989)). "RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA" (mRNA) refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns or the coding sequence. "Functional RNA" refers to antisense RNA, ribozyme RNA or other RNA that is not translated yet has an effect on cellular processes.

The term "operably-linked" refers to the association of nucleic acid sequences on a single nucleic acid fragment so that the function of one is affected by the other. For example, a promoter is operably-linked with a coding sequence when it affects the expression of that coding sequence (i.e., that the coding sequence is under the transcriptional control of the promoter). Coding sequences can be operably-linked to regulatory sequences in sense or antisense orientation.

The term "expression" refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020).

"Altered levels" refers to the production of gene product(s) in organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels, J. J., *Ann. Rev. Plant Phys. Plant Mol. Biol.* 42:21-53 (1991)). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel et al., *Plant Phys.* 100:1627-1632 (1992)).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include *Agrobacterium*-mediated transformation (De Blaere et al., *Meth. Enzymol.* 143:277 (1987)) and particle-accelerated or "gene gun" transformation technology (Klein et al., *Nature, London* 327:70-73 (1987); U.S. Pat. No. 4,945,050).

Standard recombinant DNA and molecular cloning techniques used herein are well known in the art and are described more fully in Sambrook, J., Fritsch, E. F. and Maniatis, T. *Molecular Cloning: A Laboratory Manual; Cold Spring Harbor Laboratory Press: Cold Spring Harbor,* 1989 (hereinafter "Sambrook et al.").

Unique plant homologs of microbial cis-prenyltransferase proteins, involved in the synthesis of poly-cis-isoprenoids, have been isolated from wheat, grape, soybean, rice, African daisy, rubber and marigold. Comparison of their random cDNA sequences to the GenBank database using the BLAST algorithm, well known to those skilled in the art, revealed that these proteins have no significant homologies to other identified proteins in plants. The nucleotide sequences of the present homolog cDNAs are provided in SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17 and SEQ ID NO:19. Other poly-cis-isoprenoid synthase genes and proteins from other plants can now be identified by comparison of random cDNA sequences to the present cis-prenyltransferase sequences provided herein.

The present sequences were identified by comparison to public as well as internal database. Strong correlation was seen between the instant sequences and the cis-prenyltransferase genes and proteins isolated from *Micrococcus luteus* Shimizu, N., Koyama, T. and Ogura, K., *J. Biol. Chem.* 273:19476-19481 (1998)) and *Saccharomyces cerevisiae*. Accordingly it is an object of the present invention to provide nucleic acid molecules encoding plant cis-prenyltransferase proteins where the nucleic acid sequence is at least 50% identical to the bacterial undecaprenyl diphosphate synthase gene isolated from *Micrococcus luteus* where a correlation of at least 80% is preferred. Similarly the invention provides plant cis-prenyltransferase proteins where the amino acid sequence is at least 41% identical to the bacterial undecaprenyl diphosphate synthase protein isolated from *Micrococcus luteus* where a correlation of at least 70% is preferred.

The nucleic acid fragments of the present invention may be used to isolate cDNAs and genes encoding a homologous prenyltransferases from the same or other plant species. Isolating homologous genes using sequence-dependent protocols is well known in the art. Examples of sequence-dependent protocols include, but are not limited to, methods of nucleic acid hybridization and methods of DNA and RNA amplification as exemplified by various uses of nucleic acid amplification technologies (e.g., polymerase chain reaction (PCR) or ligase chain reaction).

For example, other cis-prenyltransferase genes, (and particularly undecaprenyl diphosphate and dehydrodolichyl diphosphate synthases) either as cDNAs or genomic DNAs, could be isolated directly by using all or a portion of the present nucleic acid fragments as DNA hybridization probes to screen libraries from any desired plant using methodology well known to those skilled in the art. Specific oligonucleotide probes based upon the present cis-prenyltransferase sequences can be designed and synthesized by methods known in the art (Sambrook et al., supra). Moreover, the entire sequences can be used directly to synthesize DNA probes by methods known to the skilled artisan such as random primers, DNA labeling, nick translation, or end-labeling techniques, or RNA probes using available in vitro transcription systems. In addition, specific primers can be designed and used to amplify a part of or full-length of the present sequences. The resulting amplification products can be labeled directly during amplification reactions or labeled after amplification reactions, and used as probes to isolate full length cDNA or genomic fragments under conditions of appropriate stringency.

In addition, two short segments of the present nucleic acid fragment may be used in PCR protocols to amplify longer nucleic acid fragments encoding homologous genes from DNA or RNA. The polymerase chain reaction may also be performed on a library of cloned nucleic acid fragments wherein the sequence of one primer is derived from the present nucleic acid fragments, and the sequence of the other primer takes advantage of the presence of the polyadenylic acid tracts to the 3' end of the mRNA precursor encoding plant UPPS homologs.

Alternatively, the second primer sequence may be based upon sequences derived from the cloning vector. For example, the skilled artisan can follow the RACE protocol (Frohman et al., *Proc. Natl. Acad. Sci. USA* 85:8998 (1988)) to generate cDNAs by using PCR to amplify copies of the region between a single point in the transcript and the 3' or 5' end. Primers oriented in the 3' and 5' directions can be designed from the present sequences. Using commercially available 3' RACE or 5' RACE systems (BRL), specific 3' or 5' cDNA fragments can be isolated (Ohara et al., *Proc. Natl. Acad. Sci., USA* 86:5673 (1989); Loh et al., *Science* 243:217 (1989)). Products generated by the 3' and 5' RACE procedures can be combined to generate full-length cDNAs (Frohman et al., *Techniques* 1:165 (1989)).

Finally, availability of the present nucleotide and deduced amino acid sequences facilitates immunological screening of cDNA expression libraries. Synthetic peptides representing portions of the present amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner et al., *Adv. Immunol.* 36:1 (1984); Sambrook et al., supra).

The nucleic acid fragments of the present invention may also be used to create transgenic plants in which the present cis-prenyltransferase protein is present at higher or lower levels than normal. Alternatively, in some applications, it might be desirable to express the present cis-prenyltransferase protein in specific plant tissues and/or cell types, or during developmental stages in which they would normally not be encountered. The expression of full-length plant cis-prenyltransferase cDNAs (ie., any of the sequences below or related sequences incorporating an appropriate in-frame ATG start codon) in a bacterial (e.g., *E. coli*), yeast (eg, *Saccharomyces cerevisiae*, *Pichia pastoralis*) or plant yields a mature protein capable of the synthesis of cis-polyisoprenoids from substrate IPP. The presence of an initiator allylic isoprenoid diphosphate (DMAPP, GPP, FPP or GGPP) enhances this activity.

It is contemplated that transgenic plants expressing the present cis-prenyltransferase sequences will have altered or modulated defense mechanisms against various pathogens and natural predators. For example, various latex proteins are known to be antigenic and recognized by IgE antibodies, suggesting their role in immunolgical defense (Yagami et al., *Journal of Allergy and Clinical Immunology*, (March, 1998) Vol. 101, No. 3, pp. 379-385. Additionally it has been shown that a significant portion of the latex isolated from *Hevea brasiliensis* contains chitinases/lysozymes, which are capable of degrading the chitin component of fungal cell walls and the peptidoglycan component of bacterial cell walls (Martin, M. N., *Plant Physiol* (Bethesda), (1991) 95 (2), 469-476). It is therefore an object of the present invention to provide transgenic plants having altered, modulated or increased defenses towards various pathogens and herbivores.

The plant species suitable for expression of the present sequences may be (but are not limited to) tobacco (*Nicotiana* spp.), tomato (*Lycopersicon* spp.), potato (*Solanum* spp.), hemp (*Cannabis* spp.), sunflower (*Helianthus* spp.), sorghum (*Sorghum vulgare*), wheat (*Triticum* spp.), maize (*Zea mays*), rice (*Oryza sativa*), rye (*Secale cereale*), oats (*Avena* spp.), barley (*Hordeum vulgare*), rapeseed (*Brassica* spp.), broad bean (*Vicia faba*), french bean (*Phaseolus vulgaris*), other bean species (*Vigna* spp.), lentil (*Lens culinaris*), soybean (*Glycine max*), arabidopsis (*Arabidopsis thaliana*), guayule (*Parthenium argentatum*), cotton (*Gossypium hirsutum*), petunia (*Petunia hybrida*), flax (*Linum usitatissimum*) and carrot (*Daucus carota sativa*).

Various methods of transforming cells of higher plants according to the present invention are available to those skilled in the art (see EPO Pub. 0 295 959 A2 and 0 318 341 A1). Such methods include those based on transformation vectors utilizing the Ti and R1 plasmids of *Agrobacterium* spp. It is particularly preferred to use the binary type of these vectors. Ti-derived vectors transform a wide variety of higher plants, including monocotyledonous and dicotyledonous plants (Sukhapinda et al., *Plant Mol. Biol.* 8:209-216 (1987); Potrykus et al., *Mol. Gen. Genet.* 199:183 (1985)). Other transformation methods are available to those skilled in the art, such as direct uptake of foreign DNA constructs (see EPO Pub. 0 295 959 A2), techniques of electroporation (From et al., *Nature* (London) 319:791 (1986)) or high-velocity ballistic bombardment with metal particles coated with the nucleic acid constructs (Kline et al., *Nature* (London) 327:70 (1987)). Once transformed, the cells can be regenerated by those skilled in the art.

Of particular relevance are the recently described methods to transform foreign genes into commercially important crops, such as rapeseed (De Block et al., *Plant Physiol.* 91:694-701 (1989)), sunflower (Everett et al., *Bio/Technology* 5:1201 (1987)), and soybean (Christou et al., *Proc. Natl. Acad. Sci. USA* 86:7500-7504 (1989)).

Overexpression of the present cis-prenyltransferase homologs may be accomplished by first constructing a chimeric gene in which their coding region is operably-linked to a promoter-capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals must also be provided. The present chimeric genes may also comprise one or more introns in order to facilitate gene expression.

Plasmid vectors comprising the present chimeric genes can then be constructed. The choice of a plasmid vector depends upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., *EMBO J.* 4:2411-2418 (1985); De Almeida et al., *Mol. Gen. Genetics* 218:78-86 (1989)), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the cis-prenyltransferase protein to different cellular compartments or to facilitate their secretion from the cell. The chimeric genes described above may be further modified by the addition of appropriate intracellular or extracellular targeting sequence to their coding regions. These include chloroplast transit peptides (Keegstra et al., *Cell* 56:247-253 (1989)), signal sequences that direct proteins to the endoplasmic reticulum (Chrispeels et al., *Ann. Rev. Plant Phys. Plant Mol.* 42:21-53 (1991)), and nuclear localization signal (Raikhel et al., *Plant Phys.* 100: 1627-1632 (1992)). While the references cited give examples of each of these, the list is not exhaustive and more targeting signals of utility may be discovered in the future.

It may also be desirable to reduce or eliminate expression of the cis-prenyltransferase genes in plants for some applications. In order to accomplish this, chimeric genes designed for antisense or co-suppression of cis-prenyltransferase homologs can be constructed by linking the genes or gene fragments encoding parts of these enzymes to plant promoter sequences. Thus, chimeric genes designed to express antisense RNA for all or part of a UPPS homolog can be constructed by linking the cis-prenyltransferase homolog genes or gene fragments in reverse orientation to plant promoter sequences. The co-suppression or antisense chimeric gene constructs could be introduced into plants via well known transformation protocols wherein expression of the corresponding endogenous genes are reduced or eliminated.

The present cis-prenyltransferase homolog proteins may be produced in heterologous host cells, particularly in the cells of microbial hosts, and can be used to prepare antibodies to the proteins by methods well known to those skilled in the art. The antibodies would be useful for detecting the present cis-prenyltransferase proteins in situ in cells or in vitro in cell extracts. Preferred heterologous host cells for production of the present cis-prenyltransferase proteins are microbial hosts. Microbial expression systems and expression vectors containing regulatory sequences that direct high level expression of foreign proteins are well known to those skilled in the art. Any of these could be used to construct a chimeric gene for production of the present cis-prenyltransferase homologs. This chimeric gene could then be introduced into appropriate microorganisms via transformation to provide high level expression of the present cis-prenyltransferase proteins.

Microbial host cells suitable for the expression of the present cis-prenyltransferase proteins include any cell capable of expression of the chimeric genes encoding these proteins. Such cells will include both bacteria and fungi including, for example, the yeasts (e.g., *Aspergillus, Saccharomyces, Pichia, Candida* and *Hansenula*), members of the genus *Bacillus* as well as the enteric bacteria (e.g., *Escherichia, Salmonella* and *Shigella*). Methods for the transformation of such hosts and the expression of foreign proteins are well known in the art and examples of suitable protocols may be found In *Manual of Methods for General Bacteriology*; Gerhardt et al., Eds.; American Society for Microbiology: Washington, D.C., 1994 or In *Biotechnology: A Textbook of Industrial Microbiology*, 2nd Edition, Brock, T. D., Ed.; Sinauer Associates, Inc.: Sunderland, Mass., 1989.

Vectors or cassettes useful for transforming suitable microbial host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although such control regions need not be derived from the genes native to the specific species chosen as a production host.

Initiation control regions or promoters useful to drive expression of the genes encoding the cis-prenyltransferase proteins in the desired host cell are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, trp, $IP_L$, $IP_R$, T7, tac, and trc (useful for expression in *E. coli*). Termination control regions may also be derived from various genes native to the preferred hosts. Optionally, a termination site may be unnecessary; however, it is most preferred if included.

Additionally, the present cis-prenyltransferase proteins can be used as targets to facilitate the design and/or identification of inhibitors of cis-prenyltransferase homologs that may be useful as herbicides or fungicides. This could be achieved either through the rational design and synthesis of potent functional inhibitors that result from structural and/or mechanistic information that is derived from the purified present plant proteins, or through random in vitro screening of chemical libraries. It is anticipated that significant in vivo inhibition of any of the cis-prenyltransferase homolog proteins described herein may severely cripple cellular metabolism and likely result in plant (or fungal) death.

All or a portion of the nucleic acid fragments of the present invention may also be used as probes for genetically and physically mapping the genes that they are a part of, and as markers for traits linked to expression of the present cis-prenyltransferase homologs. Such information may be useful in plant breeding in order to develop lines with desired phenotypes. For example, the present nucleic acid fragments may be used as restriction fragment length polymorphism (RFLP) markers. Southern blots (Sambrook et al., supra) of restriction-digested plant genomic DNA may be probed with the nucleic acid fragments of the present invention. The resulting banding patterns may then be subjected to genetic analyses using computer programs such as MapMaker (Lander et al., *Genomics* 1:174-181 (1987)) in order to construct a genetic map. In addition, the nucleic acid fragments of the present invention may be used to probe Southern blots containing restriction endonuclease-treated genomic DNAs of a set of individuals representing parent and progeny of a defined genetic cross. Segregation of the DNA polymorphisms is noted and used to calculate the position of the present nucleic acid sequence in the genetic map previously obtained using this population (Botstein et al., *Am. J. Hum. Genet.* 32:314-331 (1980)).

The production and use of plant gene-derived probes for use in genetic mapping is described by Bernatzky et al. (*Plant Mol. Biol. Reporter* 4:37-41 (1986)). Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the present nucleic acid sequences may also be used for physical mapping (i.e., placement of sequences on physical maps; see Hoheisel et al., *Nonmammalian Genomic Analysis: A Practical Guide*; Academic Press, 1996; pp. 319-346 and references cited therein).

In another embodiment, nucleic acid probes derived from the present nucleic acid sequence may be used in direct fluorescence in situ hybridization (FISH) mapping. Although current methods of FISH mapping favor use of large clones (several to several hundred kb), improvements in sensitivity may allow performance of FISH mapping using shorter probes.

A variety of nucleic acid amplification-based methods of genetic and physical mapping may be carried out using the present nucleic acid sequences. Examples include allele-specific amplification (Kazazian et al., *J. Lab. Clin. Med.* 114:95-96 (1989)), polymorphism of PCR-amplified fragments (CAPS; Sheffield et al., *Genomics* 16:325-332 (1993)), allele-specific ligation (Landegren et al., *Science* 241:1077-1080 (1988)), nucleotide extension reactions (Sokolov et al., *Nucleic Acid Res.* 18:3671 (1990)), Radiation Hybrid Mapping (Walter et al., *Nature Genetics* 7:22-28 (1997)) and Happy Mapping (Dear et al., *Nucleic Acid Res.* 17:6795-6807 (1989)). For these methods, the sequence of a nucleic acid fragment is used to design and produce primer pairs for use in the amplification reaction or in primer extension reactions. The design of such primers is well known to those skilled in the art. In methods using PCR-based genetic mapping, it may be necessary to identify DNA sequence differences between the parents of the mapping cross in the region corresponding to the present nucleic acid sequence. This, however, is generally not necessary for mapping methods.

Loss of function-mutant phenotypes may be identified for the present cDNA clones either by targeted gene disruption protocols or by identifying specific mutants for these genes contained in a population of plants carrying mutations in all possible genes (e.g., Ballinger et al., *Proc. Natl. Acad. Sci. USA* 86:9402 (1989); Koes et al., *Proc. Natl. Acad. Sci. USA* 92:8149 (1995); Bensen et al., *Plant Cell* 7:75 (1995)). The latter approach may be accomplished in two ways. First, short segments of the present nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the cis-prenyltransferase protein. Alternatively, the present nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a-plant containing a mutation in the endogenous gene encoding a cis-prenyltransferase protein can be identified and obtained. This mutant plant can then be used to determine or confirm the natural function of the cis-prenyltransferase gene product.

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usage and conditions.

EXAMPLES

General Methods

Standard recombinant DNA and molecular cloning techniques used here are well known in the art and are described by Sambrook et al., *Molecular Cloning: A Laboratory Manual*, $2^{nd}$ Edition, Cold Spring Harbor Laboratory Press, Cold Spring Harbor (1989) (hereinafter "Sambrook et al."); and by T. J. Silhavy, M. L. Bennan, and L. W. Enquist, *Experiments with Gene Fusions*, Cold Spring Harbor Laboratory Press, Cold Spring, N.Y. (1984) and by Ausubel et al., *Current Protocols in Molecular Biology*, pub. by Greene Publishing Assoc. and Wiley-Interscience (1987).

Nucleotide and amino acid percent identity and similarity comparisons were made using the GCG suite of programs, applying default parameters unless indicated otherwise.

The meaning of abbreviations is as follows: "sec" means second(s), "min" means minute(s), "h" means hour(s), "d" means day(s), "μL" means microliter, "mL" means milliliters, "L" means liters, "mM" means millimolar, "M" means molar, and "mmol" means millimole(s).

Example 1

Composition of cDNA Libraries Used for Identification of cDNA Clones from Plant Species Encoding cis-Prenyltransferase Homologs cDNA libraries representing mRNAs from wheat, grape, soybean, rice, African daisy, rubber tree latex and marigold tissues were prepared. The characteristics of the libraries are described in Table 1. cDNA libraries were prepared by any one of several methods. The cDNAs were introduced into plasmid vectors by first preparing the cDNA libraries in Uni-ZAP XR vectors according to the manufacturer's protocol (Stratagene Cloning Systems, La Jolla, Calif.). The Uni-ZAP XR libraries were converted into plasmid libraries according to the protocol provided by Stratagene. Upon conversion, cDNA inserts were contained in the plasmid vector pBluescript. In an alternate approach the cDNAs were introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts were in plasmid vectors, plasmid DNAs were prepared from randomly picked bacterial colonies containing recombinant pBluescript plasmids, or the insert cDNA sequences were amplified via polymerase chain reaction using primers specific for vector sequences flanking the inserted cDNA sequences. Amplified insert DNAs or plasmid DNAs were sequenced in dye-primer sequencing reactions to generate partial cDNA sequences (expressed sequence tags or "ESTs"; see Adams et al., *Science* 252: 1651-1656 (1991). The resulting ESTs were analyzed using a Perkin Elmer Model 377 fluorescent sequencer.

TABLE 1 cDNA Libraries from Plants

| Library | Species and Tissue |
| --- | --- |
| dms2c | African daisy (*Dimorphotheca sinuata*) developing seeds |
| ecs1c | pot marigold (*Calendula officinalis*) developing seeds |
| ehb2c | para rubber tree (*Hevea brasiliensis*, PR255) latex tapped in 2$^{nd}$ day of two day tapping cycle |
| Vdb1c | Grape (*Vitis* sp.) developing bud |
| r10n | rice (*Oryza sativa* L.) fifteen day leaf (normalized) |
| rr1 | rice (*Oryza sativa* L.) root of two week old developing seedling |
| sl1 | soybean (*Glycine max* L.) of two week old developing seedlings treated with water |
| wdk5c | wheat (*Triticum aestivum* L.) developing kernel, thirty days after anthesis |

Example 2

Characterization of ESTs

ESTs encoding candidate cis-prenyltransferases were identified by conducting BLAST (Basic Local Alignment Search Tool; Altschul et al., *J. Mol. Biol.* 215:403-410 (1993); see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL and DDBJ databases). The cDNA sequences obtained in Example 3 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J. *Nature Genetics* 3:266-272 (1993)) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Identification and Characterization of cDNA Clones for cis-Prenyltransferases cDNAs from the libraries listed in Table 1 were identified as cis-prenyltransferase homologs based on interrogation of the database described in Example s 1 and 2. cDNAs were thus identified by a number of methods, including the following: 1) keyword searches (e.g., "undecaprenyl"), 2) searches of the database using the TBLASTN algorithm provided by the National Center for Biotechnology Information (NCBI) and short fragments of conserved sequence present in bacterial undecaprenyl synthases, and 3) identification of further homologs of cDNAs discovered by 1 and 2 within the in-house database using the FASTA program. An alignment of the deduced amino acid sequence of the *E. coli* undecaprenyl pyrophosphate synthase gene with a number of other publicly-available sequences from bacteria, yeast (*Saccharomyces cerevisiae*) and one eukaryote (*Caenorhabditis elegans*) has been published (Apfel et al., *J. Bacteriol.* 81:483-492 (1999)). This alignment revealed five conserved domains. One of these (Domain I) is present at the 5' end of the ORFs of these genes, and consists of the following sequence: HXXMDGNXRXA (X=any amino acid; (SEQ ID NO:21)). Another (Domain V) is present towards the 3' end of the ORFs, and consists of the following sequence: DLXIRTXGEXRXSNFLLWQXXYXE (where X=any amino acid; (SEQ ID NO:22)). These sections of conserved sequence are likely to be diagnostic for the cis-prenyltransferase family of enzymes, and were used in the aforementioned TBLASTN searches.

Further homologs of cDNAs discovered by the first and second method within the in-house database were identified as sequences homologous by FASTA alignment with a specified sequence, either restricted to the same library, or across all libraries or across a library group. The cDNAs identified by these means are listed in Table 2.

TABLE 2 cDNAs Identified as cis-Prenyltransferase Homologs

| Sequence identification number (SID) | Source |
| --- | --- |
| dms2c.pk005.c7 | African Daisy |
| ecs1c.pk009.p19 | pot marigold |
| ehb2c.pk001.i10 | *Hevea brasiliensis* |
| ehb2c.pk001.d17 | *Hevea brasiliensis* |
| ehb2c.pk001.o18 | *Hevea brasiliensis* |
| Vdb1c.pk001.k23 | grape |
| r10n.pk117.i23 | rice |

TABLE 2-continued cDNAs Identified as cis-Prenyltransferase Homologs

| Sequence identification number (SID) | Source |
|---|---|
| rr1.pk0050.h8 | rice |
| sl1.pk0128.h7 | soybean |
| wdk5c.pk005.f22 | wheat |

Comparison of the nucleotide (SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17 and SEQ ID NO:19) and deduced amino acid (SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18 and SEQ ID NO:20) sequences of these ESTs with those of a representative bacterial cis-prenyltransferase (*Micrococcus luteus* UPPS; Shimizu, N., Koyama, T. and Ogura, K., *J. Biol. Chem.* 273:19476-19481 (1998)) show them to exhibit >45% identity in nucleotide sequence and >30% identity in amino acid sequence. Table 3 lists the comparison of the cis-prenyltransferase sequences isolated from wheat, grape, soybean, rice, African daisy, rubber tree and pot marigold with the sequence of the *Micrococcus luteus* UPPS. FIG. 2 shows an alignment of the nucleotide sequence within the coding regions of these cDNAs with those of *Micrococcus luteus* UPPS and two yeast cis-prenyltransferase genes, rer2 (GenBank ACC. NO. AB013497) and srt1 (GenBank ACC. NO. AB013498) which indicates the extent of homology between the primary sequence of these cis-prenyltransferase genes from diverse species.

TABLE 3

Comparison of Grape, Rice, Soybean, Rubber tree and African Daisy Sequences Against the Sequence of *Micrococcus luteus* Undecaprenyl Pyrophosphate Synthase

| cDNA/deduced protein sequence | % Identity[1] | | Similarity Identified to *M. luteus* Gene[5] | | |
|---|---|---|---|---|---|
| | NA[2] | AA[2] | BLAST algorithm | Score[3] | pLog[4] |
| dms2c.pk005.c7 | 50.13 | 39.024 | Xnr | 162 | 10.57 |
| ecs1c.pk009.p19 | 50.40 | 38.938 | | | |
| ehb2c.pk001.i10 | 46.00 | 33.603 | Xnr | 71 | 1.48 |
| ehb2c.pk001.d17 | 46.133 | 33.603 | Xnr | 161 | 10.46 |
| ehb2c.pk001.o18 | 49.464 | 32.129 | | | |
| vdb1c.pk001.o18 | 46.559 | 34.413 | | | |
| r10n.pk117.i23 | 45.652 | 33.186 | Xnr | 152 | 9.41 |
| rr1.pk0050.h8 | 45.699 | 34.694 | | | |

TABLE 3-continued

Comparison of Grape, Rice, Soybean, Rubber tree and African Daisy Sequences Against the Sequence of *Micrococcus luteus* Undecaprenyl Pyrophosphate Synthase

| cDNA/deduced protein sequence | % Identity[1] | | Similarity Identified to *M. luteus* Gene[5] | | |
|---|---|---|---|---|---|
| | NA[2] | AA[2] | BLAST algorithm | Score[3] | pLog[4] |
| sl1.pk0128.h7 | 50.133 | 41.564 | | | |
| wdk5c.pk005.f22 | 43.067 | 38.00 | | | |

[1]Comparison made using GCG GAP program, applying default values.
[2]AA is the abbreviation for amino acid sequence; NA is the abbreviation for nucleotide sequence.
[3]Score is the value assigned to a match between two sequences by the BLAST program.
[4]pLog is the negative of the logarithm of the reported P-value, the probability of observing a match of a cDNA sequence to a sequence contained in the searched databases merely by chance as calculated by BLAST.
[5]Given for those cDNAs where this similarity was detected by the initial BLAST search.

Example 4

Figure 3B:
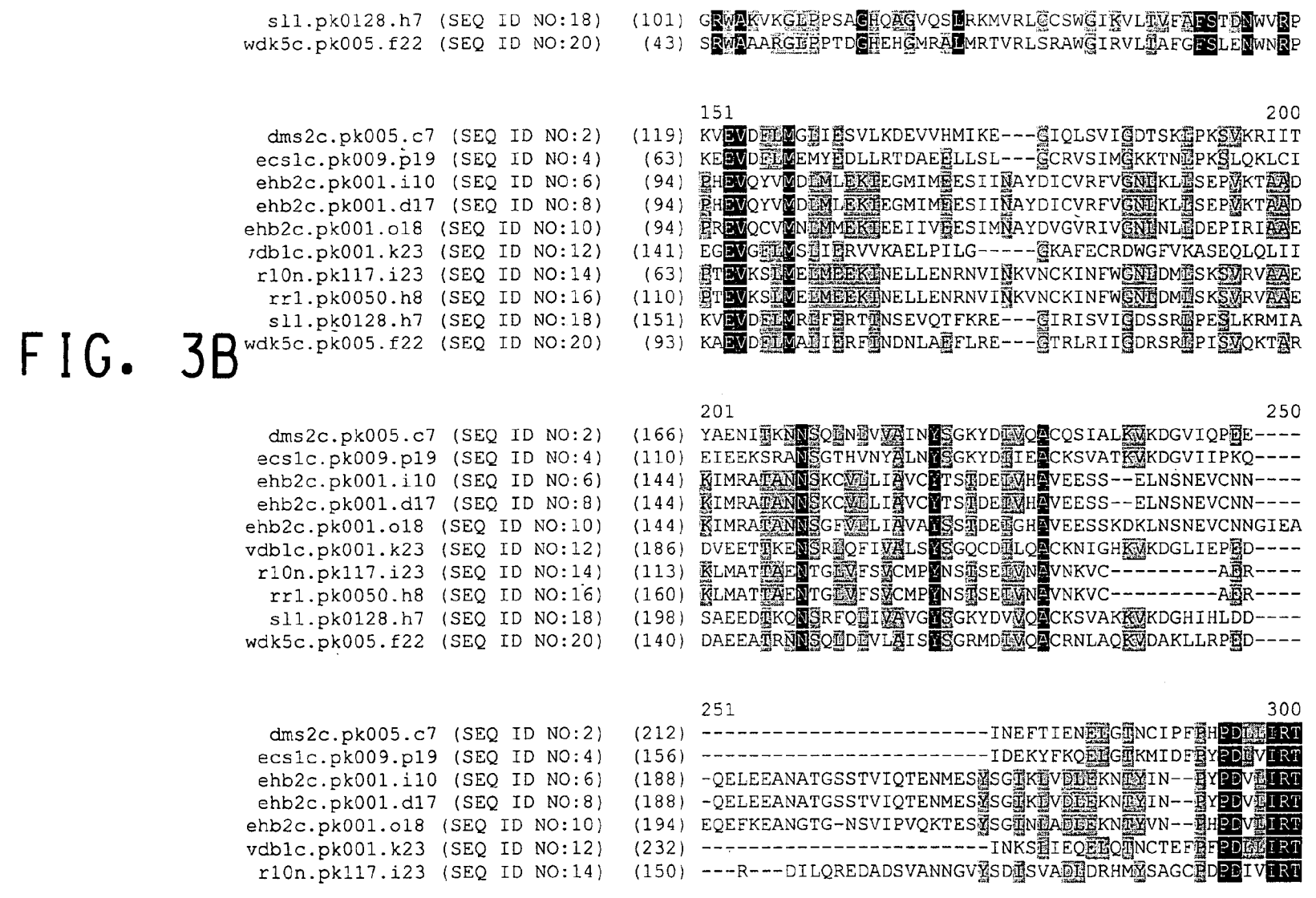

Analysis of Deduced Amino Acid Sequence of cDNAs Identified as cis-Prenyltransferase Homologs in Plants The plant cDNAs identified as described above were translated and the deduced amino acid sequences compared one to another using the GCG GAP program. Gap considers all possible alignments and gap positions between two sequences and creates a global alignment that maximizes the number of matched residues and minimizes the number and size of gaps. A scoring matrix is used to assign values for symbol matches. In addition, a gap creation penalty and a gap extension penalty are required to limit the insertion of gaps into the alignment. Gap uses the alignment method of Needleman and Wunsch (*J. Mol. Biol.* 48:443-453 (1970)). It is clear from this analysis (Table 4) that these sequences encode polypeptides with a minimum of 27.826% identity. The highest identities revealed by this analysis are between sequences from the same species, with two rice sequences exhibiting 90.668% identity and two rubber latex sequences 98.282% identity. The highest identity between sequences from different species was exhibited by the rice and grape sequences. In addition, alignment of the deduced amino acid sequence of these cDNAs together (FIG. 3) and with bacterial and yeast cis-prenyltransferases (FIG. 4) using the CLUSTALW program within the VECTOR NTI suite of programs reveals the presence of the conserved domains characteristic of this gene family (referred to in Example 2).

TABLE 4

Identity Comparison Using the GAP Program of the Deduced Amino Acid Sequences from Plant cis-Prenyltransferases

| SEQ ID | 2 | 4 | 6 | 8 | 10 | 12 | 14 | 16 | 18 | 20 |
|---|---|---|---|---|---|---|---|---|---|---|
| 2 | 100 | 48.684 | 31.907 | 33.858 | 31.923 | 52.669 | 33.043 | 30.545 | 58.537 | 50.965 |
| 4 | 48.684 | 100 | 30.701 | 30.702 | 33.333 | 46.222 | 33.186 | 33.186 | 48.246 | 45.133 |
| 6 | 31.907 | 30.701 | 100 | 99.655 | 78.547 | 32.296 | 47.773 | 46.182 | 33.588 | 31.679 |
| 8 | 33.858 | 30.702 | 99.655 | 100 | 78.201 | 32.296 | 47.773 | 46.182 | 33.588 | 31.679 |
| 10 | 31.923 | 33.333 | 78.547 | 78.201 | 100 | 29.502 | 46.154 | 44.891 | 32.067 | 30.943 |
| 12 | 52.669 | 46.222 | 32.296 | 32.296 | 29.502 | 100 | 33.478 | 31.250 | 53.398 | 48.450 |

TABLE 4-continued

Identity Comparison Using the GAP Program of the Deduced Amino Acid Sequences from Plant cis-Prenyltransferases

| SEQ ID | 2 | 4 | 6 | 8 | 10 | 12 | 14 | 16 | 18 | 20 |
|---|---|---|---|---|---|---|---|---|---|---|
| 14 | 33.043 | 33.186 | 47.773 | 47.773 | 46.154 | 33.478 | 100 | 100 | 32.051 | 37.627 |
| 16 | 30.545 | 33.186 | 46.182 | 46.182 | 44.891 | 31.250 | 100 | 100 | 29.643 | 30.916 |
| 18 | 58.537 | 48.246 | 33.588 | 33.588 | 32.061 | 53.398 | 32.051 | 29.643 | 100 | 50.775 |
| 20 | 50.965 | 45.133 | 90.943 | 31.679 | 30.943 | 48.450 | 37.627 | 30.916 | 50.775 | 100 |

Example 5

Transformation and Expression of Hevea cis-Prenyltransferase in Dandelion Plants A chimeric gene comprising the *Hevea* cis-prenyltransferase gene (SEQ ID NO:5) in sense orientation is constructed by polymerase chain reaction (PCR) of the gene using appropriate oligonucleotide primers. Cloning sites (EcorI and KpnI) are incorporated into the oligonucleotides to provide proper orientation of the DNA fragment when inserted into the digested vector pML82. The binary vectors pML82 are transferred by a freeze/thaw method (Holsters et al., *Mol. Gen. Genet.* 163:181-187 (1978)) to the *Agrobacterium tumefaciens* strain LBA4404 and *Agrobacterium rhizogenes* ATCC 15834 (Hockema et al., *Nature* 303:179-180 (1983)).

Dandelion plants are transformed by co-cultivation of leaf and petiole explants with disarmed *Agrobacterium tumefaciens* strain LBA4404 and *Agrobacterium rhizogenes* strain ATCC 15834 carrying the appropriate binary vector.

Dandelion leaf and petiole explants from greenhouse are sterilized by stirring in 70% ethanol for 10 min and transferring to 5% Chlorox™, 0.01% Triton-X 100 for 30 min, and then rinsing thoroughly with sterile distilled water. Liquid cultures of *Agrobacterium* for plant transformation are grown overnight at 28° C. in Minimal A medium containing 100 mg/L kanamycin. The bacterial cells are pelleted by centrifugation and resuspended in liquid MS medium containing 1 mg/L BAP and 0.2 mg/L NAA to a density of $A_{600}$=0.5, leaf and petiole explants are inoculated with the bacteria suspension for 10 min, blotted dry with sterile filter paper, then co-cultivated on solidified MS medium for two to four days (in case of the explants and strain LBA440 co-cultivation, use MS medium containing 0.5 mg/L BAP and 0.2 mg/L NAA). The co-cultivations are terminated by transferring the explants onto the same medium plus 200 mg/L cefotaxime and 50 mg/L kanamycin to kill the Agrobacteria, and to select for transformed plant cell growth.

The explants inoculated with LBA4404 strain are maintained at 27° C. under cool white fluorescent lamps with a 16/8 h light/dark photoperiod. After three to four weeks, excised shoots are transferred onto rooting medium (1/2 MS plus 0.2 mg/L NAA) containing the same concentrations of antibiotics as above. Once the transformed plants have established their root systems, they are transferred directly into wet Metro-Mix 350 soilless potting medium. The pots are covered with plastic bags which are removed when the plants are clearly growing (after about ten days).

The explants inoculated with ATCC 15834 strain are incubated at 27° C. under continuous dark. After ten to fifteen days, excised roots were transferred to the same plates for large production of the transformed roots.

Example 6

Expression of Plant cis-Prenyltransferase in Microbial Cells and Purification of Gene Product Example 6 illustrates the expression of isolated full length genes encoding cis-prenyltransferase proteins in *E. coli*, using as an example the expression of clone ehb2c.pk001.o18.

Plasmid DNA from ehb2c.pk001.o18 is purified using QIAFilter cartridges (Qiagen Inc., 9600 De Soto Avenue, Chatsworth, Calif.) according to the manufacturer's instructions. Sequence is generated on an ABI Automatic sequencer using dye terminator technology (U.S. Pat. No. 5,366,860; EP 272007) using a combination of vector and insert-specific primers. Sequence editing is performed in either Vector NTI, DNAStar, or the Wisconsin GCG program (vide supra).

cDNA from the full length clone ehb2c.pk001.o18 encoding the instant cis-prenyltransferase enzyme is amplified with specific PCR primers designed to the 5' and 3' ends of the coding region and containing appropriate restriction enzyme digestion sites. The amplified DNA is inserted into the vector pET28b by ligation into restriction sites suitable for expression under the control of the T7lac promoter according to the manufacturer's instructions (Novagen Inc., 597 Science Drive, Madison, Wis.). The vector is then used to transform BL21(DE3) competent *E. coli* hosts, and selected on LB agar plates containing 50 µg/mL kanamycin. Colonies arising from this transformation are grown overnight at 37° C. in Lauria Broth to an $OD_{600}$ of approximately 0.5, and induced with 50 mM IPTG and allowed to grow for an additional 4.5 h. The culture is harvested, resuspended in buffer, lysed with a French press and cleared by centrifugation at 20,000×g. Centrifugation of the supernatant after 20,000×g centrifugation at 100,000×g for 1 h yielded a membrane fraction, which is resuspended in buffer to approximately 7 mg protein/mL. Proteins in this purified membrane fraction are examined on 4-12% SDS-PAGE Gels (Novex, 11040 Roselle Street, San Diego, Calif.) after staining with Gelcode reagent (Pierce, P.O. Box 117, Rockford, Ill.). By comparison of the stained gel with one prepared from similar preparations from *E. coli* cells not expressing the putative cis-prenyltransferase, the protein corresponding to ehb2c.pk001.o18 (molecular mass 34,044 Daltons) is present at a significant level in this purified membrane fraction. Isolation of membranes from microbial hosts containing expressed cis-prenyltransferase proteins as described in this example, or further purification (e.g., by chromatographic means following solubilization of the protein) provides sufficient enzyme protein for analysis by biochemical, chemical or physicochemical means.

Example 7

Expresson of Plant cis-Prenyltransferases in *Arabidopsis thaliana*

Chimeric genes comprising *Hevea*, rice and soybean cis-prenyltransferases (SEQ ID NO:9, 15 and 17, respectively) in sense orientation were constructed by polymerase chain reaction (PCR) from plasmids containing the *Hevea*, rice or soybean cis-prenyltransferase homologs, for expression in *Arabidopsis thaliana*.

The *Hevea* DNA (designated Hpt3) was amplified by PCR from clone ehb2c.pk001.o18, using oligonucleotide primers Hpt3/Xba I (5'-GCTCTAGAGAAGGTTAAGTCAGTT-TAGCATCG-3') (SEQ ID NO:29), and Hpt3/Kpn I (5'-GGGGTACCTTATTTTAAATATTCCTTATGCTTCTCC-3') (SEQ ID NO:30). The amplified Hpt3 cDNAs were digested with XbaI and KpnI and separated on an agrose gel. The DNA fragment was isolated and purified using a QIAguick Gel Extraction Kit according to the manufacture's instructions (Qiagen, USA). The purified DNA fragment was cloned into the corresponding sites of the binary vector pBI-$^{35}$S (vide infra).

The rice and soybean DNAs were similarly isolated by PCR. For these clones, BamHI and SacI cloning sites were incorporated into the oligonucleotide primers to provide proper orientation of the DNA fragment when inserted into the binary vector pGV827. The rice homolog was amplified from clone rr1.pk0050.h8 using primers JK1 (5'-GTG-GATCCATGCTTGGCTCACTTATG-3') (SEQ ID NO:31) and JK2 (5'-TTGAGCTCTATCTCC TCCCAGGGAGG-3') (SEQ ID NO:32) and the soybean homologue was amplified from clone s11.pkO128.h7 using primers JK3 (5'-ACG-GATCCATGTTCTCGTTAAGACTCC-3') (SEQ ID NO:33) and JK4 (5'-TCGAGCTCTTATGAATGTCGAC-CACC-3') (SEQ ID NO:34). PCR products were cloned into the pGEM T-easy vector using a TA-cloning kit (Promega Corporation, 2800 Woods Hollow Road, Madison, Wis.) and these plasmids were then transformed into *E. coli*.

In addition to the cis-prenyltransferase genes identified in in-house databases, several *Arabidopsis thaliana* genomic DNA fragments containing putative cis-prenyl transferase gene sequences were identified in public databases by conducting BLAST searches using the sequences of bacterial and yeast cis-prenyl transferases essentially as outlined in Example 3. One gene, designated Apt5 (SEQ ID NO:37) from *Arabidopsis thaliana* chromosome 5 genomic DNA (GenBank accession number AB011483), contains an 813 nt open reading frame with no intron sequences which encodes a protein with 271 amino acids and extensive homology to the microbial and plant cis-prenyltransferase sequences described in Example s 3 and 4. It was decided to include this gene in our arabidopsis transformation experiments to determine the effect of overexpression of an endogenous gene. The Apt5 gene (SEQ ID NO:37) was cloned by PCR amplification using *Arabidopsis thaliana* genomic DNA as a template. Primers were designed to include specific restriction sites at each end to facilitate in cloning. The Primers used were Apt5/XbaI (5'-CTAGTCTAGAATCTCCCCTC-CGATAACCAAAAAATCC-3') (SEQ ID NO:35)and Apt5/KpnI (5'-GGGGTACCTAGGGTTTAACTTAGAAAC-TATTTAG-3') (SEQ ID NO:36). The amplified Apt5 gene (SEQ ID NO:37) was digested with XbaI and KpnI and separated on an agrose gel. The DNA fragment, ca. 850 bp in length, was isolated and purified using a QIAguick Gel Extraction Kit according to the manufacture's instructions (Qiagen, USA). The purified DNA fragments were cloned into a pBluescript vector according to manufacturer's instructions (Stratagene, 11011 North Torry Pines Road, LaJolla, Calif.).

To verify integrity of the amplified DNAs, plasmids were isolated and purified using QIAFilter cartridges (Qiagen Inc., 9600 De Soto Avenue, Chatsworth, Calif.) according to the manufacturer's instructions. Sequence was generated on an ABI Automatic sequencer using dye terminator technology (U.S. Pat. No. 5,366,860; EP 272007) using a combination of vector-specific primers. Sequence editing was performed in either Vector NTI, DNAStar, or the Wisconsin GCG program (vide supra).

The plasmid, pBI-$^{35}$S, containing Hpt3 gene was transformed into *Argobacterium tumefaciens* strain C58 using a freeze-thaw method (Holsters et al., *Mol. Gen. Genet.* 163: 181-187 (1978)). *Arabidopsis thaliana* plants were transformed via *Agrobacterium*-mediated transformation (Clough S. J., Bent A. F.; *Plant Journal* 1998 December; 16(6): 735-43).

The plasmids encoding rice and soybean cis-prenyltransferases were digested with BamHI and SacI and the cDNA fragments encoding the instant cis-prenyltransferases were isolated by agarose gel purification. The fragments were ligated into a derivative of the binary vector pBIN19 (Frisch, R. A. et al (1995) Complete sequence of the binary vector BIN19. *Plant Molecular Biology* 27, 405-409) containing a $^{35}$S cauliflower mosaic virus promoter and the nopaline synthase 3' translation termination sequence (nos) with appropriate restriction sites. The resulting rice and soybean gene expression constructs were termed $^{35}$S:rr1 and $^{35}$S:s11, respectively. These plasmids were transformed into *E. coli* and the integrity of the binary vectors was confirmed by plasmid isolation and restriction enzyme digestion as described above. The plasmids were then transformed into the *Agrobacterium tumefaciens* strain C58C1 by a freeze/thaw method (Holsters et al., *Mol. Gen. Genet.* 163:181-187 (1978)). *Agrobacterium* lines bearing the binary vector constructs were selected using PCR and used to transform *Arabidopsis thaliana* using the floral dip method (Clough S. J., Bent A. F.; *Plant Journal* 1998 December; 16(6): 735-43).

A binary vector, pBI-$^{35}$S, was constructed for expression of the Apt5 gene (SEQ ID NO:37) in plants by ligating an 800 bp Hind III-Xba I CaMV 35 promoter DNA fragment (Guilley H, Dudley R. K., Jonard G, Balazs E, Richards K. E. (1982) Transcription of Cauliflower mosaic virus DNA: detection of promoter sequences, and characterization of transcripts, *Cell* 30(3):763-73) into the corresponding sites of the vector pBIB/NPT (Detlef Becker (1990) Binary vectors which allow the exchange of plant selectable mekers and reporter genes. *Nucleic Acids Research* 18(1):203) to yield the binary vector pBI-$^{35}$S. The Xba I-Kpn I DNA fragment encoding the Apt5 gene (SEQ ID NO:37) was then cloned into the pBI-$^{35}$S vector, yielding the construct $^{35}$S: Apt5. This construct was transformed into *Argobacterium tumefaciens* strain C18 using a freeze-thaw method (Holsters et al., Mol. Gen. Genet. 163:181-187 (1978)). *Arabidopsis thaliana* plants were transformed via *Agrobacterium*-mediated transformation (Clough S. J., Bent A. F., *Plant Journal* 1998 December; 16(6): 735-43).

The seeds produced from infected plants were plated on agar plates containing 100 µg/ml kanamycin. *Arabidopsis* plants resistant to kanamycin were selected and planted into soil.

Example 8

Analysis of the Polyprenol Profile of Transgenic Plants

Heterozygous transgenic plants expressing either the rice, *Hevea brasiliensis, Arabidopsis* or soybean cis-prenyltransferase homologs described in Example 7 were grown at 19° C., with 18 hours of light/day. Rosette leaves were harvested, frozen in liquid nitrogen and then lyophilized. The dried leaf material was extracted overnight in 2 ml of chloroform:methanol (2:1 v/v); geranylgeraniol was added at 1 μg per 10 mg dry weight to act as an internal standard. The organic extracts were washed with 400 μl of water and the aqueous phase discarded. The extracts were then dried down under a stream of nitrogen, and, after redissolving in 1 ml of 2MKOH/50% methanol, saponified by heating at 70° C. for 2 hours. The saponification mixtures were extracted twice with hexane. A volume of these hexane extracts equivalent to 10 mg (dry weight) of leaf tissue was then analyzed by high-pressure combined liquid chromatography-mass spectrometry (LC_MS), using a Hewlett-Packard 1100 Series LC-MS in atmospheric pressure chemical ionization (APCI) mode.

Chromatography was conducted using a Zorbax C18 (2.1×150 mm; 5 μm) reverse-phase column with methanol:isopropanol:water (12:8:1) at a flow rate of 0.25 ml/min as initial solvent. Polyprenols were eluted by applying a gradient of isopropanol:hexane (1:4), and elution monitored at 210 nm. Polyprenols were identifed by comparing their elution time and mass spectrum with those of authentic standards (Sigma, St. Louis, Mo.).

Figure 5A:
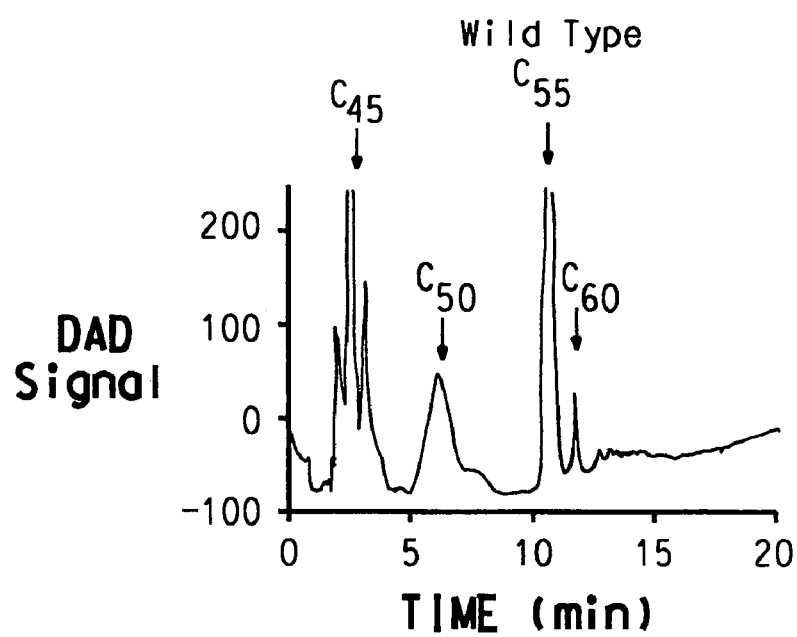
FIG. 5A depicts the chromatogram (diode array detector response at 210 nm) generated by LC-MS analysis of non-saponifiable material extracted from wild-type arabidopsis leaves.
Figure 5B:
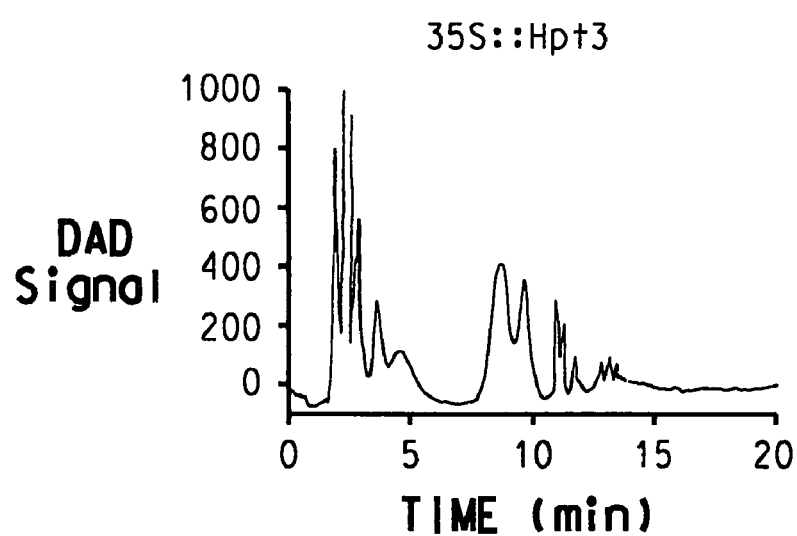
FIG. 5B depicts the chromatogram (diode array detector response at 210 nm) generated by LC-MS analysis of non-saponifiable material extracted from leaves of arabidopsis transformed with a 35S:Hpt3 construct.
Figure 5C:
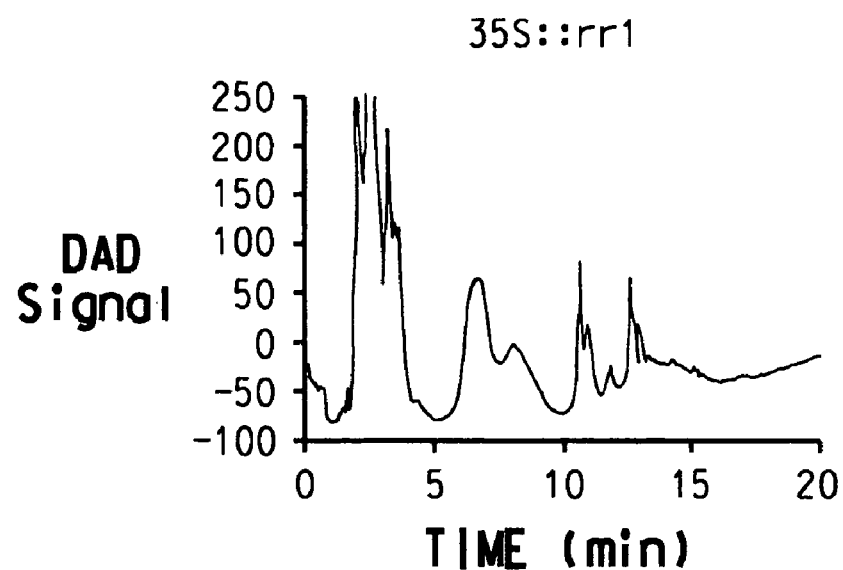
FIG. 5C depicts the chromatogram (diode array detector response at 210 nm) generated by LC-MS analysis of non-saponifiable material extracted from leaves of arabidopsis transformed with a 35S:rr1 construct.
Figure 5D:
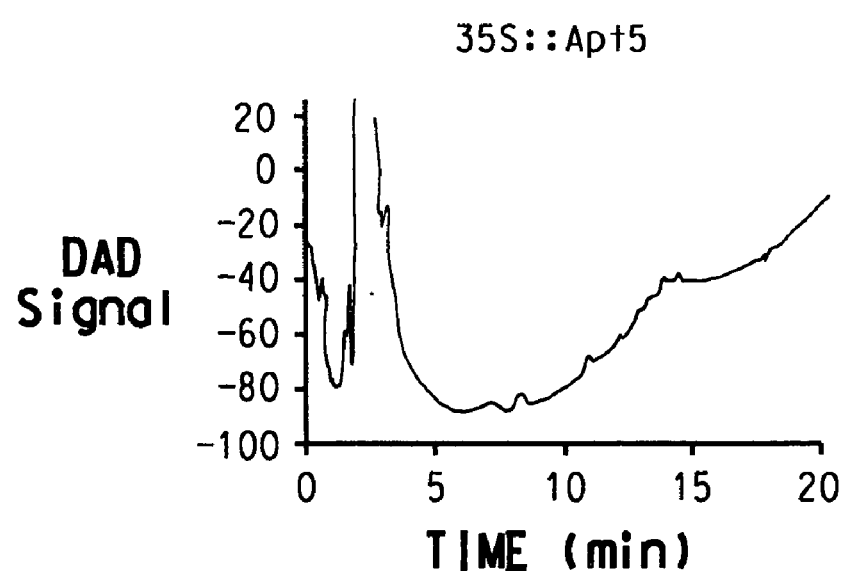
FIG. 5D depicts the chromatogram (diode array detector response at 210 nm) generated by LC-MS analysis of non-saponifiable material extracted from leaves of arabidopsis transformed with a 35S:Apt5 construct.
Figure 5E:
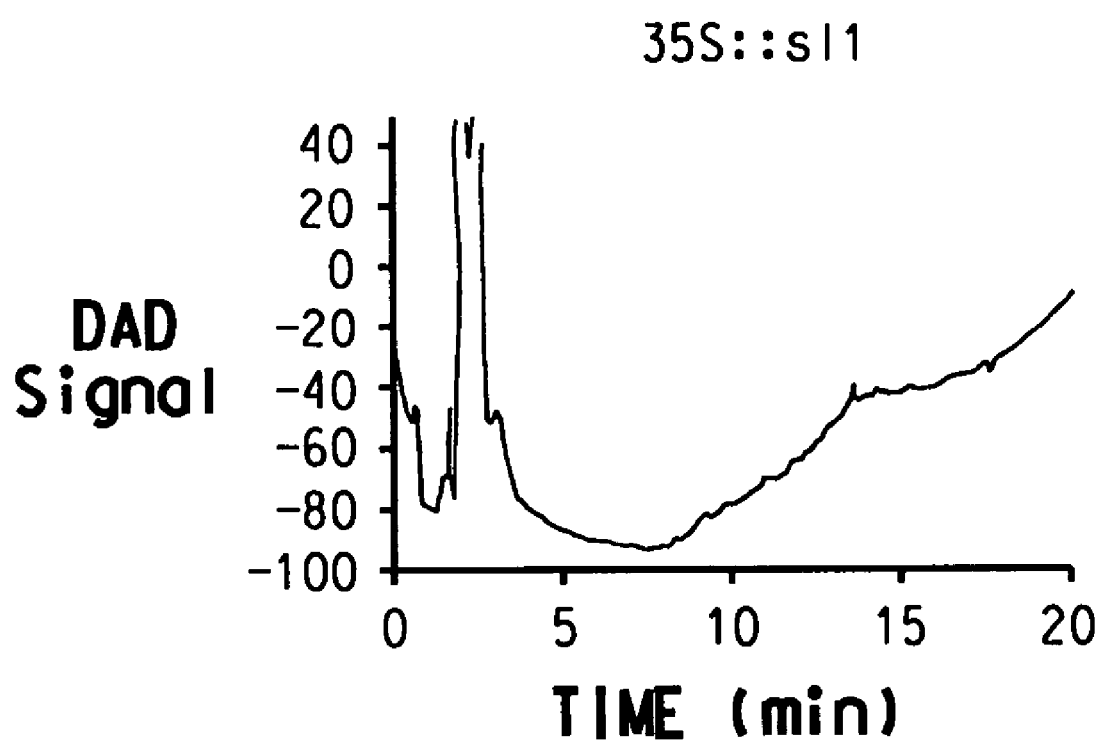
FIG. 5E depicts the chromatogram (diode array detector response at 210 nm) generated by LC-MS analysis of non-saponifiable material extracted from leaves of arabidopsis transformed with a 35S:S11 construct.
Figure 6A:
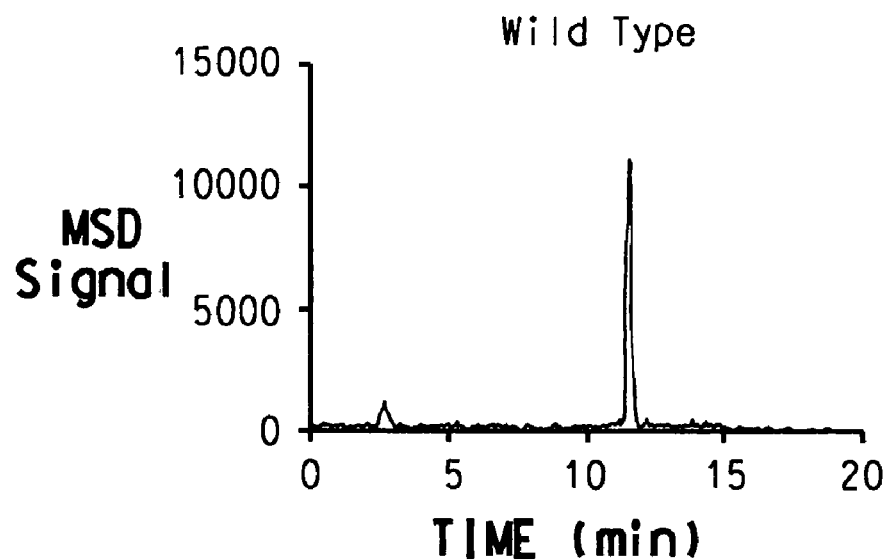
FIG. 6A depicts the extracted ion chromatogram for dodecaprenol (mass detector response to ions with m/z 816 to 818) generated by LC-MS analysis of non-saponifiable material extracted from wild-type arabidopsis leaves.
Figure 6B:
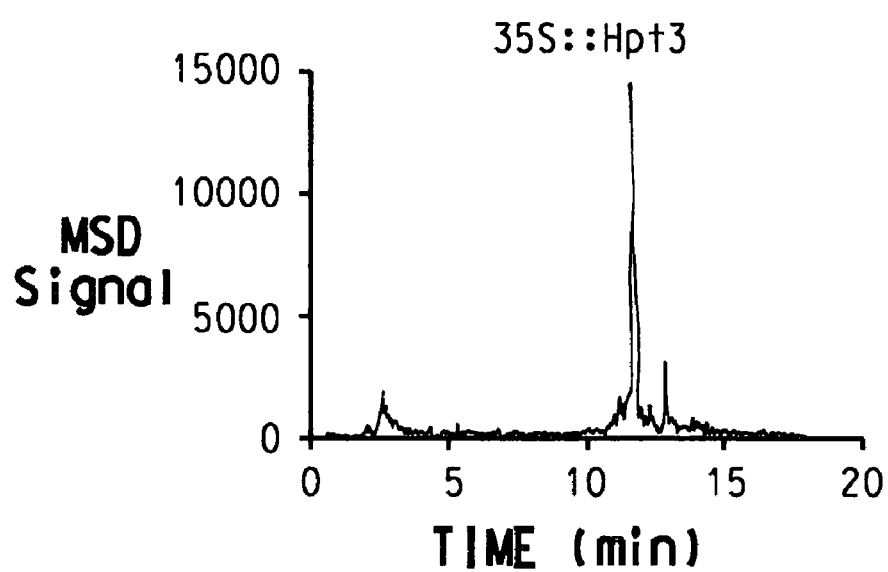
FIG. 6B depicts the extracted ion chromatogram for dodecaprenol (mass detector response to ions with m/z 816 to 818) generated by LC-MS analysis of non-saponifiable material extracted from leaves of arabidopsis transformed with a 35S:Hpt3 construct.
Figure 6C:
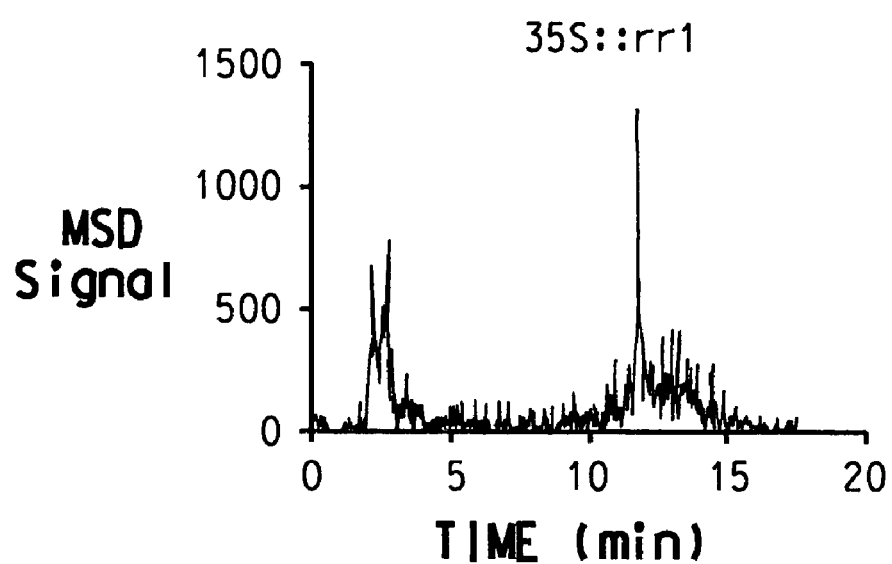
FIG. 6C depicts the extracted ion chromatogram for dodecaprenol (mass detector response to ions with m/z 816 to 818) generated by LC-MS analysis of non-saponifiable material extracted from leaves of arabidopsis transformed with a 35S:rr1 construct.
Figure 6D:
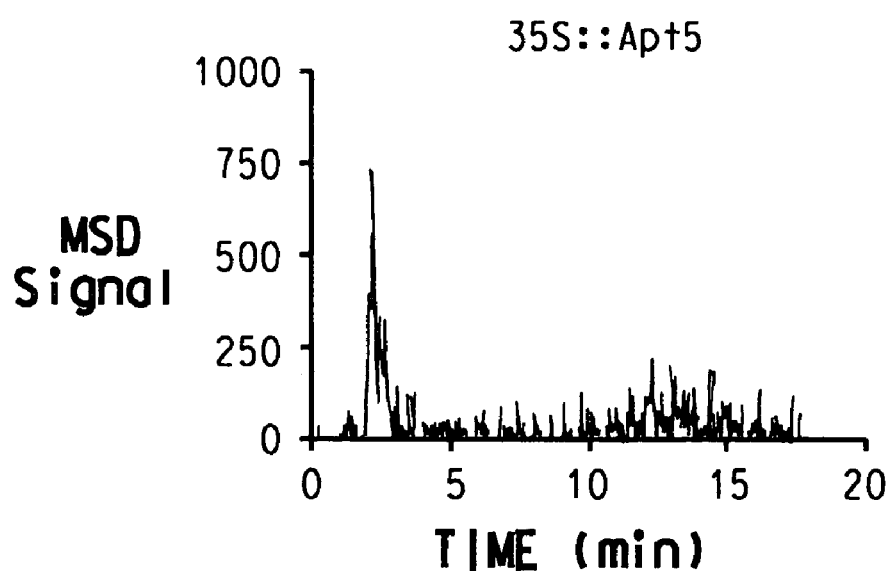
FIG. 6D depicts the extracted ion chromatogram for dodecaprenol (mass detector response to ions with m/z 816 to 818) generated by LC-MS analysis of non-saponifiable material extracted from leaves of arabidopsis transformed with a 35S:Apt5 construct.
Figure 6E:
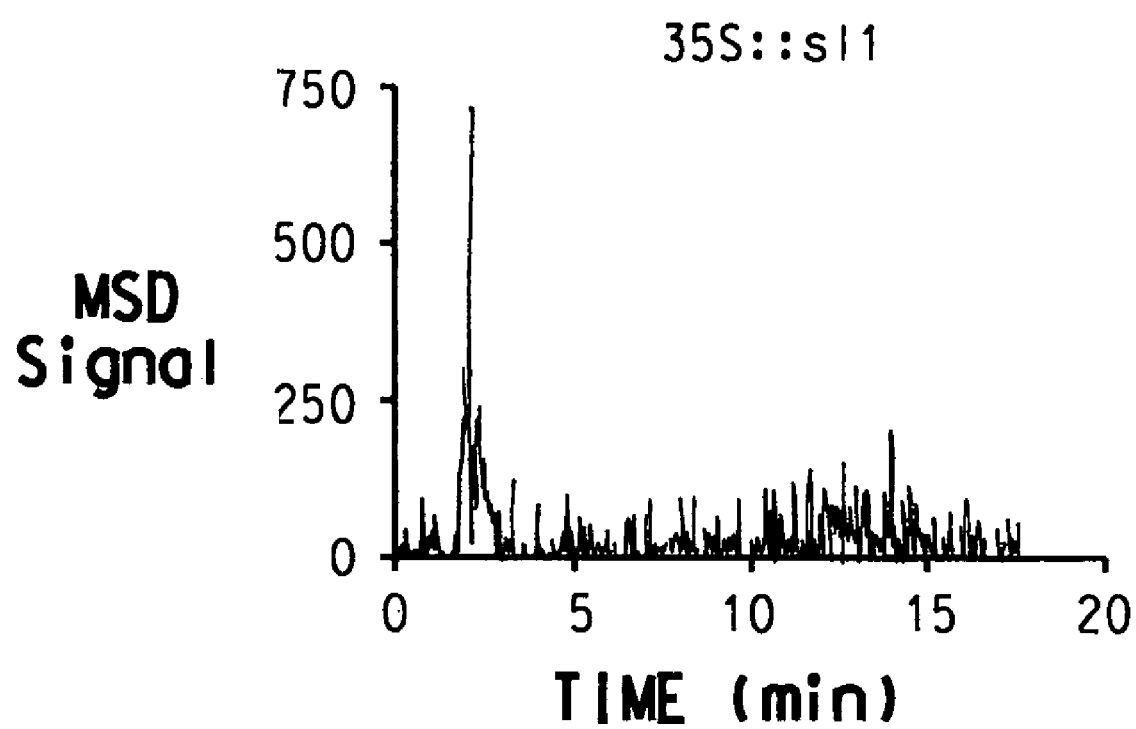
FIG. 6E depicts the extracted ion chromatogram for dodecaprenol (mass detector response to ions with m/z 816 to 818) generated by LC-MS analysis of non-saponifiable material extracted from leaves of arabidopsis transformed with a 35S:S11 construct.

The data from these analyses indicated that expression of the soybean clone s11.pk0128.h7 (SEQ ID NO:17) and overexpression of the arabidopsis cis-prenyltransferase Apt5 caused significant alteration of the polyprenol composition of leaves of the transgenic arabidopsis plants. In both of these cases, dodecaprenol (a 60-carbon polyprenol ($C_{60}$), composed of 12 isoprene units) was undetectable either by examination of the diode array detector (DAD; FIG. 5) response or by selective ion monitoring of the mass detector data (Table 5; FIG. 6).

FIG. 5 illustrates the LC-MS analysis of extracts from wild-type and transgenic arabidopsis leaves. Samples equivalent to 10 mg leaf dry weight were separated by reverse phase chromatography and polyprenol elution was monitored at 210 nm using a diode array detector (DAD). Elution of standard polyprenols (C45-C60) was indicated in the profile of the extract from wild-type arabidopsis. Similarly FIG. 6 the LC-MS analysis of the molecular ion for dodecaprenol (C60) in rosette leaves of arabidopsis.

In addition to this primary effect, the amounts of other polyprenols (45-, 50-, 55-carbon) were drastically reduced (FIG. 5) compared to extracts of wild-type plants (which contain significant amounts of all of these polyprenols; Table 5, FIG. 5). This effect was not seen in plants expressing the *Hevea* Hpt3 or rice clones. The data clearly indicates that overexpression of at least two of the genes identified in Examples 2 and 3, which by homology appear to encode plant cis-prenyltransferases, dramatically alters the phenotype of transgenic plants with regard to polyprenol composition.

TABLE 5

Polyprenol profiles of Transgenic Arabidopsis Leaves

| polyprenol | Wild-type | 35S::Hpt3 | 35S::rr1 | 35::Sl1 | 35S::Apt3 |
|---|---|---|---|---|---|
| C45 | + | + | + | + | + |
| m/z 612–614 | | | | | |
| C50 | + | + | + | + | + |
| m/z 680–682 | | | | | |
| C55 | + | + | + | + | + |
| m/z 748–750 | | | | | |
| C60 | + | + | + | – | – |
| m/z 816–818 | | | | | |

The presence of a particular polyprenol in extracts of wild type or transgenic arabidopsis leaves was determined by selective ion monitoring of the mass spectrometer output during chromatography of extracts. Presence is indicated by a '+' symbol, absence by a '–'.

What is claimed is:

1. An isolated nucleic acid fragment encoding a plant cis-prenyltransferase enzyme selected from the group consisting of:
   (a) an isolated nucleic acid fragment encoding the amino acid sequence as set forth in SEQ ID NO:4; and
   (b) an isolated nucleic acid molecule that hybridizes with a nucleic acid sequence of (a) under the following conditions: 0.1×SSC, 0.1% SDS, 65° C., and washed with 0.2×SSC, 0.5% SDS.

2. The isolated nucleic acid fragment of claim 1 as set forth in SEQ ID NO: 3.

3. A chimeric gene comprising the isolated nucleic acid fragment of claim 1 operably linked to a suitable regulatory sequence.

4. A transformed host cell comprising the chimeric gene of claim 3.

5. The transformed host cell of claim 4 wherein the host cell is selected from the group consisting of plant cells and microbial cells.

6. The host cell according to claim 5 selected from the group consisting of tobacco (*Nicotiana* spp.), tomato (*Lycopersicon* spp.), potato (*Solanum* spp.), hemp (*Cannabis* spp.), sunflower (*Helianthus* spp.), sorghum (*Sorghum vulgare*), wheat (*Triticum* spp.), maize (*Zea mays*), rice (*Oryza sativa*), rye (*Secale cereale*), oats (*Avena* spp.), barley (*Hordeum vulgare*), rapeseed (*Brassica* spp.), broad bean (*Vicia faba*), french bean (*Phaseolus vulgaris*), other bean species (*Vigna* spp.), lentil (*Lens culinaris*), soybean (*Glycine max*), arabidopsis (*Arabidopsis thaliana*), guayule (*Parthenium argentatum*), cotton (*Gossypium hirsutum*), petunia (*Petunia hybrida*), flax (*Linum usitatissimum*); carrot (*Daucus carota sativa*); and rubber tree (*Hevea brasiliensis*).

7. The transformed host cell of claim 5 wherein the host cell is selected from the group consisting of *Aspergillus, Saccharomyces, Pichia, Candida, Hansenula, Bacillus, Escherichia, Salmonella* and *Shigella*.

\* \* \* \* \*

SEQUENCE LISTING

```
<160> NUMBER OF SEQ ID NOS: 37

<210> SEQ ID NO 1
<211> LENGTH: 1388
<212> TYPE: DNA
<213> ORGANISM: Dimorphotheca

<400> SEQUENCE: 1
ggcacgacag gtttcccgac tggaaagcgg gcagtgagcg caacgcaatt aatgtgagtt      60
agctcactca ttaggcaccg caggctttac actttatgct tccggctcgt atgttgtgtg     120
gaattgtgag cggataacaa tttcacacag gaaacagcta tgaccatgat tacgccaagc     180
gcgcaattaa ccctcactaa agggaacaaa aggctggagc tccaccgcgg tggcggccgc     240
tctagaacta gtggatcccc cgggctgcag gaattcggca cgagcttaaa taatgcttaa     300
tcttcccctc tacttaccca aatatccttg ttatttcccg gcctctctct ccaccaacca     360
ccaccgtggt ctttatgtat tcaaccaatc agacaccact ggaggtggaa ttaattcgct     420
```

```
ggaggaacgc attactccag caggactcaa gcacgagtta atgccaaagc atgtggcagt      480
gatcatggat ggaaacagga gatgggctcg atcacgtggg ttaatgccgg atgctggtta      540
catggaaggt gcacgctcat tgaaggtgat ggtggaattg tgtcgtaaat ggggaattca      600
agtccttact gtgtttgcct tctcagctga taactggtta agacccaaag ttgaagttga      660
tttcttgatg ggactaattg aaagtgtatt aaaagatgaa gttgttcata tgatcaaaga      720
gggtatccag ctttcggtta tcggagacac atctaagctt ccaaaatcgg taaaacggat      780
cattacatat gctgaaaaca tcacgaagaa caactcacaa ctcaatcttg ttgtagcaat      840
aaattatagt ggaaaatatg atatcgtcca agcttgtcaa agcatcgcac taaaagtcaa      900
agacggtgtc attcaacccg aagaaatcaa tgagtttacg attgaaaatg aacttggtac      960
aaattgtatt cctttccac accctgatct actaattcgg actagtgggg agcttagagt     1020
gagcaacttc ttttgtggc aattggcgta tactgaatta tacttcagtg aaactctttg     1080
gcctgatttt ggtgaagatg aacttttaca tgctttaaat acttttcaac atagacgaag     1140
acgttatggt ggatgagatt cttaaacaac cctgtagagt tgcatatcat attgactttt     1200
gatatgtttc aatactattt atattattat tatgttgtaa tatcgtacta gaacatgaat     1260
ttaaataggc aatagagcat gccacctaat atgtctagtt atgagattct aaagacgtaa     1320
ttatgcttac ctaaaagaaa atatatatga agagaaaagc ttatgtaaaa aaaaaaaaa     1380 aaaaaaaa                                                              1388

<210> SEQ ID NO 2
<211> LENGTH: 287
<212> TYPE: PRT
<213> ORGANISM: Dimorphotheca

<400> SEQUENCE: 2

Met Leu Asn Leu Pro Leu Tyr Leu Pro Lys Tyr Pro Cys Tyr Phe Pro
  1               5                  10                  15

Ala Ser Leu Ser Thr Asn His His Arg Gly Leu Tyr Val Phe Asn Gln
                 20                  25                  30

Ser Asp Thr Thr Gly Gly Gly Ile Asn Ser Leu Glu Glu Arg Ile Thr
             35                  40                  45

Pro Ala Gly Leu Lys His Glu Leu Met Pro Lys His Val Ala Val Ile
         50                  55                  60

Met Asp Gly Asn Arg Arg Trp Ala Arg Ser Arg Gly Leu Met Pro Asp
 65                  70                  75                  80

Ala Gly Tyr Met Glu Gly Ala Arg Ser Leu Lys Val Met Val Glu Leu
                 85                  90                  95

Cys Arg Lys Trp Gly Ile Gln Val Leu Thr Val Phe Ala Phe Ser Ala
            100                 105                 110

Asp Asn Trp Leu Arg Pro Lys Val Glu Val Asp Phe Leu Met Gly Leu
            115                 120                 125

Ile Glu Ser Val Leu Lys Asp Glu Val Val His Met Ile Lys Glu Gly
        130                 135                 140

Ile Gln Leu Ser Val Ile Gly Asp Thr Ser Lys Leu Pro Lys Ser Val
145                 150                 155                 160

Lys Arg Ile Ile Thr Tyr Ala Glu Asn Ile Thr Lys Asn Asn Ser Gln
                165                 170                 175

Leu Asn Leu Val Val Ala Ile Asn Tyr Ser Gly Lys Tyr Asp Ile Val
            180                 185                 190
```

```
Gln Ala Cys Gln Ser Ile Ala Leu Lys Val Lys Asp Gly Val Ile Gln
        195                 200                 205

Pro Glu Glu Ile Asn Glu Phe Thr Ile Glu Asn Glu Leu Gly Thr Asn
    210                 215                 220

Cys Ile Pro Phe Pro His Pro Asp Leu Leu Ile Arg Thr Ser Gly Glu
225                 230                 235                 240

Leu Arg Val Ser Asn Phe Phe Leu Trp Gln Leu Ala Tyr Thr Glu Leu
                245                 250                 255

Tyr Phe Ser Glu Thr Leu Trp Pro Asp Phe Gly Glu Asp Glu Leu Leu
            260                 265                 270

His Ala Leu Asn Thr Phe Gln His Arg Arg Arg Tyr Gly Gly
        275                 280                 285

<210> SEQ ID NO 3
<211> LENGTH: 1082
<212> TYPE: DNA
<213> ORGANISM: Calendula officinalis

<400> SEQUENCE: 3
atgacattat tttccctaat tactcaatta aaccttgttt agctcctaaa ccacactctt      60
ccaactctaa tttcttcaac cgcgtgtcac caataacttc ggggataatt cgttcatcga     120
ttacaaatat atcaacggtt ttgagcaatg aaaataccaa actgaaaacc aaaaaaagaa     180
gaagtagaat taccaggggg tctcgaagaa gaactaatgc caaaacacgt tgcattcata     240
atggatggaa accgtcgatg ggcggtggaa aaggttggt ctccaatgac gggtcatagt      300
gccatgagaa agacgcttca atctctcctt tttcgatgtt ccaaattcaa aatcaaagcg     360
gtatcgattt atgcattttc taccgaaaat tggactcgcc cgaaggaaga agttgatttc     420
ctaatggaga tgtatgaaga tttattgagg acagatgctg aggagctctt aagtcttggt     480
tgtcgagtaa gcataatggg aaaaagacc aaccttccga aatcactaca aaagttatgc      540
atcgaaatag aagaaaaatc aagagccaat tcaggaaccc atgttaacta tgcactcaac     600
tacagtggaa atacgacat aatcgaagct tgtaaaagcg tcgctacaaa agtcaaggat      660
ggtgttatta ttccaaaaca gatcgacgaa aaatatttca acaagaact cggtaccaaa      720
atgatcgatt ttccttaccc tgacctagtt atacgtacaa gcggggaaat taggcttagt     780
aatttcatgc tatggcagat ggcgtatagc gagctttatt tcacggataa atactttccg     840
gattttgggg aaaatgatct tatcgaggct ttacttgcat ttcaaaaagt gcgtaaatgt     900
taataacttg ttgtggttaa gacgagtgtg gtagaatatc aataaatgac tcgtttcggc     960
ggcgttgtgt atgccacatt atatgtctta gtgtctatca gaattcgaat ttgatttata    1020
gtcgcttgag atatgaaaac ttattatatt tgttcgatca aaaaaaaaa aaaaaaaaaa    1080
aa                                                                  1082

<210> SEQ ID NO 4
<211> LENGTH: 228
<212> TYPE: PRT
<213> ORGANISM: Calendula officinalis

<400> SEQUENCE: 4

Met Pro Lys His Val Ala Phe Ile Met Asp Gly Asn Arg Arg Trp Ala
1               5                   10                  15

Val Glu Lys Gly Trp Ser Pro Met Thr Gly His Ser Ala Met Arg Lys
                20                  25                  30

Thr Leu Gln Ser Leu Leu Phe Arg Cys Ser Lys Phe Lys Ile Lys Ala
```

```
                35                  40                  45
Val Ser Ile Tyr Ala Phe Ser Thr Glu Asn Trp Thr Arg Pro Lys Glu
 50                  55                  60

Glu Val Asp Phe Leu Met Glu Met Tyr Glu Asp Leu Leu Arg Thr Asp
 65                  70                  75                  80

Ala Glu Glu Leu Leu Ser Leu Gly Cys Arg Val Ser Ile Met Gly Lys
                 85                  90                  95

Lys Thr Asn Leu Pro Lys Ser Leu Gln Lys Leu Cys Ile Glu Ile Glu
                100                 105                 110

Glu Lys Ser Arg Ala Asn Ser Gly Thr His Val Asn Tyr Ala Leu Asn
                115                 120                 125

Tyr Ser Gly Lys Tyr Asp Ile Ile Glu Ala Cys Lys Ser Val Ala Thr
130                 135                 140

Lys Val Lys Asp Gly Val Ile Ile Pro Lys Gln Ile Asp Glu Lys Tyr
145                 150                 155                 160

Phe Lys Gln Glu Leu Gly Thr Lys Met Ile Asp Phe Pro Tyr Pro Asp
                165                 170                 175

Leu Val Ile Arg Thr Ser Gly Glu Ile Arg Leu Ser Asn Phe Met Leu
                180                 185                 190

Trp Gln Met Ala Tyr Ser Glu Leu Tyr Phe Thr Asp Lys Tyr Phe Pro
                195                 200                 205

Asp Phe Gly Glu Asn Asp Leu Ile Glu Ala Leu Leu Ala Phe Gln Lys
                210                 215                 220

Val Arg Lys Cys
225

<210> SEQ ID NO 5
<211> LENGTH: 1071
<212> TYPE: DNA
<213> ORGANISM: Hevea brasiliensis

<400> SEQUENCE: 5
tctcattcga gtgctcaagt tgcaaaccac ttttgatttt ggaggattta ccgagtcacc      60
tacaggcttc gggttaaagc atcgtgatgt gggtttaagg aaatggaatt atataccagt     120
taagtcagtg atttaaggaa aatggaatta caacggtga gaggccaag tgtgttcaga       180 cttttaggga agtatatgag aaaagggtta tatagcatcc taacccaggg tcccatccct     240
actcatattg ccttcatatt ggatggaaac aggaggtttg ctaagaagca taaactgcca     300
gaaggaggtg gtcataaggc tggattttta gctcttctga acgtactaac ttattgctat     360
gagttaggag tgaaatatgc gactatctat gcctttagca tcgataattt tcgaaggaaa     420
cctcatgagg ttcagtacgt aatggatcta atgctgagaa agattgaagg gatgatcatg     480
gaagaaagta tcatcaatgc atatgatatt tgcgtacgtt ttgtgggtaa cctgaagctt     540
ttaagtgagc ccgtcaagac cgcagcagat aagattatga gggctactgc caacaattcc     600
aaatgtgtgc ttctcattgc tgtatgctat acttcaactg atgagatcgt gcatgctgtt     660
gaagaatcct ctgaattgaa ctccaatgaa gtttgtaaca atcaagaatt ggaggaggca     720
aatgcaactg gaagcagtac tgtgattcaa actgagaaca tggagtcgta ttctggaata     780
aaacttgtag accttgagaa aaacacctac ataaatcctt atcctgatgt tctgattcga     840
acttctgggg agacccgtct gagcaactac ttactttggc agactactaa ttgcatactg     900
tattctcctt atgcactgtg gccagagatt ggtcttcgac acgtggtgtg gtcagtaatt     960
aacttccaac gtcattattc ttacttggag aaacataagg aatacttaaa ataatttggt    1020
```
tctgttccta gctcatcctg ccttattccg ataggttaag cttaagcata t            1071

<210> SEQ ID NO 6
<211> LENGTH: 290
<212> TYPE: PRT
<213> ORGANISM: Hevea brasiliensis

<400> SEQUENCE: 6

```
Met Glu Leu Tyr Asn Gly Glu Arg Pro Ser Val Phe Arg Leu Leu Gly
  1               5                  10                  15

Lys Tyr Met Arg Lys Gly Leu Tyr Ser Ile Leu Thr Gln Gly Pro Ile
             20                  25                  30

Pro Thr His Ile Ala Phe Ile Leu Asp Gly Asn Arg Arg Phe Ala Lys
         35                  40                  45

Lys His Lys Leu Pro Glu Gly Gly His Lys Ala Gly Phe Leu Ala
     50                  55                  60

Leu Leu Asn Val Leu Thr Tyr Cys Tyr Glu Leu Gly Val Lys Tyr Ala
 65                  70                  75                  80

Thr Ile Tyr Ala Phe Ser Ile Asp Asn Phe Arg Arg Lys Pro His Glu
                 85                  90                  95

Val Gln Tyr Val Met Asp Leu Met Leu Glu Lys Ile Glu Gly Met Ile
            100                 105                 110

Met Glu Glu Ser Ile Ile Asn Ala Tyr Asp Ile Cys Val Arg Phe Val
        115                 120                 125

Gly Asn Leu Lys Leu Leu Ser Glu Pro Val Lys Thr Ala Ala Asp Lys
    130                 135                 140

Ile Met Arg Ala Thr Ala Asn Asn Ser Lys Cys Val Leu Leu Ile Ala
145                 150                 155                 160

Val Cys Tyr Thr Ser Thr Asp Glu Ile Val His Ala Val Glu Glu Ser
                165                 170                 175

Ser Glu Leu Asn Ser Asn Glu Val Cys Asn Asn Gln Glu Leu Glu Glu
            180                 185                 190

Ala Asn Ala Thr Gly Ser Ser Thr Val Ile Gln Thr Glu Asn Met Glu
        195                 200                 205

Ser Tyr Ser Gly Ile Lys Leu Val Asp Leu Glu Lys Asn Thr Tyr Ile
    210                 215                 220

Asn Pro Tyr Pro Asp Val Leu Ile Arg Thr Ser Gly Glu Thr Arg Leu
225                 230                 235                 240

Ser Asn Tyr Leu Leu Trp Gln Thr Thr Asn Cys Ile Leu Tyr Ser Pro
                245                 250                 255

Tyr Ala Leu Trp Pro Glu Ile Gly Leu Arg His Val Val Trp Ser Val
            260                 265                 270

Ile Asn Phe Gln Arg His Tyr Ser Tyr Leu Glu Lys His Lys Glu Tyr
        275                 280                 285

Leu Lys
    290
```

<210> SEQ ID NO 7
<211> LENGTH: 1000
<212> TYPE: DNA
<213> ORGANISM: Hevea brasiliensis

<400> SEQUENCE: 7
cgggttaagt cagtgattta aggaaaatgg aattatacaa cggtgagagg ccaagtgtgt            60
tcagactttt agagaagtat atgagaaaag ggttatatag catcctaacc cagggtccca           120

-continued

```
tccctactca tattgccttc atattggatg gaaacaggag gtttgctaag aagcataaac    180
tgccagaagg aggtggtcat aaggctggat ttttagctct tctgaacgta ctaacttatt    240
gctatgagtt aggagtgaaa tatgcgacta tctatgcctt tagcatcgat aattttcgaa    300
ggaaacctca tgaggttcag tacgtaatgg atctaatgct ggagaagatt gaagggatga    360
tcatggaaga aagtatcatc aatgcatatg atatttgcgt acgttttgtg ggtaacctga    420
agcttttaag tgagccagtc aagaccgcag cagataagat tatgagggct actgccaaca    480
attccaaatg tgtgcttctc attgctgtat gctatacttc aactgatgag atcgtgcatg    540
ctgttgaaga atcctctgaa ttgaactcca atgaagtttg taacaatcaa gaattggagg    600
aggcaaatgc aactggaagc agtactgtga ttcaaactga aacatggag tcgtattctg    660
gaataaaact tgtagacctt gagaaaaaca cctacataaa tccttatcct gatgttctga    720
ttcgaacttc tggggagacc cgtctgagca actacttact ttggcagact actaattgca    780
tactgtattc tccttatgca ctgtggccag agattggtct tcgacacgtg gtgtggtcag    840
taattaactt ccaacgtcat tattcttact tggagaaaca taaggaatac ttaaaataat    900
ttgtttctgt tcctagctca tcctgcctta ttcgcgatag ttaagcttaa gcatatcctt    960
gtggaataaa ctcggacact taattaagcc ggtattttgt                         1000
```

<210> SEQ ID NO 8
<211> LENGTH: 290
<212> TYPE: PRT
<213> ORGANISM: Hevea brasiliensis

<400> SEQUENCE: 8

```
Met Glu Leu Tyr Asn Gly Glu Arg Pro Ser Val Phe Arg Leu Leu Glu
  1               5                  10                  15

Lys Tyr Met Arg Lys Gly Leu Tyr Ser Ile Leu Thr Gln Gly Pro Ile
             20                  25                  30

Pro Thr His Ile Ala Phe Ile Leu Asp Gly Asn Arg Arg Phe Ala Lys
         35                  40                  45

Lys His Lys Leu Pro Glu Gly Gly His Lys Ala Gly Phe Leu Ala
     50                  55                  60

Leu Leu Asn Val Leu Thr Tyr Cys Tyr Glu Leu Gly Val Lys Tyr Ala
 65                  70                  75                  80

Thr Ile Tyr Ala Phe Ser Ile Asp Asn Phe Arg Arg Lys Pro His Glu
                 85                  90                  95

Val Gln Tyr Val Met Asp Leu Met Leu Glu Lys Ile Glu Gly Met Ile
            100                 105                 110

Met Glu Glu Ser Ile Ile Asn Ala Tyr Asp Ile Cys Val Arg Phe Val
        115                 120                 125

Gly Asn Leu Lys Leu Leu Ser Glu Pro Val Lys Thr Ala Ala Asp Lys
    130                 135                 140

Ile Met Arg Ala Thr Ala Asn Asn Ser Lys Cys Val Leu Leu Ile Ala
145                 150                 155                 160

Val Cys Tyr Thr Ser Thr Asp Glu Ile Val His Ala Val Glu Glu Ser
                165                 170                 175

Ser Glu Leu Asn Ser Asn Glu Val Cys Asn Asn Gln Glu Leu Glu Glu
            180                 185                 190

Ala Asn Ala Thr Gly Ser Ser Thr Val Ile Gln Thr Glu Asn Met Glu
        195                 200                 205

Ser Tyr Ser Gly Ile Lys Leu Val Asp Leu Glu Lys Asn Thr Tyr Ile
```

```
                 210                 215                 220
Asn Pro Tyr Pro Asp Val Leu Ile Arg Thr Ser Gly Glu Thr Arg Leu
225                 230                 235                 240

Ser Asn Tyr Leu Leu Trp Gln Thr Thr Asn Cys Ile Leu Tyr Ser Pro
                245                 250                 255

Tyr Ala Leu Trp Pro Glu Ile Gly Leu Arg His Val Val Trp Ser Val
                260                 265                 270

Ile Asn Phe Gln Arg His Tyr Ser Tyr Leu Glu Lys His Lys Glu Tyr
            275                 280                 285

Leu Lys
    290

<210> SEQ ID NO 9
<211> LENGTH: 1000
<212> TYPE: DNA
<213> ORGANISM: Hevea brasiliensis

<400> SEQUENCE: 9
ccgagtcacg tataggcttc gtgtgaaggt taagtcagtt tagcatcggg atttgggttt      60
aaggaaaatg gaaatatata cgggtcagag gccaagtgtg tttagaattt ttgggaaata    120
catgagaaaa gggttatata gcatcctaac ccaaggtccc atccctactc atcttgcctt    180
cataatggat ggaaaccgga ggtttgctaa gaagcacaaa atgaaagaag cagaaggtta    240
taaggcagga tatttagctc ttctgagaac actaacttat tgctatgagt tgggagtgag    300
gtatgtaacc atttatgcct ttagcattga taattttcga aggcaacctc gtgaggttca    360
gtgcgtaatg aatctaatga tggagaagat tgaagagatt atcgtggaag aaagtatcat    420
gaatgcatat gatgttggcg tacgtattgt gggtaacctg aatcttttag atgagccaat    480
caggatcgca gcagaaaaga ttatgagggc tactgccaat aattccgggt ttgtgcttct    540
cattgctgta gcctatagtt caactgatga gatcgggcat gctgttgaag aatcctctaa    600
agacaaattg aactccaatg aagtttgcaa caatgggatt gaagctgaac aggaatttaa    660
ggaggcaaac ggaaccggaa acagtgtgat tccagttcag aagacggagt catattctgg    720
aataaatctt gcagaccttg agaaaaacac ctacgtaaat cctcatcctg atgtcttgat    780
tcgaacttct gggttgagcc gtctaagtaa ctacctactt tggcagacta gtaattgcat    840
actgtattct ccttttgcac tgtggccaga gattggtctc aggcacttgg tatggacagt    900
aatgaacttc caacgtcatc attcttattt ggagaagcat aaggaatatt taaataatt    960 tattttttgtt cctaactcat cctgcctta tcgggataga                          1000

<210> SEQ ID NO 10
<211> LENGTH: 296
<212> TYPE: PRT
<213> ORGANISM: Hevea brasiliensis

<400> SEQUENCE: 10

Met Glu Ile Tyr Thr Gly Gln Arg Pro Ser Val Phe Arg Ile Phe Gly
1               5                   10                  15

Lys Tyr Met Arg Lys Gly Leu Tyr Ser Ile Leu Thr Gln Gly Pro Ile
                20                  25                  30

Pro Thr His Leu Ala Phe Ile Met Asp Gly Asn Arg Arg Phe Ala Lys
            35                  40                  45

Lys His Lys Met Lys Glu Ala Glu Gly Tyr Lys Ala Gly Tyr Leu Ala
        50                  55                  60
```

Leu Leu Arg Thr Leu Thr Tyr Cys Tyr Glu Leu Gly Val Arg Tyr Val
 65                  70                  75                  80

Thr Ile Tyr Ala Phe Ser Ile Asp Asn Phe Arg Gln Pro Arg Glu
             85                  90                  95

Val Gln Cys Val Met Asn Leu Met Met Glu Lys Ile Glu Glu Ile Ile
            100                 105                 110

Val Glu Glu Ser Ile Met Asn Ala Tyr Asp Val Gly Val Arg Ile Val
            115                 120                 125

Gly Asn Leu Asn Leu Leu Asp Glu Pro Ile Arg Ile Ala Ala Glu Lys
130                 135                 140

Ile Met Arg Ala Thr Ala Asn Asn Ser Gly Phe Val Leu Leu Ile Ala
145                 150                 155                 160

Val Ala Tyr Ser Ser Thr Asp Glu Ile Gly His Ala Val Glu Glu Ser
                165                 170                 175

Ser Lys Asp Lys Leu Asn Ser Asn Glu Val Cys Asn Asn Gly Ile Glu
            180                 185                 190

Ala Glu Gln Glu Phe Lys Glu Ala Asn Gly Thr Gly Asn Ser Val Ile
            195                 200                 205

Pro Val Gln Lys Thr Glu Ser Tyr Ser Gly Ile Asn Leu Ala Asp Leu
        210                 215                 220

Glu Lys Asn Thr Tyr Val Asn Pro His Pro Asp Val Leu Ile Arg Thr
225                 230                 235                 240

Ser Gly Leu Ser Arg Leu Ser Asn Tyr Leu Leu Trp Gln Thr Ser Asn
                245                 250                 255

Cys Ile Leu Tyr Ser Pro Phe Ala Leu Trp Pro Glu Ile Gly Leu Arg
            260                 265                 270

His Leu Val Trp Thr Val Met Asn Phe Gln Arg His His Ser Tyr Leu
        275                 280                 285

Glu Lys His Lys Glu Tyr Leu Lys
    290                 295

<210> SEQ ID NO 11
<211> LENGTH: 1232
<212> TYPE: DNA
<213> ORGANISM: Vitis sp

<400> SEQUENCE: 11
gagaaacatt atcctaaccc tagtcctgaa actcctgata atgctctctt ttcgatttcc      60
aatttcagct gataacgctc gccatacttt caagtccaaa cactcttctt gtacttttcg     120
aagtaacaga atcgattcat tttcttttcc tccaatctca gttcccagat ttcacaaact     180
tcgcacagct aaaactgatg tagttgggga agaagaagca agagaagtaa acgagagagc     240
ggaggaattt ccggacggtc ttcggagaga actgatgccg aacacgtgg ccgtcattat      300 ggacgggaac gtgaggtggg cacagaagag ggggttgccg gcggcgtcgg gtcaccaagc     360
aggtgtgagg tcgttgagag agctggtgga gctctgttgc aaatggggga tcaaagttct     420
ctcggttttc gcattttcct atgataattg gtctcgttcc gaaggggagg ttggtttttct    480 tatgagcttg atcgaaagag tggtcaaagc tgagctgcca attttgggag ggaaggcatt     540
cgagtgtcgt gattgggat ttgtcaaagc ttctgagcaa ctgcaactga taattgatgt      600
agaggagacc actaaggaga actcgcgatt acagttcatt gtggcactta gctatagtgg     660
gcagtgtgac atactacaag catgcaaaaa cattggtcac aaagtaaagg atggccttat     720
cgaaccggaa gacatcaaca aaagcctaat tgaacaggag ctacagacaa actgtactga     780

-continued

```
atttcccttc cctgatctac ttatacgaac tagtggcgaa cttagagtca gcaatttcat    840
gttgtggcaa atagcctaca ctgaactttg cttttttagc acactgtggc ctgattttgg    900
gaaggatgag tttgtggagg ccttaagttc ttttcagaaa aggcagagac gatatggtgg    960
gcgaaactga gtttactaat tacatataga tccccaactt ctgctccatt catatggaga   1020
acttgtatac cattatatga agttaaattc ctgagaattc acttattaca cacagatccc   1080
caacctatac tccattcata tggaaaactt gtaccattat atgaaactca ttcttcagaa   1140
gggaactgat catacccctgc ttccaagttt taagcatgaa gtgccttgcc atttatatac   1200
atacttttac ttcaaaaaaa aaaaaaaaa aa                                   1232
```

<210> SEQ ID NO 12
<211> LENGTH: 309
<212> TYPE: PRT
<213> ORGANISM: Vitis sp

<400> SEQUENCE: 12

```
Met Leu Ser Phe Arg Phe Pro Ile Ser Ala Asp Asn Ala Arg His Thr
  1               5                  10                  15

Phe Lys Ser Lys His Ser Ser Cys Thr Phe Arg Ser Asn Arg Ile Asp
             20                  25                  30

Ser Phe Ser Phe Pro Pro Ile Ser Val Pro Arg Phe His Lys Leu Arg
         35                  40                  45

Thr Ala Lys Thr Asp Val Val Gly Glu Glu Ala Arg Glu Val Asn
     50                  55                  60

Glu Arg Ala Glu Glu Phe Pro Asp Gly Leu Arg Arg Glu Leu Met Pro
 65                  70                  75                  80

Glu His Val Ala Val Ile Met Asp Gly Asn Val Arg Trp Ala Gln Lys
                 85                  90                  95

Arg Gly Leu Pro Ala Ala Ser Gly His Gln Ala Gly Val Arg Ser Leu
            100                 105                 110

Arg Glu Leu Val Glu Leu Cys Cys Lys Trp Gly Ile Lys Val Leu Ser
        115                 120                 125

Val Phe Ala Phe Ser Tyr Asp Asn Trp Ser Arg Ser Glu Gly Glu Val
130                 135                 140

Gly Phe Leu Met Ser Leu Ile Glu Arg Val Val Lys Ala Glu Leu Pro
145                 150                 155                 160

Ile Leu Gly Gly Lys Ala Phe Glu Cys Arg Asp Trp Gly Phe Val Lys
                165                 170                 175

Ala Ser Glu Gln Leu Gln Leu Ile Ile Asp Val Glu Glu Thr Thr Lys
            180                 185                 190

Glu Asn Ser Arg Leu Gln Phe Ile Val Ala Leu Ser Tyr Ser Gly Gln
        195                 200                 205

Cys Asp Ile Leu Gln Ala Cys Lys Asn Ile Gly His Lys Val Lys Asp
    210                 215                 220

Gly Leu Ile Glu Pro Glu Asp Ile Asn Lys Ser Leu Ile Glu Gln Glu
225                 230                 235                 240

Leu Gln Thr Asn Cys Thr Glu Phe Pro Phe Pro Asp Leu Leu Ile Arg
                245                 250                 255

Thr Ser Gly Glu Leu Arg Val Ser Asn Phe Met Leu Trp Gln Ile Ala
            260                 265                 270

Tyr Thr Glu Leu Cys Phe Phe Ser Thr Leu Trp Pro Asp Phe Gly Lys
        275                 280                 285

Asp Glu Phe Val Glu Ala Leu Ser Ser Phe Gln Lys Arg Gln Arg Arg
```

290                 295                 300
Tyr Gly Gly Arg Asn
305

<210> SEQ ID NO 13
<211> LENGTH: 1021
<212> TYPE: DNA
<213> ORGANISM: Oryza sativa

<400> SEQUENCE: 13

| | | | | | |
|---|---|---|---|---|---:|
| acgcacgagc | ttacacgcaa | atgcattgta | gctgtcctct | cgtatggccc | aatgcctaag | 60 |
| catattgcat | ttattatgga | tggtaaccgt | agatatgcta | aattcaggag | tatccaggaa | 120 |
| ggctctggtc | acagggtggg | cttctctgct | ctcattgcca | gcctgctcta | ctgctatgaa | 180 |
| atgggcgtga | agtatatcac | ggtgtatgca | tttagcatcg | ataattttaa | gcgagatccg | 240 |
| actgaggtga | atccttgat | ggagttaatg | gaggaaaaga | tcaatgaact | gctagaaaac | 300 |
| agaaatgtca | tcaacaaggt | taactgtaag | atcaacttct | gggggaactt | ggacatgttg | 360 |
| agcaaatcag | tgagggtagc | agctgagaaa | ctgatggcta | ccactgctga | aaacacggga | 420 |
| ctggtcttct | ctgtttgcat | gccatacaac | tccacttctg | agattgtcaa | tgcggtcaat | 480 |
| aaggtctgtg | cagaaaggag | ggatatactg | cagagggagg | atgctgacag | tgttgcgaat | 540 |
| aatggtgtgt | attcagacat | ttcagtggca | gatctggacc | gccatatgta | cagcgctggt | 600 |
| tgccccgatc | ctgacattgt | gatccggacc | tcaggtgaga | ctcgcctgag | caatttcctt | 660 |
| ctgtggcaga | cgacgttcag | tcatttgcag | aatccagacc | ctctttggcc | ggagttctct | 720 |
| ttcaagcacc | ttgtctgggc | catactccag | taccaaagag | ttcacccttc | tattgagcaa | 780 |
| agcagaaatc | tggctaagaa | gcagctgtaa | tcacatcctc | cctgggagga | gatagaaacc | 840 |
| atcatacaag | atatctgtag | ttacacaata | atctgtattc | tcctgtggta | tctcctggaa | 900 |
| tatgaaatat | ataaggata | gctatgccat | tgtatgcttg | aacatgtgta | tgcttgagtt | 960 |
| ggtccaaatg | tgtgaaatgt | aataacattt | ggtctaaaaa | aaaaaaaaaa | aaaaaaaaa | 1020 |
| a | | | | | | 1021 |

<210> SEQ ID NO 14
<211> LENGTH: 252
<212> TYPE: PRT
<213> ORGANISM: Oryza sativa

<400> SEQUENCE: 14

Met Pro Lys His Ile Ala Phe Ile Met Asp Gly Asn Arg Arg Tyr Ala
 1               5                  10                  15

Lys Phe Arg Ser Ile Gln Glu Gly Ser Gly His Arg Val Gly Phe Ser
            20                  25                  30

Ala Leu Ile Ala Ser Leu Leu Tyr Cys Tyr Glu Met Gly Val Lys Tyr
        35                  40                  45

Ile Thr Val Tyr Ala Phe Ser Ile Asp Asn Phe Lys Arg Asp Pro Thr
    50                  55                  60

Glu Val Lys Ser Leu Met Glu Leu Met Glu Glu Lys Ile Asn Glu Leu
65                  70                  75                  80

Leu Glu Asn Arg Asn Val Ile Asn Lys Val Asn Cys Lys Ile Asn Phe
                85                  90                  95

Trp Gly Asn Leu Asp Met Leu Ser Lys Ser Val Arg Val Ala Ala Glu
            100                 105                 110

Lys Leu Met Ala Thr Thr Ala Glu Asn Thr Gly Leu Val Phe Ser Val

```
                115                 120                 125
Cys Met Pro Tyr Asn Ser Thr Ser Glu Ile Val Asn Ala Val Asn Lys
        130                 135                 140

Val Cys Ala Glu Arg Arg Asp Ile Leu Gln Arg Glu Asp Ala Asp Ser
145                 150                 155                 160

Val Ala Asn Asn Gly Val Tyr Ser Asp Ile Ser Val Ala Asp Leu Asp
                165                 170                 175

Arg His Met Tyr Ser Ala Gly Cys Pro Asp Pro Asp Ile Val Ile Arg
            180                 185                 190

Thr Ser Gly Glu Thr Arg Leu Ser Asn Phe Leu Leu Trp Gln Thr Thr
        195                 200                 205

Phe Ser His Leu Gln Asn Pro Asp Pro Leu Trp Pro Glu Phe Ser Phe
    210                 215                 220

Lys His Leu Val Trp Ala Ile Leu Gln Tyr Gln Arg Val His Pro Ser
225                 230                 235                 240

Ile Glu Gln Ser Arg Asn Leu Ala Lys Lys Gln Leu
                245                 250
```

<210> SEQ ID NO 15
<211> LENGTH: 900
<212> TYPE: DNA
<213> ORGANISM: Oryza sativa

<400> SEQUENCE: 15

```
atgcttggct cacttatgtc ttacttacct tcagtggatt caaagacgga gaacactgat    60
gagttaattg cgactggtgt tcttgctagt ctgcagaatt tcatccgcaa atgcattgta   120
gctgtcctct cgtatggccc aatgcctaag catattgcat ttattatgga tggtaaccgt   180
agatatgcta aattcaggag tatccaggaa ggctctggtc acagggtggg cttctctgct   240
ctcattgcca gcctgctcta ctgctatgaa atgggcgtga agtatatcac ggtgtatgca   300
tttagcatcg ataattttaa gcgagatccg actgaggtga atccttgat ggagttaatg   360
gaggaaaaga tcaatgaact gctagaaaac agaaatgtca tcaacaaggt taactgtaag   420
atcaacttct ggggaacttt ggacatgttg agcaaatcag tgagggtagc agctgagaaa   480
ctgatggcta ccactgctga aaacacggga ctggtcttct ctgtttgcat gccatacaac   540
tccacttctg agattgtcaa tgcggtcaat aaggtctgtg cagaaaggag ggatatactg   600
cagagggagg atgctgacag tgttgcgaat aatggtgtgt attcagacat ttcagtggca   660
gatctggacc gccatatgta cagcgctggt tgccccgatc ctgacattgt gatccggacc   720
tcaggtgaga ctcgcctgag caatttcctt ctgtggcaga cgacgttcag tcatttgcag   780
aatccagacc ctctttggcc ggagttctct ttcaagcacc ttgtctggc catactccag   840
taccaaagag ttcacccttc tattgagcaa agcagaaatc tggctaagaa gcagctgtaa   900
```

<210> SEQ ID NO 16
<211> LENGTH: 299
<212> TYPE: PRT
<213> ORGANISM: Oryza sativa

<400> SEQUENCE: 16

```
Met Leu Gly Ser Leu Met Ser Tyr Leu Pro Ser Val Asp Ser Lys Thr
1               5                   10                  15

Glu Asn Thr Asp Glu Leu Ile Ala Thr Gly Val Leu Ala Ser Leu Gln
            20                  25                  30

Asn Phe Ile Arg Lys Cys Ile Val Ala Val Leu Ser Tyr Gly Pro Met
```

```
            35                  40                  45
Pro Lys His Ile Ala Phe Ile Met Asp Gly Asn Arg Arg Tyr Ala Lys
 50                  55                  60

Phe Arg Ser Ile Gln Glu Gly Ser Gly His Arg Val Gly Phe Ser Ala
 65                  70                  75                  80

Leu Ile Ala Ser Leu Leu Tyr Cys Tyr Glu Met Gly Val Lys Tyr Ile
                 85                  90                  95

Thr Val Tyr Ala Phe Ser Ile Asp Asn Phe Lys Arg Asp Pro Thr Glu
            100                 105                 110

Val Lys Ser Leu Met Glu Leu Met Glu Glu Lys Ile Asn Glu Leu Leu
        115                 120                 125

Glu Asn Arg Asn Val Ile Asn Lys Val Asn Cys Lys Ile Asn Phe Trp
    130                 135                 140

Gly Asn Leu Asp Met Leu Ser Lys Ser Val Arg Val Ala Ala Glu Lys
145                 150                 155                 160

Leu Met Ala Thr Thr Ala Glu Asn Thr Gly Leu Val Phe Ser Val Cys
                165                 170                 175

Met Pro Tyr Asn Ser Thr Ser Glu Ile Val Asn Ala Val Asn Lys Val
            180                 185                 190

Cys Ala Glu Arg Arg Asp Ile Leu Gln Arg Glu Asp Ala Asp Ser Val
        195                 200                 205

Ala Asn Asn Gly Val Tyr Ser Asp Ile Ser Val Ala Asp Leu Asp Arg
    210                 215                 220

His Met Tyr Ser Ala Gly Cys Pro Asp Pro Asp Ile Val Ile Arg Thr
225                 230                 235                 240

Ser Gly Glu Thr Arg Leu Ser Asn Phe Leu Leu Trp Gln Thr Thr Phe
                245                 250                 255

Ser His Leu Gln Asn Pro Asp Pro Leu Trp Pro Glu Phe Ser Phe Lys
            260                 265                 270

His Leu Val Trp Ala Ile Leu Gln Tyr Gln Arg Val His Pro Ser Ile
        275                 280                 285

Glu Gln Ser Arg Asn Leu Ala Lys Lys Gln Leu
    290                 295

<210> SEQ ID NO 17
<211> LENGTH: 1028
<212> TYPE: DNA
<213> ORGANISM: Glycine max

<400> SEQUENCE: 17
ttcccactca gtggtgaatt tgccaaaccg ggataaccgt atccctattc aggaatacaa     60
tgttctcgtt aagactccct attcctctcg ttaaaacacc accttctccc tcttgttatt    120
attctcacta ttatcactat cgttatcgtt atcgttgtta tcatcctttc catcaccgtt    180
cccaaacaca gagtcttatc gtctcgaagc gcggttccgc cattgcgaag tgtcacgctg    240
atagcgtgac acttcgtgat gacggagtct cgctcgccca gagtcgttga gagccacttc    300
cggcggaact cgcggcggag atgatgccga agcatgtggc ggtgataatg gacgggaacg    360
ggaggtgggc gaaggtgaag gggctgccac catcggcggg gcaccaggcg ggggtgcaat    420
cgctgaggaa aatggtgagg ctgtgttgca gctggggaat taaggttcta acggttttcg    480
cgttctctac ggataactgg gttcgcccca aggtggaggt tgatttcttg atgaggctgt    540
ttgagagaac aataaactct gaagttcaaa cttttaagag ggaaggaatt agaatatctg    600
tgattggaga ttcatcaagg ttgcctgagt cttttaaaag aatgatagct agtgcagaag    660
```

```
aggatacaaa acaaaattcg agattccaac ttattgtggc agtgggatac agtggaaaat   720
atgatgttgt gcaagcatgt aaaagtgtag ccaagaaagt caaagatggt cacattcact   780
tggatgacat aaacgaaaac attattgaac aagaattgga aactaattgt actgagtttc   840
cttatcctga tctactaata cgaactagtg gcgagcttag agtgagtaac ttcttgttgt   900
ggcaattagc ctacacagaa ctttatttta atcgggaact ctggccagat tttgggaagg   960
atgagtttgt agatgcatta agttcatttc aacaaagaca agacgctat ggtggtcgac    1020 attcataa                                                           1028
```

<210> SEQ ID NO 18
<211> LENGTH: 322
<212> TYPE: PRT
<213> ORGANISM: Glycine max

<400> SEQUENCE: 18

```
Met Phe Ser Leu Arg Leu Pro Ile Pro Leu Val Lys Thr Pro Pro Ser
 1               5                  10                  15

Pro Ser Cys Tyr Tyr Ser His Tyr Tyr His Tyr Arg Tyr Arg Tyr Arg
                20                  25                  30

Cys Tyr His Pro Phe His His Arg Ser Gln Thr Gln Ser Leu Ile Val
            35                  40                  45

Ser Lys Arg Gly Ser Ala Ile Ala Lys Cys His Ala Asp Ser Val Thr
        50                  55                  60

Leu Arg Asp Asp Gly Val Ser Leu Ala Gln Glu Ser Leu Glu Pro Leu
 65                  70                  75                  80

Pro Ala Glu Leu Ala Ala Glu Met Met Pro Lys His Val Ala Val Ile
                 85                  90                  95

Met Asp Gly Asn Gly Arg Trp Ala Lys Val Lys Gly Leu Pro Pro Ser
            100                 105                 110

Ala Gly His Gln Ala Gly Val Gln Ser Leu Arg Lys Met Val Arg Leu
        115                 120                 125

Cys Cys Ser Trp Gly Ile Lys Val Leu Thr Val Phe Ala Phe Ser Thr
    130                 135                 140

Asp Asn Trp Val Arg Pro Lys Val Glu Val Asp Phe Leu Met Arg Leu
145                 150                 155                 160

Phe Glu Arg Thr Ile Asn Ser Glu Val Gln Thr Phe Lys Arg Glu Gly
                165                 170                 175

Ile Arg Ile Ser Val Ile Gly Asp Ser Ser Arg Leu Pro Glu Ser Leu
            180                 185                 190

Lys Arg Met Ile Ala Ser Ala Glu Glu Asp Thr Lys Gln Asn Ser Arg
        195                 200                 205

Phe Gln Leu Ile Val Ala Val Gly Tyr Ser Gly Lys Tyr Asp Val Val
    210                 215                 220

Gln Ala Cys Lys Ser Val Ala Lys Lys Val Lys Asp Gly His Ile His
225                 230                 235                 240

Leu Asp Asp Ile Asn Glu Asn Ile Ile Glu Gln Glu Leu Glu Thr Asn
                245                 250                 255

Cys Thr Glu Phe Pro Tyr Pro Asp Leu Leu Ile Arg Thr Ser Gly Glu
            260                 265                 270

Leu Arg Val Ser Asn Phe Leu Leu Trp Gln Leu Ala Tyr Thr Glu Leu
        275                 280                 285

Tyr Phe Asn Arg Glu Leu Trp Pro Asp Phe Gly Lys Asp Glu Phe Val
    290                 295                 300
```

Asp Ala Leu Ser Ser Phe Gln Gln Arg Gln Arg Arg Tyr Gly Gly Arg
    305                 310                 315                 320

His Ser

<210> SEQ ID NO 19
<211> LENGTH: 1026
<212> TYPE: DNA
<213> ORGANISM: Triticum aestivum

<400> SEQUENCE: 19

| | | | | | |
|---|---|---|---|---|---|
| atgccgctct | ccaactctac | gtcgtctgtg | ccggccgtca | ccgtcccggc | ggccgaggag | 60 |
| ctcctctcac | aagggctccg | ggcggagtcg | ctgccgcggc | acgtggcgct | ggtgatggac | 120 |
| gggaactcgc | ggtgggcggc | agcgcggggc | ctgccgccga | cggacgggca | cgagcacggg | 180 |
| atgcgcgcgc | tgatgaggac | ggtgcggctc | tcccgcgcct | ggggcatccg | cgtcctcacc | 240 |
| gccttcggtt | tctcgctcga | gaactggaat | cgccccaagg | cggaggttga | cttcttgatg | 300 |
| gccttgatcg | agaggtttat | caacgacaac | ctcgccgagt | tcttgaggga | agggacccgt | 360 |
| ctacgtataa | tcggtgaccg | ctcaaggctg | ccgatctctg | tgcagaagac | tgcacgagac | 420 |
| gccgaggagg | caacaagaaa | caactcgcag | ctcgatctag | tcctagccat | cagctacagc | 480 |
| gggcgaatgg | acattgtgca | ggcatgccgg | aatctcgccc | agaaagtgga | cgccaagctg | 540 |
| ctcaggccgg | aggacatcga | cgagtcgctg | ttcgccgacg | agctccagac | gagcgaaaca | 600 |
| tcttgcccgg | acctgctcat | caggaccagc | ggcgagctga | ggctgagcaa | cttcctgcta | 660 |
| tggcagtcgg | cttactcgga | gctcttcttc | accgacacgc | tctggcctga | tttcggggag | 720 |
| gcccaatatc | tccaagccat | gatggccttc | agagcagag | acaggcgctt | tggaagaaga | 780 |
| aaaaacaatg | cagcgctata | ataaacggt | gcacgcgcgt | gacccgatgc | tcgatcatcc | 840 |
| tctatctatc | tgtatctgcc | tttataatca | gttttatta | ccttcaaata | aagtgtttct | 900 |
| ctcaagatgc | gtggtgtact | ataggagagg | ctactaaaac | ttctctccag | tgattttact | 960 |
| ctatgctata | tgctcattgt | atttgatata | gtttagcatt | catgccgaaa | aaaaaaaaa | 1020 |
| aaaaaa | | | | | | 1026 |

<210> SEQ ID NO 20
<211> LENGTH: 266
<212> TYPE: PRT
<213> ORGANISM: Triticum aestivum

<400> SEQUENCE: 20

Met Pro Leu Ser Asn Ser Thr Ser Ser Val Pro Ala Val Thr Val Pro
  1               5                  10                  15

Ala Ala Glu Glu Leu Leu Ser Gln Gly Leu Arg Ala Glu Ser Leu Pro
             20                  25                  30

Arg His Val Ala Leu Val Met Asp Gly Asn Ser Arg Trp Ala Ala Ala
         35                  40                  45

Arg Gly Leu Pro Pro Thr Asp Gly His Glu His Gly Met Arg Ala Leu
     50                  55                  60

Met Arg Thr Val Arg Leu Ser Arg Ala Trp Gly Ile Arg Val Leu Thr
 65                  70                  75                  80

Ala Phe Gly Phe Ser Leu Glu Asn Trp Asn Arg Pro Lys Ala Glu Val
                 85                  90                  95

Asp Phe Leu Met Ala Leu Ile Glu Arg Phe Ile Asn Asp Asn Leu Ala
            100                 105                 110

-continued

```
Glu Phe Leu Arg Glu Gly Thr Arg Leu Arg Ile Ile Gly Asp Arg Ser
    115                 120                 125
Arg Leu Pro Ile Ser Val Gln Lys Thr Ala Arg Asp Ala Glu Glu Ala
    130                 135                 140
Thr Arg Asn Asn Ser Gln Leu Asp Leu Val Leu Ala Ile Ser Tyr Ser
145                 150                 155                 160
Gly Arg Met Asp Ile Val Gln Ala Cys Arg Asn Leu Ala Gln Lys Val
                165                 170                 175
Asp Ala Lys Leu Leu Arg Pro Glu Asp Ile Asp Glu Ser Leu Phe Ala
            180                 185                 190
Asp Glu Leu Gln Thr Ser Glu Thr Ser Cys Pro Asp Leu Leu Ile Arg
        195                 200                 205
Thr Ser Gly Glu Leu Arg Leu Ser Asn Phe Leu Leu Trp Gln Ser Ala
    210                 215                 220
Tyr Ser Glu Leu Phe Phe Thr Asp Thr Leu Trp Pro Asp Phe Gly Glu
225                 230                 235                 240
Ala Gln Tyr Leu Gln Ala Met Met Ala Phe Gln Ser Arg Asp Arg Arg
                245                 250                 255
Phe Gly Arg Arg Lys Asn Asn Ala Ala Leu
            260                 265
```

<210> SEQ ID NO 21
<211> LENGTH: 11
<212> TYPE: PRT
<213> ORGANISM: Artificial Sequence
<220> FEATURE:
<223> OTHER INFORMATION: Description of Artificial Sequence: Domain I
      of published alignment
<220> FEATURE:
<221> NAME/KEY: UNSURE
<222> LOCATION: (2)..(3)
<223> OTHER INFORMATION: X = any amino acid
<220> FEATURE:
<221> NAME/KEY: UNSURE
<222> LOCATION: (8)
<223> OTHER INFORMATION: X = any amino acid
<220> FEATURE:
<221> NAME/KEY: UNSURE
<222> LOCATION: (10)
<223> OTHER INFORMATION: X = any amino acid
<300> PUBLICATION INFORMATION:
<301> AUTHORS: Apfel, C. M.
<302> TITLE: Use of Genomincs to Indentify Bacterial Undecaprenyl
      Pyrophosphate Synthetase: Cloonig, Expression, and
      Characterization of the Essential uppS Gene
<303> JOURNAL: J. Bacteriol.
<304> VOLUME: 81
<306> PAGES: 483-492
<307> DATE: 1999

<400> SEQUENCE: 21

```
His Xaa Xaa Met Asp Gly Asn Xaa Arg Xaa Ala
 1               5                  10
```

<210> SEQ ID NO 22
<211> LENGTH: 24
<212> TYPE: PRT
<213> ORGANISM: Artificial Sequence
<220> FEATURE:
<223> OTHER INFORMATION: Description of Artificial Sequence: Domain V
      of published alignment
<220> FEATURE:
<221> NAME/KEY: UNSURE
<222> LOCATION: (3)
<223> OTHER INFORMATION: X = any amino acid
<220> FEATURE:
<221> NAME/KEY: UNSURE -continued

```
<222> LOCATION: (7)
<223> OTHER INFORMATION: X = any amino acid
<220> FEATURE:
<221> NAME/KEY: UNSURE
<222> LOCATION: (10)
<223> OTHER INFORMATION: X = any amino acid
<220> FEATURE:
<221> NAME/KEY: UNSURE
<222> LOCATION: (12)
<223> OTHER INFORMATION: X = any amino acid
<220> FEATURE:
<221> NAME/KEY: UNSURE
<222> LOCATION: (20)..(21)
<223> OTHER INFORMATION: X = any amino acid

<400> SEQUENCE: 22

Asp Leu Xaa Ile Arg Thr Xaa Gly Glu Xaa Arg Xaa Ser Asn Phe Leu
 1               5                  10                  15

Leu Trp Gln Xaa Xaa Tyr Xaa Glu
            20

<210> SEQ ID NO 23
<211> LENGTH: 750
<212> TYPE: DNA
<213> ORGANISM: Micrococcus luteus
<300> PUBLICATION INFORMATION:
<301> AUTHORS: Shimizu, N.
<302> TITLE: Molecular Cloning, Expression, and Purification of
       Undecprenyl Diphosphate Synthase:  No Sequence Similarity between
       E- and Z-prenyl Diphosphate Synthases
<303> JOURNAL: J. Biol. Chem.
<304> VOLUME: 273
<306> PAGES: 19476-19481
<307> DATE: 1998

<400> SEQUENCE: 23
atgtttccaa ttaagaagcg aaaagcaata aaaaataata acattaatgc ggcacaaatt       60
ccgaaacata ttgcaatcat tatggacgga atggccgat gggcaaaaca gaaaaaaatg      120
ccgcgcataa aaggacatta tgaaggcatg cagaccgtaa agaaaatcac aagatatgct      180
agtgatttag gtgtaaagta cttaacgctg tacgcatttt caactgaaaa ttggtctcgt      240
cctaaagatg aggttaatta cttgatgaaa ctaccgggtg attttttaaa cacatttta      300 ccggaactca ttgaaaaaaa tgttaaagtt gaaacgattg ctttattga tgatttaccg      360 gaccatacaa aaaagcagt gttagaagcg aaagagaaaa cgaaacataa tacaggttta      420
acgctcgtgt ttgcactgaa ttatggtggg cgtaaagaaa ttatttcagc agtgcagtta      480
atcgcagagc gttacaaatc tggtgaaatt tctttagatg aaattagtga aactcatttt      540
aatgaatatt tatttacagc aaatatgcct gatcctgagt tgttaatcag aacttccggt      600
gaagaacgtt taagtaactt tttaatttgg caatgttcat atagtgagtt tgtatttata      660
gatgaattct ggccggattt taatgaagaa agtttagcac aatgtatatc aatatatcag      720
aatcgtcatc gacgttttgg tggattataa                                       750

<210> SEQ ID NO 24
<211> LENGTH: 249
<212> TYPE: PRT
<213> ORGANISM: Micrococcus luteus

<400> SEQUENCE: 24

Met Phe Pro Ile Lys Lys Arg Lys Ala Ile Lys Asn Asn Asn Ile Asn
 1               5                  10                  15

Ala Ala Gln Ile Pro Lys His Ile Ala Ile Ile Met Asp Gly Asn Gly
            20                  25                  30
```

```
Arg Trp Ala Lys Gln Lys Lys Met Pro Arg Ile Lys Gly His Tyr Glu
         35                  40                  45

Gly Met Gln Thr Val Lys Lys Ile Thr Arg Tyr Ala Ser Asp Leu Gly
     50                  55                  60

Val Lys Tyr Leu Thr Leu Tyr Ala Phe Ser Thr Glu Asn Trp Ser Arg
 65                  70                  75                  80

Pro Lys Asp Glu Val Asn Tyr Leu Met Lys Leu Pro Gly Asp Phe Leu
                 85                  90                  95

Asn Thr Phe Leu Pro Glu Leu Ile Glu Lys Asn Val Lys Val Glu Thr
             100                 105                 110

Ile Gly Phe Ile Asp Asp Leu Pro Asp His Thr Lys Lys Ala Val Leu
         115                 120                 125

Glu Ala Lys Glu Lys Thr Lys His Asn Thr Gly Leu Thr Leu Val Phe
     130                 135                 140

Ala Leu Asn Tyr Gly Gly Arg Lys Glu Ile Ile Ser Ala Val Gln Leu
145                 150                 155                 160

Ile Ala Glu Arg Tyr Lys Ser Gly Glu Ile Ser Leu Asp Glu Ile Ser
                 165                 170                 175

Glu Thr His Phe Asn Glu Tyr Leu Phe Thr Ala Asn Met Pro Asp Pro
             180                 185                 190

Glu Leu Leu Ile Arg Thr Ser Gly Glu Glu Arg Leu Ser Asn Phe Leu
         195                 200                 205

Ile Trp Gln Cys Ser Tyr Ser Glu Phe Val Phe Ile Asp Glu Phe Trp
     210                 215                 220

Pro Asp Phe Asn Glu Glu Ser Leu Ala Gln Cys Ile Ser Ile Tyr Gln
225                 230                 235                 240

Asn Arg His Arg Arg Phe Gly Gly Leu
                 245
```

<210> SEQ ID NO 25
<211> LENGTH: 861
<212> TYPE: DNA
<213> ORGANISM: Saccharomyces cerevisiae
<308> DATABASE ACCESSION NUMBER: AB013497

<400> SEQUENCE: 25

| | | | | |
|---|---|---|---|---|
| atggaaacgg atagtggtat acctggtcat tcatttgtgt taaagtggac aaaaaacatc | 60 |
| ttttcgcgca cattgcgtgc atctaactgt gtacctagac atgttgggtt catcatggat | 120 |
| gggaacagga gattcgctag aaagaaagag atggacgtaa aggagggcca cgaggcagga | 180 |
| tttgttagta tgagtagaat cttagaactg tgttatgaag caggagtcga tacggctacc | 240 |
| gtgtttgcct tttcaattga aaatttcaag aggagctcac gggaagttga atcactgatg | 300 |
| actttagcgc gcgaaaggat acgacaaatc acagaacgtg gagagctggc ctgtaagtat | 360 |
| ggggtacgca ttaaaattat cggcgatctc tctttgttgg ataagtctct attagaagat | 420 |
| gttcgggttg ctgtggaaac tacaaagaac aacaaagggg ccacgttaaa tatctgcttt | 480 |
| ccatatacag gcaggaaaga aatcttgcat gccatgaaag aaacaattgt tcaacataag | 540 |
| aagggcgccg ctatagacga aagcacgtta gaatcgcatc tctacacggc ggggtaccc | 600 |
| cctttagatt tattgattag acaagtggc gtttccagat taagtgactt tttgatatgg | 660 |
| caggcatcga gtaagggcgt acgcatcgaa ttgctggatt gtttatggcc agagtttgga | 720 |
| cctatacgga tggcatggat tttattaaaa ttttcgtttc acaaatcctt tttaaacaaa | 780 |
| gagtacagat tagaggaagg tgattatgac gaggaaacca atgggaccc catcgatttg | 840 | aaagaaaaaa agttgaatta a                                                861

<210> SEQ ID NO 26
<211> LENGTH: 286
<212> TYPE: PRT
<213> ORGANISM: Saccharomyces cerevisiae

<400> SEQUENCE: 26

Met Glu Thr Asp Ser Gly Ile Pro Gly His Ser Phe Val Leu Lys Trp
 1               5                  10                  15

Thr Lys Asn Ile Phe Ser Arg Thr Leu Arg Ala Ser Asn Cys Val Pro
            20                  25                  30

Arg His Val Gly Phe Ile Met Asp Gly Asn Arg Arg Phe Ala Arg Lys
        35                  40                  45

Lys Glu Met Asp Val Lys Glu Gly His Glu Ala Gly Phe Val Ser Met
    50                  55                  60

Ser Arg Ile Leu Glu Leu Cys Tyr Glu Ala Gly Val Asp Thr Ala Thr
65                  70                  75                  80

Val Phe Ala Phe Ser Ile Glu Asn Phe Lys Arg Ser Ser Arg Glu Val
                85                  90                  95

Glu Ser Leu Met Thr Leu Ala Arg Glu Arg Ile Arg Gln Ile Thr Glu
            100                 105                 110

Arg Gly Glu Leu Ala Cys Lys Tyr Gly Val Arg Ile Lys Ile Ile Gly
        115                 120                 125

Asp Leu Ser Leu Leu Asp Lys Ser Leu Leu Glu Asp Val Arg Val Ala
    130                 135                 140

Val Glu Thr Thr Lys Asn Asn Lys Arg Ala Thr Leu Asn Ile Cys Phe
145                 150                 155                 160

Pro Tyr Thr Gly Arg Glu Glu Ile Leu His Ala Met Lys Glu Thr Ile
                165                 170                 175

Val Gln His Lys Lys Gly Ala Ala Ile Asp Glu Ser Thr Leu Glu Ser
            180                 185                 190

His Leu Tyr Thr Ala Gly Val Pro Pro Leu Asp Leu Leu Ile Arg Thr
        195                 200                 205

Ser Gly Val Ser Arg Leu Ser Asp Phe Leu Ile Trp Gln Ala Ser Ser
    210                 215                 220

Lys Gly Val Arg Ile Glu Leu Leu Asp Cys Leu Trp Pro Glu Phe Gly
225                 230                 235                 240

Pro Ile Arg Met Ala Trp Ile Leu Leu Lys Phe Ser Phe His Lys Ser
                245                 250                 255

Phe Leu Asn Lys Glu Tyr Arg Leu Glu Glu Gly Asp Tyr Asp Glu Glu
            260                 265                 270

Thr Asn Gly Asp Pro Ile Asp Leu Lys Glu Lys Lys Leu Asn
        275                 280                 285

<210> SEQ ID NO 27
<211> LENGTH: 1032
<212> TYPE: DNA
<213> ORGANISM: Saccharomyces cerevisiae
<300> PUBLICATION INFORMATION:
<308> DATABASE ACCESSION NUMBER: AB013498

<400> SEQUENCE: 27
atgaaaatgc ccagtattat tcagattcag tttgtagccc taaaaggct tttggtagaa         60 accaaagaac agatgtgctt cgcagtgaaa agtatatttc agagagtatt tgcgtgggtt       120

```
atgtcattaa gcttgttttc atggttttat gtaaatcttc agaatatttt gataaaagca      180
ttaagggtag ggccagtgcc tgaacatgtc tcctttatca tggatggtaa ccggagatat      240
gccaagtcaa gaaggctacc agtaaaaaaa ggccatgaag ctggtgggtt aacgttacta      300
acactactgt atatctgcaa aagattgggt gtaaaatgtg tttccgccta tgcattttct      360
attgaaaatt ttaatagacc aaaagaagaa gtagatacgc taatgaattt gtttacggta      420
aagcttgatg aattcgcaaa aagagccaag gactataagg atcccttata cggatctaaa      480
ataagaatag taggtgatca atctttacta tctccagaaa tgagaaaaaa aattaaaaaa      540
gtggaagaaa tcacacagga tggagacgat ttcactttat ttatatgttt tccttacact      600
tcaagaaatg atatgttaca tactattcgt gattcagttg aagaccattt ggaaaataaa      660
tcaccaagga ttaataTaag aaaatttact aataaaatgt acatgggttt ccattccaat      720
aaatgtgaat tattaatcag aacaagtggg cataggaggc tctcagacta tatgctatgg      780
caagtacatg aaaatgccac cattgaattt agtgatacgt gtggccaaa ttttagcttc      840 tttgctatgt acctgatgat tctcaaatgg tccttctttt ccaccattca aaaatataat      900
gagaagaatc actcattgtt tgaaaaaata catgaaagcg ttccttcaat atttaaaaaa      960
aagaaaacag ctatgtctTt gtacaacttt ccaaaccccc ccatttcagt ttcggttaca     1020
ggagatgaat aa                                                         1032

<210> SEQ ID NO 28
<211> LENGTH: 343
<212> TYPE: PRT
<213> ORGANISM: Saccharomyces cerevisiae

<400> SEQUENCE: 28

Met Lys Met Pro Ser Ile Ile Gln Ile Gln Phe Val Ala Leu Lys Arg
  1               5                  10                  15

Leu Leu Val Glu Thr Lys Glu Gln Met Cys Phe Ala Val Lys Ser Ile
             20                  25                  30

Phe Gln Arg Val Phe Ala Trp Val Met Ser Leu Ser Leu Phe Ser Trp
         35                  40                  45

Phe Tyr Val Asn Leu Gln Asn Ile Leu Ile Lys Ala Leu Arg Val Gly
     50                  55                  60

Pro Val Pro Glu His Val Ser Phe Ile Met Asp Gly Asn Arg Arg Tyr
 65                  70                  75                  80

Ala Lys Ser Arg Arg Leu Pro Val Lys Lys Gly His Glu Ala Gly Gly
                 85                  90                  95

Leu Thr Leu Leu Thr Leu Leu Tyr Ile Cys Lys Arg Leu Gly Val Lys
            100                 105                 110

Cys Val Ser Ala Tyr Ala Phe Ser Ile Glu Asn Phe Asn Arg Pro Lys
        115                 120                 125

Glu Glu Val Asp Thr Leu Met Asn Leu Phe Thr Val Lys Leu Asp Glu
    130                 135                 140

Phe Ala Lys Arg Ala Lys Asp Tyr Lys Asp Pro Leu Tyr Gly Ser Lys
145                 150                 155                 160

Ile Arg Ile Val Gly Asp Gln Ser Leu Leu Ser Pro Glu Met Arg Lys
                165                 170                 175

Lys Ile Lys Lys Val Glu Glu Ile Thr Gln Asp Gly Asp Phe Thr
            180                 185                 190

Leu Phe Ile Cys Phe Pro Tyr Thr Ser Arg Asn Asp Met Leu His Thr
        195                 200                 205
```

```
Ile Arg Asp Ser Val Glu Asp His Leu Glu Asn Lys Ser Pro Arg Ile
    210                 215                 220

Asn Ile Arg Lys Phe Thr Asn Lys Met Tyr Met Gly Phe His Ser Asn
225                 230                 235                 240

Lys Cys Glu Leu Leu Ile Arg Thr Ser Gly His Arg Arg Leu Ser Asp
                245                 250                 255

Tyr Met Leu Trp Gln Val His Glu Asn Ala Thr Ile Glu Phe Ser Asp
            260                 265                 270

Thr Leu Trp Pro Asn Phe Ser Phe Phe Ala Met Tyr Leu Met Ile Leu
        275                 280                 285

Lys Trp Ser Phe Phe Ser Thr Ile Gln Lys Tyr Asn Glu Lys Asn His
    290                 295                 300

Ser Leu Phe Glu Lys Ile His Glu Ser Val Pro Ser Ile Phe Lys Lys
305                 310                 315                 320

Lys Lys Thr Ala Met Ser Leu Tyr Asn Phe Pro Asn Pro Pro Ile Ser
                325                 330                 335

Val Ser Val Thr Gly Asp Glu
            340
```

```
<210> SEQ ID NO 29
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 29
gctctagaga aggttaagtc agtttagcat cg                              32

<210> SEQ ID NO 30
<211> LENGTH: 36
<212> TYPE: DNA
<213> ORGANISM: Artificial Sequence
<220> FEATURE:
<223> OTHER INFORMATION: Description of Artificial Sequence:primer

<400> SEQUENCE: 30
ggggtacctt attttaaata ttccttatgc ttctcc                          36

<210> SEQ ID NO 31
<211> LENGTH: 26
<212> TYPE: DNA
<213> ORGANISM: Artificial Sequence
<220> FEATURE:
<223> OTHER INFORMATION: Description of Artificial Sequence:primer

<400> SEQUENCE: 31
gtggatccat gcttggctca cttatg                                     26

<210> SEQ ID NO 32
<211> LENGTH: 26
<212> TYPE: DNA
<213> ORGANISM: Artificial Sequence
<220> FEATURE:
<223> OTHER INFORMATION: Description of Artificial Sequence:primer

<400> SEQUENCE: 32
ttgagctcta tctcctccca gggagg                                     26

<210> SEQ ID NO 33
<211> LENGTH: 27
<212> TYPE: DNA
```

```
<213> ORGANISM: Artificial Sequence
<220> FEATURE:
<223> OTHER INFORMATION: Description of Artificial Sequence:primer

<400> SEQUENCE: 33
acggatccat gttctcgtta agactcc                                            27

<210> SEQ ID NO 34
<211> LENGTH: 26
<212> TYPE: DNA
<213> ORGANISM: Artificial Sequence
<220> FEATURE:
<223> OTHER INFORMATION: Description of Artificial Sequence:primer

<400> SEQUENCE: 34
tcgagctctt atgaatgtcg accacc                                             26

<210> SEQ ID NO 35
<211> LENGTH: 37
<212> TYPE: DNA
<213> ORGANISM: Artificial Sequence
<220> FEATURE:
<223> OTHER INFORMATION: Description of Artificial Sequence:primer

<400> SEQUENCE: 35
ctagtctaga atctcccctc cgataaccaa aaaatcc                                 37

<210> SEQ ID NO 36
<211> LENGTH: 34
<212> TYPE: DNA
<213> ORGANISM: Artificial Sequence
<220> FEATURE:
<223> OTHER INFORMATION: Description of Artificial Sequence:primer

<400> SEQUENCE: 36
ggggtaccta gggtttaact tagaaactat ttag                                    34

<210> SEQ ID NO 37
<211> LENGTH: 1200
<212> TYPE: DNA
<213> ORGANISM: arabidopsis

<400> SEQUENCE: 37
tatatttgat taaaccagaa agaaagttta aacactaatc cctaatcagc aattttctcc         60
cttcccctaa aaatcagccg tatcatatgc tcattccatt tgcattcccc acagaaagaa        120
aagaaaaact tcattctctt gtttatattt cactcgcaac aaaaaaaaca aaaaaaaaca        180
aagtgtgttc ttaaattatc ttctctgata accaaaaaag ccctattttc cgagatgaat        240
accctagaag aagtagatga atccactcat atcttcaacg ctttgatgag tctaatgagg        300 aaattttgt tcagagttct atgcgtcggt ccaatcccta ctaacatttc attcatcatg         360
gatggaaacc gcaggttcgc taagaaacac aatcttatag gcctagatgc aggacataga        420
gctggtttca tatccgtgaa atatattctt caatactgca agagattgg tgtaccgtac         480 gtcacactcc acgcgtttgg tatggataat ttcaagagag gacctgaaga agtcaagtgt        540
gtgatggatc taatgcttga gaaagtcgag ctcgcgatcg atcaagctgt atcagggaat        600
atgaacggcg tgagaataat ctttgccggt gatttggatt cgttaaacga gcatttagga        660
gctgcgacaa agaaactgat ggagcttacg gaggagaata gagatctgat tgtggtggtt        720
tgcgttgctt acagcacaag tctcgagatt gttcacgctg ttcgaaaatc ttgtgttaga        780
aaatgtacga atggagatga tcttgtactt ttggagttga gtgatgttga agagtgtatg        840
```

```
tatacatcga ttgtgccggt tccggatctt gtgataagaa ccggaggagg agatcggctg      900
agtaacttca tgacgtggca aacttcgagg tctcttcttc acagaacgga ggctctttgg      960
ccggagttag ggctctggca tttggtttgg gcaattctta aattccaaag aatgcaagat     1020
tacttgacga agaagaaaaa gctcgattag atagtttcta aagttaaacc ctgcaggaaa     1080
gaacttttaa ctctttatta cgtttaattt acgtgtttct atgactggaa acgagaaagc     1140
tcacaagcaa atcttttta ttatgtattg gatccgtata acaaacacga atatacaaaa     1200
```